(12) United States Patent
Brown et al.

(10) Patent No.: US 10,550,189 B2
(45) Date of Patent: Feb. 4, 2020

(54) ANTI IL-36R ANTIBODIES

(71) Applicant: Boehringer Ingelheim International GmbH, Ingelheim am Rhein (DE)

(72) Inventors: Su-Ellen Brown, Shelton, CT (US); Keith Canada, Blacksburg, VA (US); Lukasz Chlewicki, New Lenox, IL (US); Michael Howell, Montgomery Village, MD (US); Detlev Mennerich, Kirchdorf an der Iller (DE); Joseph Robert Woska, Jr., Yorktown Heights, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 102 days.

(21) Appl. No.: 14/676,365

(22) Filed: Apr. 1, 2015

(65) Prior Publication Data

US 2015/0203584 A1 Jul. 23, 2015
US 2017/0298135 A9 Oct. 19, 2017

Related U.S. Application Data

(62) Division of application No. 13/676,511, filed on Nov. 14, 2012, now Pat. No. 9,023,995.

(60) Provisional application No. 61/713,713, filed on Oct. 15, 2012, provisional application No. 61/644,111, filed on May 8, 2012, provisional application No. 61/560,554, filed on Nov. 16, 2011.

(51) Int. Cl.
| | |
|---|---|
| C07K 16/28 | (2006.01) |
| G01N 33/68 | (2006.01) |
| G01N 33/564 | (2006.01) |
| C07K 16/24 | (2006.01) |
| A61K 39/00 | (2006.01) |

(52) U.S. Cl.
CPC ........ *C07K 16/2866* (2013.01); *C07K 16/244* (2013.01); *G01N 33/564* (2013.01); *G01N 33/6869* (2013.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01); *G01N 2333/7155* (2013.01); *G01N 2800/205* (2013.01)

(58) Field of Classification Search
None
See application file for complete search history.

(56) References Cited

U.S. PATENT DOCUMENTS

| | | | |
|---|---|---|---|
| 6,416,973 B1 | 7/2002 | Bakker et al. | |
| 6,953,843 B2 | 10/2005 | Bakker et al. | |
| 7,332,574 B2 | 2/2008 | Bakker et al. | |
| 8,034,771 B2 | 10/2011 | Sims et al. | |
| 8,481,021 B2 | 7/2013 | Sims et al. | |
| 2004/0110930 A1* | 6/2004 | Reinl | C07H 21/04 530/387.1 |
| 2004/0132085 A1 | 7/2004 | Bakker et al. | |
| 2004/0177391 A1 | 9/2004 | Bakker et al. | |
| 2005/0084900 A1 | 4/2005 | Bakker et al. | |
| 2007/0041905 A1 | 2/2007 | Hoffman et al. | |
| 2007/0071675 A1 | 3/2007 | Wu et al. | |
| 2008/0171035 A1 | 7/2008 | Bakker et al. | |
| 2008/0292623 A1 | 11/2008 | Bakker et al. | |
| 2009/0263403 A1 | 10/2009 | Bakker et al. | |
| 2010/0129374 A1 | 5/2010 | Bakker et al. | |
| 2010/0150945 A1 | 6/2010 | Bigler et al. | |
| 2010/0221252 A1 | 9/2010 | Bigler et al. | |
| 2011/0110852 A1* | 5/2011 | Miller | C07K 16/00 424/1.49 |
| 2011/0159011 A1 | 6/2011 | Carrier et al. | |
| 2012/0177647 A1 | 7/2012 | Bigler et al. | |

FOREIGN PATENT DOCUMENTS

| | | |
|---|---|---|
| EP | 1003861 A2 | 5/2000 |
| EP | 2176294 A1 | 4/2010 |
| WO | 9906557 A2 | 2/1999 |
| WO | 2008033333 A2 | 3/2008 |
| WO | 2008133857 A1 | 11/2008 |
| WO | 2009006112 A1 | 1/2009 |
| WO | 2010025369 A2 | 3/2010 |
| WO | 2013074569 A1 | 5/2013 |
| WO | 2016168542 A1 | 10/2016 |

OTHER PUBLICATIONS

Vajdos et al. (J Mol Biol. Jul. 5, 2002;320(2):415-28).*
Brown et al. (J Immunol. May 1996;156(9):3285-91).*
Arend, William P. et al. "IL-1, IL-18, and IL-33 families of cytokines" Immunological Reviews (2008) vol. 223, pp. 20-22.
Blumberg, Hal et al. "IL-1RL2 and Its Ligands Contribute to the Cytokine Network in Psoriasis" The Journal of Immunology (2010) vol. 185, pp. 4354-4362.
Blumberg, Hal et al. "Opposing activities of two novel members of the IL-1 ligand family regulate skin inflammation" The Journal of Experimental Medicine (2007) vol. 204, No. 11, pp. 2603-2614.
Bowie, James U. et al. "Deciphering the Message in Protein Sequences: Tolerance to Amino Acid Substitutions" Science (1990) vol. 247, pp. 1306-1310.
Burgess, Wilson H. et al. "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue" Journal of Cell Biology, (1990) vol. 111, pp. 2129-2138.
Chustz, Regina T. et al. "Regulation and Function of the IL-1 Family Cytokine IL-1F9 in Human Bronchial Epithelial Cells" Am J Respir Cell Mol Biol (2011) vol. 45, pp. 145-153.

(Continued)

*Primary Examiner* — Brian Gangle
*Assistant Examiner* — Andrea K McCollum
(74) *Attorney, Agent, or Firm* — Atabak R. Royaee

(57) ABSTRACT

The present invention relates to anti-interleukin-36R (anti-IL-36R) binding compounds, in particular new anti-IL-36R antibodies and therapeutic and diagnostic methods and compositions for using the same.

21 Claims, 4 Drawing Sheets
Specification includes a Sequence Listing.

(56) References Cited

OTHER PUBLICATIONS

Creative Diagnostics "Mouse anti-IL1RL2 Monoclonal Antibody" Product Information. Gene ID 8808. mRNA Ref Seq NM_003854. (2004).
Dinarello, Charles et al. "IL-1 family nomenclature" Nature Immunology (2010) vol. 11, pp. 973-974.
International Search Report for PCT/US2012/064933 filed Nov. 14, 2012, dated Feb. 7, 2013.
Johnston, Andrew et al. "IL-1F5, -F6, -F8, and -F9: A Novel IL-1 Family Signaling System that is Active in Psoriasis and Promotes Keratinocyte Antimicrobial Peptide Expression" The Journal of Immunology (2011) vol. 186, pp. 2613-2622.
Lazar, Eliane et al. "Transforming Growth Factor a: Mutation of Aspartic Acid 47 and Leucine 48 Results in Different Biological Activities" Molecular and Cellular Biology (1988) vol. 8, No. 3, pp. 1247-1252.
Lingel, Andreas et al. "Structure of IL-33 and its Interaction with the ST2 and IL-1RAcP Receptors—Insight into Heterotrimeric IL-1 Signaling Complexes" Structure (2009) vol. 17, pp. 1398-1410.
Lovenberg, Timothy W. et al. "Cloning of a cDNA encoding a novel interleukin-1 receptor related protein (IL1R-rp2)" Journal of Neuroimmunology, (1996) vol. 70, pp. 113-122.
Magne, David et al. "The new IL-1 Family Member IL-1F8 stimulates production of inflammatory mediators by synovial fibroblasts and articular chondrocytes" Arthritis Research & Therapy (2006) vol. 8:R80, 11 pgs.
Marrakchi, Slaheddine et al. "Interleukin-36-Receptor Antagonist Deficiency and Generalized Pustular Psoriasis" New England Journal of Medicine (2011) vol. 365 pp. 620-628.
McMahan, Catherine J. et al. "A Novel IL-1 receptor, cloned from B cells by mammalian expression, is expressed in many cell types" EMBO Journal (1991) vol. 10, No. 10, pp. 2821-2832.
NCBI GENE databases (IL1RL2 interleukin 1 receptor-like 2 [*Homo sapiens* (human)]; http:www.ncbi.nlm.nib.gov/gene/8808; downloaded May 18, 2014, 8 pgs.
Ramadas, Ravisankar A. et al. "IL-36a Exerts Pro-Inflammatory Effects in the Lungs of Mice" PLOS one (2012) vol. 7, Issue 9, e45784, 17 pgs.
Ramadas, Ravisankar A. et al. "Interleukin-1 Family Member 9 Stimulates Chemokine Production and Neutrophil Influx in Mouse Lungs" Am J Respir Cell Mol Biol (2011) vol. 44, pp. 134-145.
Towne, Jennifer E. et al. "Interleukin (IL)-1F6, IL-1F8, and IL-1F9 Signal through IL-1Rrp2 and IL-1RAcP to Activate the Pathway Leading to Nf-kB and MAPKs*" The Journal of Biological Chemistry (2004) vol. 279, No. 14, pp. 13677-13688.
Towne, Jennifer E. et al. "Interleukin-36 (IL-36) Ligands Require Processing for Full Agonist (IL-36a, IL-36b, and IL-36g) or Antagonist (IL-36Ra) Activity" The Journal of Biological Chemistry (2011) vol. 286, No. 49, pp. 42594-42602.
Steidl et al., "In vitro affinity maturation of human GM-CSF antibodies by targeted CDR-diversification", Mol. Immunol, 2008, vol. 46, pp. 135-144.
International Search Report PCT/US2018/024296 dated Jun. 22, 2018.
Born, Teresa et al. "Identification and characterization of two members of a novel class of the interleukin-1 receptor (IL-1R) family. Delineation of a new class of IL-1R-related proteins based on signaling" The Journal of Biological Chemistry (2000), vol. 275, pp. 29946-29954.
Debets, Reno et al. "Two Novel IL-1 Family Members, IL-1d and IL-1e Function as an Antagonist and Agonist of NF-kB Activation Through the Orphan IL-1 Receptor-Related Protein 21" The Journal of Immunology (2001) vol. 167, pp. 1440-1446.
Matsuba et al., "Preparation of Super-High Affinity Rabbit Monoclonal Antibodies Against Estradiol.: Application to Highly Sensitive Estradiol Measurement", TOSOH Research & Technol. Review. 2008, vol. 52, pp. 3-9.
NCBI GENE databases (IL1RL2 interleukin 1 receptor-like 2 [Homo sapiens (human)]; http:www.ncbi.nlm.nib.gov/gene/8808; downloaded May 18, 2014, 8 pages.
Tortola, Luigi et al. "Psoriasiform dermatitis is driven by IL-36-mediated DC-keratinocyte crosstalk" The Journal of Clinical Investigation (2012) vol. 122, No. 11, pp. 3965-3976.

* cited by examiner

SEQUENCE LISTING

```
<160> NUMBER OF SEQ ID NOS: 140

<210> SEQ ID NO 1
<211> LENGTH: 108
<212> TYPE: PRT
<213> ORGANISM: Mus sp.

<400> SEQUENCE: 1

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Lys Lys Pro Gly Ser Ser Pro Lys Leu Trp
        35                  40                  45

Val Tyr Ser Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln His His Arg Ser Pro
                85                  90                  95

Val Thr Phe Gly Ser Gly Thr Lys Leu Glu Met Lys
                100                 105

<210> SEQ ID NO 2
<211> LENGTH: 107
<212> TYPE: PRT
<213> ORGANISM: Mus sp.

<400> SEQUENCE: 2

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Ala Trp Tyr Gln Gln Arg Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Gln Phe Ser Phe Asn Ile Arg Ser Leu Gln Ala
65                  70                  75                  80

Glu Asp Phe Ala Ser Tyr Tyr Cys Gln Gln Val Tyr Thr Thr Pro Leu
                85                  90                  95
```

-continued

```
Thr Phe Gly Gly Gly Thr Lys Leu Glu Ile Lys
            100                 105

<210> SEQ ID NO 3
<211> LENGTH: 107
<212> TYPE: PRT
<213> ORGANISM: Mus sp.

<400> SEQUENCE: 3

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
            20                  25                  30

Leu Gly Trp Tyr Gln Gln Lys Pro Gly Lys Ser Pro Gln Leu Leu Ile
        35                  40                  45

Tyr Arg Ser Thr Thr Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Ala Asp Phe Ala Ser Tyr Tyr Cys Gln Gln Leu Tyr Ser Ala Pro Tyr
                85                  90                  95

Thr Phe Gly Gly Gly Thr Lys Leu Glu Ile Arg
            100                 105

<210> SEQ ID NO 4
<211> LENGTH: 112
<212> TYPE: PRT
<213> ORGANISM: Mus sp.

<400> SEQUENCE: 4

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ala Gly Thr Lys Leu Glu Leu Lys
            100                 105                 110

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Tyr Lys Tyr
            20                  25                  30
```

Leu Asn Trp Tyr Gln Gln Lys Pro Asp Gly Thr Leu Lys Leu Leu Ile
        35                  40                  45

Tyr Tyr Thr Ser Gly Leu His Ser Gly Val Pro Ser Arg Phe Ser Gly
 50                  55                  60

Ser Gly Ser Gly Thr Asp Phe Ser Leu Thr Ile Ser Asn Leu Glu Pro
 65                  70                  75                  80

Glu Asp Ile Ala Thr Tyr Phe Cys Gln Gln Asp Ser Lys Phe Pro Trp
                 85                  90                  95

Thr Phe Gly Gly Asp Thr Lys Leu Glu Ile Lys
            100                 105

<210> SEQ ID NO 6
<211> LENGTH: 108
<212> TYPE: PRT
<213> ORGANISM: Mus sp.

<400> SEQUENCE: 6

Gln Ile Val Leu Thr Gln Ser Pro Ala Ile Met Ser Ala Ser Leu Gly
 1               5                  10                  15

Glu Arg Val Thr Met Thr Cys Thr Ala Ser Ser Ser Val Ser Ser Ser
                 20                  25                  30

Tyr Phe His Trp Tyr Gln Gln Lys Pro Gly Ser Ser Pro Lys Leu Trp
             35                  40                  45

Ile Tyr Arg Thr Ser Asn Leu Ala Ser Gly Val Pro Gly Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Phe His Arg Ser Pro
                 85                  90                  95

Leu Thr Phe Gly Ala Gly Thr Lys Leu Glu Leu Lys
            100                 105

<210> SEQ ID NO 7
<211> LENGTH: 107
<212> TYPE: PRT
<213> ORGANISM: Mus sp.

<400> SEQUENCE: 7

Asp Ile Val Met Thr Gln Ser Gln Lys Phe Leu Ser Thr Ser Val Gly
 1               5                  10                  15

Val Arg Val Ser Val Thr Cys Lys Ala Ser Gln Asp Val Gly Thr Asn
                 20                  25                  30

Val Leu Trp Tyr Gln Gln Lys Ile Gly Gln Ser Pro Lys Pro Leu Ile
             35                  40                  45

Tyr Ser Ala Ser Tyr Arg His Ser Gly Val Pro Asp Arg Phe Thr Gly
 50                  55                  60

Ser Gly Ser Gly Thr Asp Phe Thr Leu Ile Ile Ser Asn Val Gln Ser
 65                  70                  75                  80

Glu Asp Leu Ala Glu Tyr Phe Cys Gln Gln Tyr Ser Arg Tyr Pro Leu
                 85                  90                  95

Thr Phe Gly Pro Gly Thr Lys Leu Glu Leu Lys
            100                 105

<210> SEQ ID NO 8
<211> LENGTH: 107
<212> TYPE: PRT
<213> ORGANISM: Mus sp.

```
<400> SEQUENCE: 8

Asp Ile Val Met Thr Gln Ser Gln Lys Phe Leu Ser Thr Ser Val Gly
1               5                   10                  15

Val Arg Val Ser Val Thr Cys Lys Ala Ser Gln Asp Val Gly Thr Asn
            20                  25                  30

Val Leu Trp Tyr Gln Gln Lys Ile Gly Gln Ser Pro Lys Ala Leu Ile
        35                  40                  45

Tyr Ser Ala Ser Tyr Arg His Ser Gly Val Pro Asp Arg Phe Thr Gly
    50                  55                  60

Ser Gly Ser Gly Thr Asp Phe Thr Leu Ile Ile Thr Asn Val Gln Ser
65                  70                  75                  80

Glu Asp Leu Ala Glu Tyr Phe Cys Gln Gln Tyr Ser Arg Tyr Pro Leu
                85                  90                  95

Thr Phe Gly Pro Gly Thr Lys Leu Glu Leu Lys
            100                 105

<210> SEQ ID NO 9
<211> LENGTH: 107
<212> TYPE: PRT
<213> ORGANISM: Mus sp.

<400> SEQUENCE: 9

Asp Ile Val Met Thr Gln Ser Gln Lys Phe Met Ser Ala Thr Val Gly
1               5                   10                  15

Gly Arg Val Asn Ile Thr Cys Lys Ala Ser Gln Asn Val Gly Arg Ala
            20                  25                  30

Val Ala Trp Tyr Gln Gln Lys Pro Gly Gln Ser Pro Lys Leu Leu Thr
        35                  40                  45

His Ser Ala Ser Asn Arg Tyr Thr Gly Val Pro Asp Arg Phe Thr Gly
    50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Asp Leu Lys
            100                 105

<210> SEQ ID NO 10
<211> LENGTH: 107
<212> TYPE: PRT
<213> ORGANISM: Mus sp.

<400> SEQUENCE: 10

Asp Ile Gln Met Thr Gln Ser Pro Ala Ser Gln Ser Ala Ser Leu Gly
1               5                   10                  15

Glu Ser Val Thr Phe Ser Cys Leu Ala Ser Gln Thr Ile Gly Thr Trp
            20                  25                  30

Leu Gly Trp Tyr Gln Gln Lys Pro Gly Lys Ser Pro Gln Leu Leu Ile
        35                  40                  45

Tyr Arg Ala Thr Ser Leu Ala Asp Gly Val Pro Ser Arg Phe Ser Gly
    50                  55                  60

Ser Gly Ser Gly Thr Asn Phe Ser Phe Lys Ile Ser Ser Leu Gln Ala
65                  70                  75                  80

Glu Asp Leu Ala Ser Tyr Tyr Cys Gln Gln Leu Tyr Ser Gly Pro Tyr
                85                  90                  95

Thr Phe Gly Gly Gly Thr Lys Leu Glu Ile Arg
```

-continued

```
                100                 105

<210> SEQ ID NO 11
<211> LENGTH: 119
<212> TYPE: PRT
<213> ORGANISM: Mus sp.

<400> SEQUENCE: 11

Gln Val Gln Leu Gln Gln Ser Gly Thr Glu Leu Leu Lys Pro Gly Ala
1               5                   10                  15

Ser Val Lys Leu Ser Cys Lys Ala Ser Gly Asn Thr Val Thr Ser Tyr
            20                  25                  30

Trp Met His Trp Val Lys Gln Arg Pro Gly Gln Gly Leu Glu Trp Ile
        35                  40                  45

Gly Glu Ile Leu Pro Ser Thr Gly Arg Thr Asn Tyr Asn Glu Asn Phe
    50                  55                  60

Lys Gly Lys Ala Met Leu Thr Val Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Thr Ile Val Tyr Phe Gly Asn Pro Trp Phe Ala Tyr Trp Gly Gln Gly
                100                 105                 110

Thr Leu Val Thr Val Ser Ala
            115

<210> SEQ ID NO 12
<211> LENGTH: 125
<212> TYPE: PRT
<213> ORGANISM: Mus sp.

<400> SEQUENCE: 12

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asp Asn
            20                  25                  30

Tyr Met Asn Trp Val Arg Gln Ser His Gly Lys Ser Leu Glu Trp Ile
        35                  40                  45

Gly Arg Val Asn Pro Ser Asn Gly Asp Thr Lys Tyr Asn Gln Asn Phe
    50                  55                  60

Lys Gly Lys Ala Thr Leu Thr Val Asp Lys Ser Leu Ser Thr Ala Tyr
65                  70                  75                  80

Met Gln Leu Asn Gly Leu Thr Ser Glu Asp Ser Ala Val Tyr Tyr Cys
                85                  90                  95

Gly Arg Thr Lys Asn Phe Tyr Ser Ser Tyr Ser Tyr Asp Asp Ala Met
                100                 105                 110

Asp Tyr Trp Gly Gln Gly Thr Ser Val Thr Val Ser Ser
            115                 120                 125

<210> SEQ ID NO 13
<211> LENGTH: 124
<212> TYPE: PRT
<213> ORGANISM: Mus sp.

<400> SEQUENCE: 13

Glu Val Gln Leu Gln Gln Ser Gly Ala Glu Phe Val Arg Pro Gly Ala
1               5                   10                  15

Ser Val Lys Phe Ser Cys Thr Ala Ser Gly Phe Asn Ile Lys Asp Asp
            20                  25                  30
```

-continued

```
Tyr Ile His Trp Val Arg Gln Arg Pro Glu Gln Gly Leu Glu Trp Val
         35                  40                  45

Gly Arg Ile Asp Pro Ala Asn Gly Asn Thr Lys Tyr Ala Pro Lys Phe
     50                  55                  60

Gln Asp Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Lys Ser Phe Pro Asn Asn Tyr Tyr Ser Tyr Asp Asp Ala Phe Ala
             100                 105                 110

Tyr Trp Gly Gln Gly Thr Leu Val Thr Val Ser Ala
         115                 120
```

<210> SEQ ID NO 14
<211> LENGTH: 118
<212> TYPE: PRT
<213> ORGANISM: Mus sp.

<400> SEQUENCE: 14

```
Gln Val Gln Leu Lys Glu Ser Gly Pro Val Leu Val Ala Pro Ser Gln
 1               5                  10                  15

Ser Leu Ser Ile Thr Cys Thr Val Ser Gly Phe Ser Leu Thr Lys Phe
             20                  25                  30

Gly Val His Trp Ile Arg Gln Thr Pro Gly Lys Gly Leu Glu Trp Leu
         35                  40                  45

Gly Val Ile Trp Ala Gly Gly Pro Thr Asn Tyr Asn Ser Ala Leu Met
     50                  55                  60

Ser Arg Leu Thr Ile Ser Lys Asp Ile Ser Gln Ser Gln Val Phe Leu
 65                  70                  75                  80

Arg Ile Asp Ser Leu Gln Thr Asp Asp Thr Ala Met Tyr Tyr Cys Ala
                 85                  90                  95

Lys Gln Ile Tyr Tyr Ser Thr Leu Val Asp Tyr Trp Gly Gln Gly Thr
             100                 105                 110

Ser Val Thr Val Ser Ser
         115
```

<210> SEQ ID NO 15
<211> LENGTH: 120
<212> TYPE: PRT
<213> ORGANISM: Mus sp.

<400> SEQUENCE: 15

```
Gln Val Gln Leu Lys Glu Ser Gly Pro Gly Leu Val Ala Pro Ser Gln
 1               5                  10                  15

Ser Leu Phe Ile Thr Cys Thr Val Ser Gly Phe Ser Leu Ser Ser Tyr
             20                  25                  30

Glu Ile Asn Trp Val Arg Gln Val Pro Gly Lys Gly Leu Glu Trp Leu
         35                  40                  45

Gly Val Ile Trp Thr Gly Ile Thr Asn Tyr Asn Ser Ala Leu Ile
     50                  55                  60

Ser Arg Leu Ser Ile Ser Lys Asp Asn Ser Lys Ser Val Phe Leu
 65                  70                  75                  80

Lys Met Asn Ser Leu Gln Thr Asp Asp Thr Ala Ile Tyr Tyr Cys Ala
                 85                  90                  95

Arg Gly Thr Gly Thr Gly Phe Tyr Tyr Ala Met Asp Tyr Trp Gly Gln
             100                 105                 110
```

```
Gly Thr Ser Val Thr Val Ser Ser
        115                 120

<210> SEQ ID NO 16
<211> LENGTH: 119
<212> TYPE: PRT
<213> ORGANISM: Mus sp.

<400> SEQUENCE: 16

Gln Val Gln Leu Gln Gln Pro Gly Ala Asp Phe Val Arg Pro Gly Ala
1               5                   10                  15

Ser Met Arg Leu Ser Cys Lys Ala Ser Gly Tyr Ser Phe Thr Ser Ser
            20                  25                  30

Trp Ile His Trp Val Lys Gln Arg Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Lys Ala Thr Leu Thr Val Asp Lys Ser Ser Thr Thr Ala Tyr
65                  70                  75                  80

Met Gln Leu Arg Ser Leu Thr Ser Ala Asp Ser Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ala
        115

<210> SEQ ID NO 17
<211> LENGTH: 119
<212> TYPE: PRT
<213> ORGANISM: Mus sp.

<400> SEQUENCE: 17

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val His Trp Val Arg Gln Phe Pro Gly Lys Gly Leu Glu Trp Leu
        35                  40                  45

Gly Val Ile Trp Ser Asp Gly Ser Thr Asp Phe Asn Ala Pro Phe Lys
    50                  55                  60

Ser Arg Leu Ser Ile Asn Lys Asp Asn Ser Lys Ser Gln Val Phe Phe
65                  70                  75                  80

Lys Met Asn Ser Leu Gln Ile Asp Asp Thr Ala Ile Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ala
        115

<210> SEQ ID NO 18
<211> LENGTH: 119
<212> TYPE: PRT
<213> ORGANISM: Mus sp.

<400> SEQUENCE: 18

Gln Val Gln Leu Lys Glu Ser Gly Pro Gly Leu Val Ala Pro Ser Gln
1               5                   10                  15
```

```
Ser Leu Ser Ile Thr Cys Thr Val Ser Gly Phe Ser Leu Thr Asn Tyr
            20                  25                  30

Ala Val His Trp Val Arg Gln Phe Pro Gly Lys Gly Leu Glu Trp Leu
            35                  40                  45

Gly Val Ile Trp Ser Asp Gly Ser Thr Asp Tyr Asn Ala Pro Phe Lys
 50                  55                  60

Ser Arg Leu Ser Ile Asn Lys Asp Asn Ser Lys Ser Gln Val Phe Phe
 65                  70                  75                  80

Lys Met Asn Ser Leu Gln Thr Asp Asp Thr Ala Ile Tyr Tyr Cys Ala
            85                  90                  95

Arg Lys Gly Gly Tyr Ser Gly Ser Trp Phe Ala Tyr Trp Gly Gln Gly
           100                 105                 110

Thr Leu Val Thr Val Ser Ala
           115

<210> SEQ ID NO 19
<211> LENGTH: 117
<212> TYPE: PRT
<213> ORGANISM: Mus sp.

<400> SEQUENCE: 19

Gln Val Gln Leu Lys Glu Ser Gly Pro Val Leu Val Ala Pro Ser Gln
 1               5                  10                  15

Ser Leu Ser Ile Thr Cys Thr Val Ser Gly Phe Ser Leu Thr Asn Tyr
            20                  25                  30

Gly Val His Trp Val Arg Gln Pro Pro Gly Lys Gly Leu Glu Trp Leu
            35                  40                  45

Gly Val Ile Trp Pro Val Gly Ser Thr Asn Tyr Asn Ser Ala Leu Met
 50                  55                  60

Ser Arg Leu Ser Ile His Lys Asp Asn Ser Lys Ser Gln Val Phe Leu
 65                  70                  75                  80

Arg Met Asn Ser Leu Gln Thr Asp Asp Thr Ala Ile Tyr Tyr Cys Ala
            85                  90                  95

Lys Met Asp Trp Asp Asp Phe Phe Asp Tyr Trp Gly Gln Gly Thr Thr
           100                 105                 110

Leu Thr Val Ser Ser
           115

<210> SEQ ID NO 20
<211> LENGTH: 124
<212> TYPE: PRT
<213> ORGANISM: Mus sp.

<400> SEQUENCE: 20

Glu Val Gln Leu Gln Gln Ser Gly Ala Glu Leu Val Arg Pro Gly Ala
 1               5                  10                  15

Ser Val Arg Leu Ser Cys Thr Ala Ser Gly Phe Asn Ile Lys Asp Asp
            20                  25                  30

Tyr Ile His Trp Val Arg Gln Arg Pro Lys Gln Gly Leu Glu Trp Leu
            35                  40                  45

Gly Arg Ile Asp Pro Ala Asn Gly Asn Thr Lys Tyr Asp Pro Arg Phe
 50                  55                  60

Gln Asp Lys Ala Thr Ile Thr Ala Asp Thr Ser Ser Asn Thr Ala Tyr
 65                  70                  75                  80

Leu His Leu Ser Ser Leu Thr Ser Glu Asp Thr Ala Val Tyr Tyr Cys
            85                  90                  95
```

Ala Lys Ser Phe Pro Asp Asn Tyr Tyr Ser Tyr Asp Asp Ala Phe Ala
            100                 105                 110

Tyr Trp Gly Gln Gly Thr Leu Val Thr Val Ser Ala
        115                 120

<210> SEQ ID NO 21
<211> LENGTH: 12
<212> TYPE: PRT
<213> ORGANISM: Mus sp.

<400> SEQUENCE: 21

Thr Ala Ser Ser Ser Val Ser Ser Ser Tyr Leu His
1               5                   10

<210> SEQ ID NO 22
<211> LENGTH: 11
<212> TYPE: PRT
<213> ORGANISM: Mus sp.

<400> SEQUENCE: 22

Leu Ala Ser Gln Thr Ile Gly Thr Trp Leu Ala
1               5                   10

<210> SEQ ID NO 23
<211> LENGTH: 11
<212> TYPE: PRT
<213> ORGANISM: Mus sp.

<400> SEQUENCE: 23

Leu Ala Ser Gln Thr Ile Gly Thr Trp Leu Gly
1               5                   10

<210> SEQ ID NO 24
<211> LENGTH: 16
<212> TYPE: PRT
<213> ORGANISM: Mus sp.

<400> SEQUENCE: 24

Arg Ser Ser Gln Asn Ile Val His Ser Asn Gly Asn Thr Tyr Leu Gln
1               5                   10                  15

<210> SEQ ID NO 25
<211> LENGTH: 11
<212> TYPE: PRT
<213> ORGANISM: Mus sp.

<400> SEQUENCE: 25

Arg Ala Ser Gln Asp Ile Tyr Lys Tyr Leu Asn
1               5                   10

<210> SEQ ID NO 26
<211> LENGTH: 12
<212> TYPE: PRT
<213> ORGANISM: Mus sp.

<400> SEQUENCE: 26

Thr Ala Ser Ser Ser Val Ser Ser Ser Tyr Phe His
1               5                   10

<210> SEQ ID NO 27
<211> LENGTH: 11
<212> TYPE: PRT
<213> ORGANISM: Mus sp.

<400> SEQUENCE: 27

```
Lys Ala Ser Gln Asp Val Gly Thr Asn Val Leu
1               5                   10

<210> SEQ ID NO 28
<211> LENGTH: 11
<212> TYPE: PRT
<213> ORGANISM: Mus sp.

<400> SEQUENCE: 28

Lys Ala Ser Gln Asn Val Gly Arg Ala Val Ala
1               5                   10

<210> SEQ ID NO 29
<211> LENGTH: 11
<212> TYPE: PRT
<213> ORGANISM: Mus sp.

<400> SEQUENCE: 29

Leu Ala Ser Gln Thr Ile Gly Thr Trp Leu Gly
1               5                   10

<210> SEQ ID NO 30
<211> LENGTH: 7
<212> TYPE: PRT
<213> ORGANISM: Mus sp.

<400> SEQUENCE: 30

Ser Thr Ser Asn Leu Ala Ser
1               5

<210> SEQ ID NO 31
<211> LENGTH: 7
<212> TYPE: PRT
<213> ORGANISM: Mus sp.

<400> SEQUENCE: 31

Ala Ala Thr Ser Leu Ala Asp
1               5

<210> SEQ ID NO 32
<211> LENGTH: 7
<212> TYPE: PRT
<213> ORGANISM: Mus sp.

<400> SEQUENCE: 32

Arg Ser Thr Thr Leu Ala Asp
1               5

<210> SEQ ID NO 33
<211> LENGTH: 7
<212> TYPE: PRT
<213> ORGANISM: Mus sp.

<400> SEQUENCE: 33

Lys Val Ser Asn Arg Phe Ser
1               5

<210> SEQ ID NO 34
<211> LENGTH: 7
<212> TYPE: PRT
<213> ORGANISM: Mus sp.

<400> SEQUENCE: 34

Tyr Thr Ser Gly Leu His Ser
```

```
1               5

<210> SEQ ID NO 35
<211> LENGTH: 7
<212> TYPE: PRT
<213> ORGANISM: Mus sp.

<400> SEQUENCE: 35

Arg Thr Ser Asn Leu Ala Ser
1               5

<210> SEQ ID NO 36
<211> LENGTH: 7
<212> TYPE: PRT
<213> ORGANISM: Mus sp.

<400> SEQUENCE: 36

Ser Ala Ser Tyr Arg His Ser
1               5

<210> SEQ ID NO 37
<211> LENGTH: 7
<212> TYPE: PRT
<213> ORGANISM: Mus sp.

<400> SEQUENCE: 37

Ser Ala Ser Asn Arg Tyr Thr
1               5

<210> SEQ ID NO 38
<211> LENGTH: 7
<212> TYPE: PRT
<213> ORGANISM: Mus sp.

<400> SEQUENCE: 38

Arg Ala Thr Ser Leu Ala Asp
1               5

<210> SEQ ID NO 39
<211> LENGTH: 9
<212> TYPE: PRT
<213> ORGANISM: Mus sp.

<400> SEQUENCE: 39

His Gln His His Arg Ser Pro Val Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Val Tyr Thr Thr Pro Leu Thr
1               5

<210> SEQ ID NO 41
<211> LENGTH: 9
<212> TYPE: PRT
<213> ORGANISM: Mus sp.

<400> SEQUENCE: 41
```

```
Gln Gln Leu Tyr Ser Ala Pro Tyr Thr
1               5

<210> SEQ ID NO 42
<211> LENGTH: 9
<212> TYPE: PRT
<213> ORGANISM: Mus sp.

<400> SEQUENCE: 42

Phe Gln Gly Ser His Val Pro Phe Thr
1               5

<210> SEQ ID NO 43
<211> LENGTH: 9
<212> TYPE: PRT
<213> ORGANISM: Mus sp.

<400> SEQUENCE: 43

Gln Gln Asp Ser Lys Phe Pro Trp Thr
1               5

<210> SEQ ID NO 44
<211> LENGTH: 9
<212> TYPE: PRT
<213> ORGANISM: Mus sp.

<400> SEQUENCE: 44

His Gln Phe His Arg Ser Pro Leu Thr
1               5

<210> SEQ ID NO 45
<211> LENGTH: 9
<212> TYPE: PRT
<213> ORGANISM: Mus sp.

<400> SEQUENCE: 45

Gln Gln Tyr Ser Arg Tyr Pro Leu Thr
1               5

<210> SEQ ID NO 46
<211> LENGTH: 9
<212> TYPE: PRT
<213> ORGANISM: Mus sp.

<400> SEQUENCE: 46

Gln Gln Tyr Ser Ser Tyr Pro Leu Thr
1               5

<210> SEQ ID NO 47
<211> LENGTH: 9
<212> TYPE: PRT
<213> ORGANISM: Mus sp.

<400> SEQUENCE: 47

Gln Gln Leu Tyr Ser Gly Pro Tyr Thr
1               5

<210> SEQ ID NO 48
<211> LENGTH: 10
<212> TYPE: PRT
<213> ORGANISM: Mus sp.

<400> SEQUENCE: 48

Gly Asn Thr Val Thr Ser Tyr Trp Met His
1               5                   10
```

<210> SEQ ID NO 49
<211> LENGTH: 10
<212> TYPE: PRT
<213> ORGANISM: Mus sp.

<400> SEQUENCE: 49

Gly Tyr Thr Phe Thr Asp Asn Tyr Met Asn
1               5                   10

<210> SEQ ID NO 50
<211> LENGTH: 10
<212> TYPE: PRT
<213> ORGANISM: Mus sp.

<400> SEQUENCE: 50

Gly Phe Asn Ile Lys Asp Asp Tyr Ile His
1               5                   10

<210> SEQ ID NO 51
<211> LENGTH: 10
<212> TYPE: PRT
<213> ORGANISM: Mus sp.

<400> SEQUENCE: 51

Gly Phe Ser Leu Thr Lys Phe Gly Val His
1               5                   10

<210> SEQ ID NO 52
<211> LENGTH: 10
<212> TYPE: PRT
<213> ORGANISM: Mus sp.

<400> SEQUENCE: 52

Gly Phe Ser Leu Ser Ser Tyr Glu Ile Asn
1               5                   10

<210> SEQ ID NO 53
<211> LENGTH: 10
<212> TYPE: PRT
<213> ORGANISM: Mus sp.

<400> SEQUENCE: 53

Gly Tyr Ser Phe Thr Ser Ser Trp Ile His
1               5                   10

<210> SEQ ID NO 54
<211> LENGTH: 10
<212> TYPE: PRT
<213> ORGANISM: Mus sp.

<400> SEQUENCE: 54

Gly Phe Ser Leu Thr Asn Tyr Ala Val His
1               5                   10

<210> SEQ ID NO 55
<211> LENGTH: 10
<212> TYPE: PRT
<213> ORGANISM: Mus sp.

<400> SEQUENCE: 55

Gly Phe Ser Leu Thr Asn Tyr Gly Val His
1               5                   10

```
<210> SEQ ID NO 56
<211> LENGTH: 10
<212> TYPE: PRT
<213> ORGANISM: Mus sp.

<400> SEQUENCE: 56

Gly Phe Asn Ile Lys Asp Asp Tyr Ile His
1               5                   10

<210> SEQ ID NO 57
<211> LENGTH: 17
<212> TYPE: PRT
<213> ORGANISM: Mus sp.

<400> SEQUENCE: 57

Glu Ile Leu Pro Ser Thr Gly Arg Thr Asn Tyr Asn Glu Asn Phe Lys
1               5                   10                  15

Gly

<210> SEQ ID NO 58
<211> LENGTH: 17
<212> TYPE: PRT
<213> ORGANISM: Mus sp.

<400> SEQUENCE: 58

Arg Val Asn Pro Ser Asn Gly Asp Thr Lys Tyr Asn Gln Asn Phe Lys
1               5                   10                  15

Gly

<210> SEQ ID NO 59
<211> LENGTH: 17
<212> TYPE: PRT
<213> ORGANISM: Mus sp.

<400> SEQUENCE: 59

Arg Ile Asp Pro Ala Asn Gly Asn Thr Lys Tyr Ala Pro Lys Phe Gln
1               5                   10                  15

Asp

<210> SEQ ID NO 60
<211> LENGTH: 16
<212> TYPE: PRT
<213> ORGANISM: Mus sp.

<400> SEQUENCE: 60

Val Ile Trp Ala Gly Gly Pro Thr Asn Tyr Asn Ser Ala Leu Met Ser
1               5                   10                  15

<210> SEQ ID NO 61
<211> LENGTH: 16
<212> TYPE: PRT
<213> ORGANISM: Mus sp.

<400> SEQUENCE: 61

Val Ile Trp Thr Gly Ile Thr Thr Asn Tyr Asn Ser Ala Leu Ile Ser
1               5                   10                  15

<210> SEQ ID NO 62
<211> LENGTH: 15
<212> TYPE: PRT
<213> ORGANISM: Mus sp.

<400> SEQUENCE: 62
```

Glu Ile Asn Pro Gly Asn Val Arg Thr Asn Tyr Asn Glu Asn Phe
1               5                   10                  15

<210> SEQ ID NO 63
<211> LENGTH: 16
<212> TYPE: PRT
<213> ORGANISM: Mus sp.

<400> SEQUENCE: 63

Val Ile Trp Ser Asp Gly Ser Thr Asp Phe Asn Ala Pro Phe Lys Ser
1               5                   10                  15

<210> SEQ ID NO 64
<211> LENGTH: 16
<212> TYPE: PRT
<213> ORGANISM: Mus sp.

<400> SEQUENCE: 64

Val Ile Trp Ser Asp Gly Ser Thr Asp Tyr Asn Ala Pro Phe Lys Ser
1               5                   10                  15

<210> SEQ ID NO 65
<211> LENGTH: 16
<212> TYPE: PRT
<213> ORGANISM: Mus sp.

<400> SEQUENCE: 65

Val Ile Trp Pro Val Gly Ser Thr Asn Tyr Asn Ser Ala Leu Met Ser
1               5                   10                  15

<210> SEQ ID NO 66
<211> LENGTH: 17
<212> TYPE: PRT
<213> ORGANISM: Mus sp.

<400> SEQUENCE: 66

Arg Ile Asp Pro Ala Asn Gly Asn Thr Lys Tyr Asp Pro Arg Phe Gln
1               5                   10                  15
Asp

<210> SEQ ID NO 67
<211> LENGTH: 10
<212> TYPE: PRT
<213> ORGANISM: Mus sp.

<400> SEQUENCE: 67

Val Tyr Phe Gly Asn Pro Trp Phe Ala Tyr
1               5                   10

<210> SEQ ID NO 68
<211> LENGTH: 16
<212> TYPE: PRT
<213> ORGANISM: Mus sp.

<400> SEQUENCE: 68

Thr Lys Asn Phe Tyr Ser Ser Tyr Ser Tyr Asp Asp Ala Met Asp Tyr
1               5                   10                  15

<210> SEQ ID NO 69
<211> LENGTH: 15
<212> TYPE: PRT
<213> ORGANISM: Mus sp.

<400> SEQUENCE: 69

```
Ser Phe Pro Asn Asn Tyr Tyr Ser Tyr Asp Asp Ala Phe Ala Tyr
1               5                   10                  15

<210> SEQ ID NO 70
<211> LENGTH: 10
<212> TYPE: PRT
<213> ORGANISM: Mus sp.

<400> SEQUENCE: 70

Gln Ile Tyr Tyr Ser Thr Leu Val Asp Tyr
1               5                   10

<210> SEQ ID NO 71
<211> LENGTH: 12
<212> TYPE: PRT
<213> ORGANISM: Mus sp.

<400> SEQUENCE: 71

Gly Thr Gly Thr Gly Phe Tyr Tyr Ala Met Asp Tyr
1               5                   10

<210> SEQ ID NO 72
<211> LENGTH: 10
<212> TYPE: PRT
<213> ORGANISM: Mus sp.

<400> SEQUENCE: 72

Val Phe Tyr Gly Glu Pro Tyr Phe Pro Tyr
1               5                   10

<210> SEQ ID NO 73
<211> LENGTH: 11
<212> TYPE: PRT
<213> ORGANISM: Mus sp.

<400> SEQUENCE: 73

Lys Gly Gly Tyr Ser Gly Ser Trp Phe Ala Tyr
1               5                   10

<210> SEQ ID NO 74
<211> LENGTH: 9
<212> TYPE: PRT
<213> ORGANISM: Mus sp.

<400> SEQUENCE: 74

Met Asp Trp Asp Asp Phe Phe Asp Tyr
1               5

<210> SEQ ID NO 75
<211> LENGTH: 15
<212> TYPE: PRT
<213> ORGANISM: Mus sp.

<400> SEQUENCE: 75

Ser Phe Pro Asp Asn Tyr Tyr Ser Tyr Asp Asp Ala Phe Ala Tyr
1               5                   10                  15

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76
```

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Leu
            35                  40                  45

Ile Tyr Arg Thr Ser Thr Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 77
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Leu
            35                  40                  45

Ile Tyr Arg Thr Ser Ile Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 78
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Trp
            35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 79
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 80
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Ala Gly Thr Lys Leu Glu Ile Lys
            100                 105

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 81

```
Gln Ile Val Leu Thr Gln Ser Pro Gly Thr Leu Ser Leu Ser Pro Gly
1               5                   10                  15

Glu Arg Val Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Gln Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105
```

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Lys Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys
            100                 105
```

<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser His Leu Ala Ser Gly Ile Pro Gly Arg Phe Ser
    50                  55                  60
```

-continued

Gly Ser Gly Ser Gly Thr Asp Phe Thr Leu Thr Ile Ser Arg Leu Glu
65                  70                  75                  80

Pro Glu Asp Ala Ala Val Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Phe Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 86

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Tyr Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 88
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile

```
                35                  40                  45
Gly Glu Ile Asn Pro Gly Asn Val Arg Thr Asn Tyr Asn Glu Asn Phe
            50                  55                  60
Arg Asn Arg Val Thr Met Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Thr Val Val Phe Tyr Gly Glu Pro Tyr Phe Pro Tyr Trp Gly Gln Gly
            100                 105                 110
Thr Leu Val Thr Val Ser Ser
        115

<210> SEQ ID NO 89
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Ser
            20                  25                  30
Trp Ile His Trp Val Lys Gln Ala Pro Gly Gln Gly Leu Glu Trp Met
        35                  40                  45
Gly Glu Ile Asn Pro Gly Asn Val Arg Thr Asn Tyr Asn Glu Asn Phe
    50                  55                  60
Arg Asn Lys Val Thr Met Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Thr Val Val Phe Tyr Gly Glu Pro Tyr Phe Pro Tyr Trp Gly Gln Gly
            100                 105                 110
Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Ser
            20                  25                  30
Trp Ile His Trp Val Arg Gln Arg Pro Gly Gln Gly Leu Glu Trp Met
        35                  40                  45
Gly Glu Ile Asn Pro Gly Asn Val Arg Thr Asn Tyr Asn Glu Asn Phe
    50                  55                  60
Arg Asn Arg Ala Thr Leu Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
```

```
                      85                  90                  95

Ala Val Val Phe Tyr Gly Glu Pro Tyr Phe Pro Tyr Trp Gly Gln Gly
                100                 105                 110

Thr Leu Val Thr Val Ser Ser
            115

<210> SEQ ID NO 91
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Met
            35                  40                  45

Gly Glu Ile Leu Pro Gly Val Val Arg Thr Asn Tyr Asn Glu Asn Phe
        50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
                100                 105                 110

Thr Leu Val Thr Val Ser Ser
            115

<210> SEQ ID NO 92
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Ile
            35                  40                  45

Gly Glu Ile Asn Pro Gly Ala Val Arg Thr Asn Tyr Asn Glu Asn Phe
        50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
                100                 105                 110

Thr Leu Val Thr Val Ser Ser
            115
```

```
<210> SEQ ID NO 93
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Ala Pro Gly Gln Gly Leu Glu Trp Ile
            35                  40                  45

Gly Glu Ile Asn Pro Gly Leu Val Arg Thr Asn Tyr Asn Glu Asn Phe
        50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 94
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Ala Pro Gly Gln Gly Leu Glu Trp Ile
            35                  40                  45

Gly Glu Ile Asn Pro Gly Ala Val Arg Thr Asn Tyr Asn Glu Asn Phe
        50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 95
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95
```

Gln Val Gln Leu Val Gln Ser Gly Ala Glu Val Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ser Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Asn Lys Asp Thr Ser Lys Ser Gln Val Ser Phe
65                  70                  75                  80

Lys Met Ser Ser Val Gln Ala Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
            50                  55                  60

Ser Arg Val Thr Ile Ser Lys Asp Thr Ser Lys Asn Gln Val Ser Leu
65                  70                  75                  80

Lys Met Asn Ser Leu Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser
            115

<210> SEQ ID NO 98
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
                20                  25                  30

Ala Val His Trp Ile Arg Gln Pro Pro Gly Lys Gly Leu Glu Trp Ile
            35                  40                  45

Gly Val Ile Trp Ser Asp Gly Ser Thr Asp Tyr Asn Ala Pro Phe Lys
            50                  55                  60

Ser Arg Val Thr Ile Ser Lys Asp Asn Ser Lys Ser Gln Val Ser Leu
65                  70                  75                  80

Lys Met Asn Ser Val Thr Val Ala Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser
            115

<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
                20                  25                  30

Ala Val His Trp Val Arg Gln Pro Pro Gly Lys Gly Leu Glu Trp Ile
            35                  40                  45

Gly Val Ile Trp Ser Asp Gly Ser Thr Asp Tyr Asn Ala Pro Phe Lys
            50                  55                  60

Ser Arg Val Thr Ile Ser Lys Asp Thr Ser Asn Gln Val Ser Phe
65                  70                  75                  80

Lys Leu Ser Ser Val Thr Val Asp Asp Thr Ala Val Tyr Tyr Cys Ala
                85                  90                  95

-continued

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 100
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
            20                  25                  30

Ala Val His Trp Ile Arg Gln Phe Pro Gly Lys Gly Leu Glu Trp Ile
        35                  40                  45

Gly Val Ile Trp Ser Asp Gly Ser Thr Asp Phe Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Phe
65                  70                  75                  80

Lys Met Ser Ser Val Thr Ala Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 102

<211> LENGTH: 7
<212> TYPE: PRT
<213> ORGANISM: Mus sp.

<400> SEQUENCE: 102

Arg Thr Ser Thr Leu Ala Ser
1               5

<210> SEQ ID NO 103
<211> LENGTH: 7
<212> TYPE: PRT
<213> ORGANISM: Mus sp.

<400> SEQUENCE: 103

Arg Thr Ser Ile Leu Ala Ser
1               5

<210> SEQ ID NO 104
<211> LENGTH: 7
<212> TYPE: PRT
<213> ORGANISM: Mus sp.

<400> SEQUENCE: 104

Arg Thr Ser Arg Leu Ala Ser
1               5

<210> SEQ ID NO 105
<211> LENGTH: 7
<212> TYPE: PRT
<213> ORGANISM: Mus sp.

<400> SEQUENCE: 105

Arg Thr Ser Gln Leu Ala Ser
1               5

<210> SEQ ID NO 106
<211> LENGTH: 7
<212> TYPE: PRT
<213> ORGANISM: Mus sp.

<400> SEQUENCE: 106

Arg Thr Ser Lys Leu Ala Ser
1               5

<210> SEQ ID NO 107
<211> LENGTH: 10
<212> TYPE: PRT
<213> ORGANISM: Mus sp.

<400> SEQUENCE: 107

Gly Phe Ser Leu Thr Asp Tyr Ala Val His
1               5                   10

<210> SEQ ID NO 108
<211> LENGTH: 15
<212> TYPE: PRT
<213> ORGANISM: Mus sp.

<400> SEQUENCE: 108

Glu Ile Leu Pro Gly Val Val Arg Thr Asn Tyr Asn Glu Asn Phe
1               5                   10                  15

<210> SEQ ID NO 109
<211> LENGTH: 15
<212> TYPE: PRT

<213> ORGANISM: Mus sp.

<400> SEQUENCE: 109

Glu Ile Asn Pro Gly Ala Val Arg Thr Asn Tyr Asn Glu Asn Phe
1               5                   10                  15

<210> SEQ ID NO 110
<211> LENGTH: 15
<212> TYPE: PRT
<213> ORGANISM: Mus sp.

<400> SEQUENCE: 110

Glu Ile Asn Pro Gly Leu Val Arg Thr Asn Tyr Asn Glu Asn Phe
1               5                   10                  15

<210> SEQ ID NO 111
<211> LENGTH: 15
<212> TYPE: PRT
<213> ORGANISM: Mus sp.

<400> SEQUENCE: 111

Glu Ile Asn Pro Gly Ser Val Arg Thr Asn Tyr Asn Glu Asn Phe
1               5                   10                  15

<210> SEQ ID NO 112
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 114
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Thr Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 115
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Ile Leu Ala Ser Gly Val Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

```
Ser Phe Asn Arg Gly Glu Cys
    210                 215

<210> SEQ ID NO 116
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 117
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Arg Leu Ala Ser Gly Val Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 118
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Ala Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys

-continued

```
                195                 200                 205
Ser Phe Asn Arg Gly Glu Cys
    210                 215

<210> SEQ ID NO 119
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Ile Val Leu Thr Gln Ser Pro Gly Thr Leu Ser Leu Ser Pro Gly
1               5                   10                  15

Glu Arg Val Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Gln Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 120
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Lys Leu Ala Ser Gly Val Pro Asp Arg Phe Ser
```

```
                  50                  55                  60
Gly Ser Gly Ser Gly Thr Asp Phe Thr Leu Thr Ile Ser Arg Leu Glu
 65                  70                  75                  80

Pro Glu Asp Phe Ala Thr Tyr Tyr Cys His Gln Phe His Arg Ser Pro
                 85                  90                  95

Leu Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 121
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Ile Val Leu Thr Gln Ser Pro Gly Thr Leu Ser Leu Ser Pro Gly
  1               5                  10                  15

Glu Arg Ala Thr Met Ser Cys Thr Ala Ser Ser Ser Val Ser Ser Ser
                 20                  25                  30

Tyr Phe His Trp Tyr Gln Gln Lys Pro Gly Gln Ala Pro Arg Leu Leu
                 35                  40                  45

Ile Tyr Arg Thr Ser His Leu Ala Ser Gly Ile Pro Gly Arg Phe Ser
             50                  55                  60

Gly Ser Gly Ser Gly Thr Asp Phe Thr Leu Thr Ile Ser Arg Leu Glu
 65                  70                  75                  80

Pro Glu Asp Ala Ala Val Tyr Tyr Cys His Gln Phe His Arg Ser Pro
                 85                  90                  95

Leu Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190
```

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Phe Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 123
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

```
Tyr Ser Ala Ser Tyr Arg His Ser Gly Ile Pro Asp Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ser Arg Tyr Pro Leu
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 124
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Glu Ile Val Met Thr Gln Ser Pro Ala Thr Leu Ser Val Ser Pro Gly
 1               5                  10                  15

Val Arg Ala Thr Leu Ser Cys Lys Ala Ser Gln Asp Val Gly Thr Asn
                 20                  25                  30

Val Leu Trp Tyr Gln Gln Lys Pro Gly Gln Ala Pro Arg Pro Leu Ile
             35                  40                  45

Tyr Ser Ala Ser Tyr Arg His Ser Gly Ile Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Glu Tyr Tyr Cys Gln Gln Tyr Ser Arg Tyr Pro Leu
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 125
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                    325                 330                 335
Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 126
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Ile
            35                  40                  45

Gly Glu Ile Asn Pro Gly Asn Val Arg Thr Asn Tyr Asn Glu Asn Phe
        50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
```

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
            245                 250                 255

Pro Glu Val Lys Phe Asn Trp Tyr Val Asp Gly Val Glu Val His Asn
        260                 265                 270

Ala Lys Thr Lys Pro Arg Glu Glu Gln Tyr Asn Ser Thr Tyr Arg Val
    275                 280                 285

Val Ser Val Leu Thr Val Leu His Gln Asp Trp Leu Asn Gly Lys Glu
290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Tyr Thr
            325                 330                 335

Leu Pro Pro Ser Arg Glu Glu Met Thr Lys Asn Gln Val Ser Leu Thr
        340                 345                 350

Cys Leu Val Lys Gly Phe Tyr Pro Ser Asp Ile Ala Val Glu Trp Glu
    355                 360                 365

Ser Asn Gly Gln Pro Glu Asn Asn Tyr Lys Thr Thr Pro Pro Val Leu
370                 375                 380

Asp Ser Asp Gly Ser Phe Phe Leu Tyr Ser Lys Leu Thr Val Asp Lys
            385                 390                 395                 400

Ser Arg Trp Gln Gln Gly Asn Val Phe Ser Cys Ser Val Met His Glu
        405                 410                 415

Ala Leu His Asn His Tyr Thr Gln Lys Ser Leu Ser Leu Ser Pro Gly
    420                 425                 430

Lys
        435                 440                 445

<210> SEQ ID NO 127
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Thr Val Val Phe Tyr Gly Glu Pro Tyr Phe Pro Tyr Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu

```
                    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 128
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
```

```
                35                  40                  45
Gly Glu Ile Asn Pro Gly Asn Val Arg Thr Asn Tyr Asn Glu Asn Phe
 50                  55                  60

Arg Asn Arg Ala Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 129
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Leu Pro Gly Val Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 130
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Ile
            35                  40                  45

Gly Glu Ile Asn Pro Gly Ala Val Arg Thr Asn Tyr Asn Glu Asn Phe
        50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 131
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Leu Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 132
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ala Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80
```

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 133
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ser Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 134
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Asn Lys Asp Thr Ser Lys Ser Gln Val Ser Phe
65                  70                  75                  80

Lys Met Ser Ser Val Gln Ala Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 135
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Leu
65                  70                  75                  80

Lys Met Asn Ser Leu Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 136
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Leu
65                  70                  75                  80

Lys Met Asn Ser Val Thr Val Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 137
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Glu Ser Gly Pro Gly Leu Val Lys Pro Ser Glu
1               5                   10                  15
```

```
Thr Leu Ser Ile Thr Cys Thr Val Ser Gly Phe Ser Leu Thr Asp Tyr
             20                  25                  30

Ala Val His Trp Val Arg Gln Pro Pro Gly Lys Gly Leu Glu Trp Ile
         35                  40                  45

Gly Val Ile Trp Ser Asp Gly Ser Thr Asp Tyr Asn Ala Pro Phe Lys
     50                  55                  60

Ser Arg Val Thr Ile Ser Lys Asp Thr Ser Lys Asn Gln Val Ser Phe
 65                  70                  75                  80

Lys Leu Ser Ser Val Thr Val Asp Asp Thr Ala Val Tyr Tyr Cys Ala
                 85                  90                  95

Arg Lys Gly Gly Tyr Ser Gly Ser Trp Phe Ala Tyr Trp Gly Gln Gly
             100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
             130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
             195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
             275                 280                 285

Ala Lys Thr Lys Pro Arg Glu Glu Gln Tyr Asn Ser Thr Tyr Arg Val
         290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
             325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
             355                 360                 365

Cys Leu Val Lys Gly Phe Tyr Pro Ser Asp Ile Ala Val Glu Trp Glu
             370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
```

Lys

<210> SEQ ID NO 138
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

```
Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
            20                  25                  30

Ala Val His Trp Ile Arg Gln Phe Pro Gly Lys Gly Leu Glu Trp Ile
        35                  40                  45

Gly Val Ile Trp Ser Asp Gly Ser Thr Asp Phe Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
                340                 345                 350
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 139
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Phe
65                  70                  75                  80

Lys Met Ser Ser Val Thr Ala Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
```

```
            245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 140
<211> LENGTH: 7
<212> TYPE: PRT
<213> ORGANISM: Mus sp.

<400> SEQUENCE: 140

Arg Thr Ser His Leu Ala Ser
1               5
```

ANTI IL-36R ANTIBODIES

SEQUENCE LISTING

The instant application contains a Sequence Listing which has been submitted in ASCII format via EFS-Web and is hereby incorporated by reference in its entirety. Said ASCII copy, created on Nov. 12, 2012, is named 09-0583US.txt and is 146,203 bytes in size.

TECHNICAL FIELD OF THE INVENTION

This invention generally relates to anti-IL-36R antibodies for diagnostic and therapeutic use. The antibodies can be used in pharmaceutical compositions and kits comprising such compounds. The antibodies are useful in methods for the treatment of various diseases or disorders, for example immunological, inflammatory, autoimmune, fibrotic and respiratory diseases in humans.

BACKGROUND OF THE INVENTION

The IL-1 family of cytokines is composed of 11 different ligands, namely, IL-1α (also termed IL-1F1), IL-1β (IL-1F2), IL-1 receptor antagonist (IL-1Ra or IL-1F3), IL-18 (IL-1F4), IL-1F5 to IL-1F10, and IL-1F11 (or IL-33). IL-1α and IL-1β are known to induce pro-inflammatory activities on binding to type I IL-1 receptor (IL-1RI) and recruitment of the common co-receptor IL-1 receptor accessory protein (IL-1RAcP), whereas IL-1Ra acts as a competitive inhibitor of IL-1 binding to IL-1RI, thus exerting anti-inflammatory activity. Numerous studies reported that IL-18 is a pro-inflammatory cytokine that is an inducer of IFN-γ, whereas IL-33 was described as an immunoregulatory cytokine involved in particular in the control of Th2 responses. New members of the IL-1 family, including IL-1F5, IL-1F6, IL-1F8, and IL-1F9, were identified through searches in DNA databases for homologs of IL-1. In humans and mice, all the genes encoding these cytokines map to less than 300 kb of chromosome 2q, where they are flanked by the IL1A, IL1B, and IL1RN genes. IL-1F6, IL-1F8, and IL-1F9 share 21% to 37% amino acid sequence homology with IL-1 and IL-1Ra, whereas IL-1F5 displays 52% amino acid sequence homology with IL-1Ra, suggesting that IL-1F5 might represent an endogenous receptor antagonist.

IL-1F6, IL-1F8, and IL-1F9 bind to IL-1Rrp2, a receptor of the IL-1R family, and use IL-1RAcP as a co-receptor to stimulate intracellular signals similar to those induced by IL-1, whereas IL-1F5 was shown to inhibit IL-1F9-induced NF-κB activation in Jurkat T cells that over-express IL-1Rrp2. Like IL-1β, all these IL-1 homologs lack a leader peptide and cannot be released through the conventional secretory pathway, although studies suggest that release of IL-1Rrp2 agonists may be controlled by mechanisms different from those regulating IL-1β secretion. To acknowledge the specific biologic effects of these cytokines and to recognize that they all bind to the same receptor, it has recently been proposed to amend the nomenclature of IL-1 homologs. Thus, IL-1Rrp2 is now termed IL-36R and its ligands are named IL-36α (IL-1F6), IL-36β (IL-1F8), and IL-36γ (IL-1F9). In addition, IL-1F5, which has been shown to exert receptor antagonist activities, has been renamed IL-36Ra.

Messenger RNAs for IL-36α, IL-36β, and IL-36γ are highly expressed in several tissues, particularly in internal epithelial tissues, which are exposed to pathogens and in skin. Interestingly, expression of IL-36Ra and IL-36α is significantly up-regulated in IL-1β/TNF-α-stimulated human keratinocytes, and IL-36Ra and IL-36γ mRNA are highly increased in lesional psoriasis skin. Moreover, IL-36γ protein production is enhanced in human keratinocytes after TNF-α and IFN-γ stimulation. Elevated IL-36α mRNA and protein expression was reported also in chronic kidney disease.

Transgenic mice overexpressing IL-36α in keratinocytes exhibit inflammatory skin lesions sharing some features with psoriasis. This phenotype was more severe when transgenic mice were crossed with IL-36Ra-deficient mice, supporting a regulatory function of IL-36Ra in vivo. The inflammatory skin condition in keratinocyte-specific IL-36a transgenic is even more similar to human psoriasis if the mice are treated with 12-O-tetradecanoylphorbol 13-acetate, resembling the human disease histologically, molecularly, and in its response to therapeutics. Moreover, human psoriatic lesional skin transplanted onto immunodeficient mice is normalized when the mice are treated with anti-IL-36R antibody, arguing that the IL-36 axis is required to maintain the lesional phenotype in human psoriatic skin. Taken together, these data indicate that IL-36R ligands, including IL-36α, IL-36β, and IL-36γ, exert proinflammatory effects in vitro and in vivo and that IL-36Ra acts as a natural antagonist, thus mimicking the IL-1/IL-1Ra system.

There is therefore evidence that IL-36R ligands are involved in a number of disease conditions, and there is a need for new therapeutic agents targeting this pathway, in particular for use in the treatment of inflammatory diseases.

SUMMARY OF THE INVENTION

The present invention addresses the above need by providing biotherapeutics, in particular antibodies, which bind to IL-36R. In one aspect, the antibodies of the present invention block IL36 ligand-mediated signaling (α, β and/or γ). In one aspect the antibodies of the present invention are useful, for example for the treatment of epithelial-mediated inflammation/fibrosis in diseases such as psoriasis, inflammatory bowel disease, scleroderma, COPD, and chronic kidney disease.

In one aspect, the present invention provides an anti-IL-36R antibody having one or more of the properties below.

In one aspect, an anti-IL-36R antibody of the present invention has high molecular/cellular binding potency. In one aspect, an anti-IL-36R antibody of the present invention binds to human IL-36R at a $K_D<0.1$ nM. In a further aspect, an anti-IL-36R antibody of the present invention, in particular a humanized anti-IL-36R antibody, binds to human IL-36R at a $K_D<50$ pM. In one aspect, an anti-IL-36R antibody of the present invention binds to IL-36R expressing cells at an $EC_{90}<5$ nM.

In another aspect, an anti-IL-36R antibody of the present invention has high cell-based functional blocking potency. In one aspect, an anti-IL-36R antibody of the present invention blocks all three IL-36R agonistic ligands (α, β, γ) at an $IC_{90} \le 5$ nM, in disease-relevant cell lines and primary cells.

In one aspect, an anti-IL-36R antibody of the present invention has the molecular/cellular binding potency and the cell-based functional blocking potency set forth above.

In a further aspect, an anti-IL-36R antibody of the present invention has high selectivity for example greater than 1000-fold selectivity against human IL-1R1 or IL-36R negative cell lines. In a further aspect, an anti-IL-36R antibody of the present invention does not bind to human IL-1R1 or IL-36R negative cell lines.

In embodiment one, the present invention provides an anti-IL-36R antibody or antigen-binding fragment thereof, which binds to human IL-36R at a $K_D$ equal to or <0.1 nM.

In embodiment two, the present invention provides an anti-IL-36R antibody or antigen-binding fragment thereof according to embodiment one, wherein the said antibody or antigen-binding fragment is a monoclonal antibody or antigen-binding fragment thereof.

In embodiment three, the present invention provides an anti-IL-36R antibody or antigen-binding fragment thereof according to embodiment one or two, wherein the said antibody or antigen-binding fragment is a humanized antibody or antigen-binding fragment thereof.

In embodiment four, the present invention provides an anti-IL-36R antibody or antigen-binding fragment thereof according to embodiment three, which binds to human IL-36R at a $K_D$ equal to or <50 pM.

In embodiment five, the present invention provides an anti-IL-36R antibody or antigen-binding fragment thereof according to any one of embodiment one to four, which does not bind to human IL-1R1.

In embodiment six, the present invention provides an anti-IL-36R antibody or antigen-binding fragment thereof according to embodiment one, wherein the antibody or antigen-binding fragment thereof comprises:
a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In embodiment seven, the present invention provides an anti-IL-36R antibody or antigen-binding fragment thereof according to embodiment six, wherein the antibody or antigen-binding fragment thereof comprises:
a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In embodiment eight, the present invention provides an anti-IL-36R antibody or antigen-binding fragment thereof according to embodiment six, wherein the antibody or antigen-binding fragment thereof comprises:
a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In embodiment nine, the present invention provides an anti-IL-36R antibody or antigen-binding fragment thereof according to embodiment six, wherein the antibody or antigen-binding fragment thereof comprises:
a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In embodiment ten, the present invention provides an anti-IL-36R antibody or antigen-binding fragment thereof according to embodiment six, wherein the antibody or antigen-binding fragment thereof comprises:
a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In embodiment eleven, the present invention provides an anti-IL-36R antibody or antigen-binding fragment thereof according to embodiment six, wherein the antibody or antigen-binding fragment thereof comprises:
a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In embodiment twelve, the present invention provides an anti-IL-36R antibody or antigen-binding fragment thereof according to embodiment six, wherein the antibody or antigen-binding fragment thereof comprises:
a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In embodiment thirteen, the present invention provides an anti-IL-36R antibody or antigen-binding fragment thereof according to embodiment one, wherein the antibody or antigen-binding fragment thereof comprises a light chain variable region comprising the amino acid sequence of any one of SEQ ID NO: 76, 77, 78, 79, 80, 81, 82 or 83; and a heavy chain variable region comprising the amino acid sequence of any one of SEQ ID NO: 87, 88, 89, 90, 91, 92, 93, 94 or 95.

In embodiment fourteen, the present invention provides an anti-IL-36R antibody or antigen-binding fragment thereof according to embodiment thirteen, wherein the antibody or antigen-binding fragment thereof comprises a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 77;
and a heavy chain variable region comprising the amino acid sequence of SEQ ID NO: 88; or a light chain variable region comprising the amino acid sequence of SEQ ID NO: 77; and a heavy chain variable region comprising the amino acid sequence of SEQ ID NO: 89.

In embodiment fifteen, the present invention provides an in the antibody or antigen-binding fragment thereof comprises a light chain variable region comprising the amino acid sequence of SEQ ID NO: 80; and a heavy chain variable region comprising the amino acid sequence of SEQ ID NO: 87; or
a light chain variable region comprising the amino acid sequence of SEQ ID NO: 80;
and a heavy chain variable region comprising the amino acid sequence of SEQ ID NO: 88; or
a light chain variable region comprising the amino acid sequence of SEQ ID NO: 80; and a heavy chain variable region comprising the amino acid sequence of SEQ ID NO: 89.

In embodiment sixteen, the present invention provides an anti-IL-36R antibody or antigen-binding fragment thereof according to embodiment one, wherein the antibody or antigen-binding fragment thereof comprises:
a light chain variable region comprising the amino acid sequence of SEQ ID NO: 27 (L-CDR1); the amino acid sequence of SEQ ID NO: 36 (L-CDR2); the amino acid sequence of SEQ ID NO: 45 (L-CDR3); and a heavy chain variable region comprising the amino acid sequence of SEQ ID NO: 107 (H-CDR1); the amino acid sequence of SEQ ID NO: 63 (H-CDR2); the amino acid sequence of SEQ ID NO: 73 (H-CDR3); or
a light chain variable region comprising the amino acid sequence of SEQ ID NO: 27 (L-CDR1); the amino acid sequence of SEQ ID NO: 36 (L-CDR2); the amino acid sequence of SEQ ID NO: 45 (L-CDR3); and a heavy chain variable region comprising the amino acid sequence of SEQ ID NO: 107 (H-CDR1); the amino acid sequence of SEQ ID NO: 64 (H-CDR2); the amino acid sequence of SEQ ID NO: 73 (H-CDR3); or
a light chain variable region comprising the amino acid sequence of SEQ ID NO: 27 (L-CDR1); the amino acid sequence of SEQ ID NO: 36 (L-CDR2); the amino acid sequence of SEQ ID NO: 45 (L-CDR3); and a heavy chain variable region comprising the amino acid sequence of SEQ ID NO: 54 (H-CDR1); the amino acid sequence of SEQ ID NO: 63 or 64 (H-CDR2); the amino acid sequence of SEQ ID NO: 73 (H-CDR3).

In embodiment seventeen, the present invention provides an anti-IL-36R antibody or antigen-binding fragment thereof according to embodiment one, wherein the antibody or antigen-binding fragment thereof comprises a light chain variable region comprising the amino acid sequence of any one of SEQ ID NO: 84, 85 or 86; and a heavy chain variable region comprising the amino acid sequence of any one of SEQ ID NO: 96, 97, 98, 99, 100 or 101.

In embodiment eighteen, the present invention provides an anti-IL-36R antibody or antigen-binding fragment thereof according to embodiment seventeen, wherein the antibody or antigen-binding fragment thereof comprises a light chain variable region comprising the amino acid sequence of SEQ ID NO: 85; and a heavy chain variable region comprising the amino acid sequence of SEQ ID NO: 100; or a light chain variable region comprising the amino acid sequence of SEQ ID NO: 85; and a heavy chain variable region comprising the amino acid sequence of SEQ ID NO:101.

In embodiment nineteen, the present invention provides an anti-IL-36R antibody or antigen-binding fragment thereof according to embodiment seventeen, wherein the antibody or antigen-binding fragment thereof comprises a light chain variable region comprising the amino acid sequence of SEQ ID NO: 86; and a heavy chain variable region comprising the amino acid sequence of SEQ ID NO: 100; or a light chain variable region comprising the amino acid sequence of SEQ ID NO: 86; and a heavy chain variable region comprising the amino acid sequence of SEQ ID NO:101.

In embodiment twenty, the present invention provides an anti-IL-36R antibody, wherein the antibody comprises a light chain comprising the amino acid sequence of any one of SEQ ID NO: 114, 115, 116, 117, 118, 119, 120 or 121; and a heavy chain comprising the amino acid sequence of any one of SEQ ID NO: 125, 126, 127, 128, 129, 130, 131, 132 or 133.

In embodiment twenty one, the present invention provides an anti-IL-36R antibody according to embodiment twenty, wherein the antibody comprises a light chain comprising the amino acid sequence of SEQ ID NO: 115; and a heavy chain comprising the amino acid sequence of SEQ ID NO: 125.

In embodiment twenty two, the present invention provides an anti-IL-36R antibody according to embodiment twenty, wherein the antibody comprises a light chain comprising the amino acid sequence of SEQ ID NO: 115; and a heavy chain comprising the amino acid sequence of SEQ ID NO: 126.

In embodiment twenty three, the present invention provides an anti-IL-36R antibody according to embodiment twenty, wherein the antibody comprises a light chain comprising the amino acid sequence of SEQ ID NO: 115; and a heavy chain comprising the amino acid sequence of SEQ ID NO: 127.

In embodiment twenty four, the present invention provides an anti-IL-36R antibody according to embodiment twenty, wherein the antibody comprises a light chain comprising the amino acid sequence of SEQ ID NO: 118; and a heavy chain comprising the amino acid sequence of SEQ ID NO: 125.

In embodiment twenty five, the present invention provides an anti-IL-36R antibody according to embodiment twenty, wherein the antibody comprises a light chain comprising the amino acid sequence of SEQ ID NO: 118; and a heavy chain comprising the amino acid sequence of SEQ ID NO: 126.

In embodiment twenty six, the present invention provides an anti-IL-36R antibody according to embodiment twenty, wherein the antibody comprises a light chain comprising the amino acid sequence of SEQ ID NO: 118; and a heavy chain comprising the amino acid sequence of SEQ ID NO: 127.

In embodiment twenty seven, the present invention provides an anti-IL-36R antibody, wherein the antibody comprises a light chain comprising the amino acid sequence of any one of SEQ ID NO: 122, 123 or 124; and a heavy chain comprising the amino acid sequence of any one of SEQ ID NO: 134, 135, 136, 137, 138 or 139.

In embodiment twenty eight, the present invention provides an anti-IL-36R antibody according to embodiment twenty seven, wherein the antibody comprises a light chain comprising the amino acid sequence of SEQ ID NO: 123; and a heavy chain comprising the amino acid sequence of SEQ ID NO: 138.

In embodiment twenty nine, the present invention provides an anti-IL-36R antibody according to embodiment twenty seven, wherein the antibody comprises a light chain comprising the amino acid sequence of SEQ ID NO: 123; and a heavy chain comprising the amino acid sequence of SEQ ID NO: 139.

In embodiment thirty, the present invention provides an anti-IL-36R antibody according to twenty seven, wherein the antibody comprises a light chain comprising the amino acid sequence of SEQ ID NO: 124; and a heavy chain comprising the amino acid sequence of SEQ ID NO: 138.

In embodiment thirty one, the present invention provides an anti-IL-36R antibody or antigen-binding fragment thereof according to embodiment one, wherein the antibody or antigen-binding fragment thereof comprises:
a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62 (H-CDR2); the amino acid sequence of SEQ ID NO: 72 (H-CDR3).

In embodiment thirty two, the present invention provides an anti-IL-36R antibody or antigen-binding fragment thereof according to embodiment one, wherein the antibody or antigen-binding fragment thereof comprises:
a) a light chain variable region comprising the amino acid sequence of SEQ ID NO: 26 (L-CDR1); the amino acid sequence of SEQ ID NO: 104(L-CDR2); the amino acid sequence of SEQ ID NO: 44 (L-CDR3); and
b) a heavy chain variable region comprising the amino acid sequence of SEQ ID NO: 53 (H-CDR1); the amino acid sequence of SEQ ID NO: 62 (H-CDR2); the amino acid sequence of SEQ ID NO: 72 (H-CDR3).

In embodiment thirty three, the present invention provides an anti-IL-36R antibody or antigen-binding fragment thereof according to embodiment one, wherein the antibody or antigen-binding fragment thereof comprises:
a) a light chain variable region comprising the amino acid sequence of SEQ ID NO: 27 (L-CDR1); the amino acid sequence of SEQ ID NO: 36(L-CDR2); the amino acid sequence of SEQ ID NO: 45 (L-CDR3); and
b) a heavy chain variable region comprising the amino acid sequence of SEQ ID NO: 107 (H-CDR1); the amino acid sequence of SEQ ID NO: 63 (H-CDR2); the amino acid sequence of SEQ ID NO: 73 (H-CDR3).

In embodiment thirty four, the present invention provides an anti-IL-36R antibody or antigen-binding fragment thereof according to embodiment one, wherein the antibody or antigen-binding fragment thereof comprises:
a) a light chain variable region comprising the amino acid sequence of SEQ ID NO: 27 (L-CDR1); the amino acid sequence of SEQ ID NO: 36(L-CDR2); the amino acid sequence of SEQ ID NO: 45 (L-CDR3); and
b) a heavy chain variable region comprising the amino acid sequence of SEQ ID NO: 107 (H-CDR1); the amino acid sequence of SEQ ID NO: 64 (H-CDR2); the amino acid sequence of SEQ ID NO: 73 (H-CDR3).

In one embodiment, an antibody or antigen-binding fragment thereof according to any one of embodiments one to thirty-four is a monoclonal antibody. In one embodiment, an antibody or antigen-binding fragment thereof according to any one of embodiments one to thirty-four is a humanized antibody. In one embodiment, an antibody or antigen-binding fragment thereof according to any one of embodiments one to thirty-four is a monoclonal humanized antibody.

In embodiment thirty five, the present invention provides an anti-IL-36R antibody or antigen-binding fragment thereof, wherein the antibody or antigen-binding fragment fragment thereof comprises:
a light chain variable region comprising the amino acid sequence of SEQ ID NO: 21 (L-CDR1); the amino acid sequence of SEQ ID NO: 30 (L-CDR2); the amino acid sequence of SEQ ID NO: 39 (L-CDR3); and a heavy chain variable region comprising the amino acid sequence of SEQ ID NO: 48 (H-CDR1); the amino acid sequence of SEQ ID NO: 57 (H-CDR2); the amino acid sequence of SEQ ID NO: 67 (H-CDR3); or
a light chain variable region comprising the amino acid sequence of SEQ ID NO: 22 (L-CDR1); the amino acid sequence of SEQ ID NO: 31 (L-CDR2); the amino acid sequence of SEQ ID NO: 40 (L-CDR3); and a heavy chain variable region comprising the amino acid sequence of SEQ ID NO: 49 (H-CDR1); the amino acid sequence of SEQ ID NO: 58 (H-CDR2); the amino acid sequence of SEQ ID NO: 68 (H-CDR3); or
a light chain variable region comprising the amino acid sequence of SEQ ID NO: 23 (L-CDR1); the amino acid sequence of SEQ ID NO: 32 (L-CDR2); the amino acid sequence of SEQ ID NO: 41 (L-CDR3); and a heavy chain variable region comprising the amino acid sequence of SEQ ID NO: 50 (H-CDR1); the amino acid sequence of SEQ ID NO: 59 (H-CDR2); the amino acid sequence of SEQ ID NO: 69 (H-CDR3); or
a light chain variable region comprising the amino acid sequence of SEQ ID NO: 24 (L-CDR1); the amino acid sequence of SEQ ID NO: 33 (L-CDR2); the amino acid sequence of SEQ ID NO: 42 (L-CDR3); and a heavy chain variable region comprising the amino acid sequence of SEQ ID NO: 51 (H-CDR1); the amino acid sequence of SEQ ID NO: 60 (H-CDR2); the amino acid sequence of SEQ ID NO: 70 (H-CDR3); or
a light chain variable region comprising the amino acid sequence of SEQ ID NO: 25 (L-CDR1); the amino acid sequence of SEQ ID NO: 34 (L-CDR2); the amino acid sequence of SEQ ID NO: 43 (L-CDR3); and a heavy chain variable region comprising the amino acid sequence of SEQ ID NO: 52 (H-CDR1); the amino acid sequence of SEQ ID NO: 61 (H-CDR2); the amino acid sequence of SEQ ID NO: 71 (H-CDR3); or
a light chain variable region comprising the amino acid sequence of SEQ ID NO: 26 (L-CDR1); the amino acid sequence of SEQ ID NO: 35 (L-CDR2); the amino acid sequence of SEQ ID NO: 44 (L-CDR3); and a heavy chain variable region comprising the amino acid sequence of SEQ ID NO: 53 (H-CDR1); the amino acid sequence of SEQ ID NO: 62 (H-CDR2); the amino acid sequence of SEQ ID NO: 72 (H-CDR3); or
a light chain variable region comprising the amino acid sequence of SEQ ID NO: 27 (L-CDR1); the amino acid sequence of SEQ ID NO: 36 (L-CDR2); the amino acid sequence of SEQ ID NO: 45 (L-CDR3); and a heavy chain variable region comprising the amino acid sequence of SEQ ID NO: 54 (H-CDR1); the amino acid sequence of SEQ ID NO: 63 (H-CDR2); the amino acid sequence of SEQ ID NO: 73 (H-CDR3); or
a light chain variable region comprising the amino acid sequence of SEQ ID NO: 27 (L-CDR1); the amino acid sequence of SEQ ID NO: 36 (L-CDR2); the amino acid sequence of SEQ ID NO: 45 (L-CDR3); and a heavy chain variable region comprising the amino acid sequence of SEQ ID NO: 54 (H-CDR1); the amino acid sequence of SEQ ID NO: 64 (H-CDR2); the amino acid sequence of SEQ ID NO:

73 (H-CDR3); or a light chain variable region comprising the amino acid sequence of SEQ ID NO: 28 (L-CDR1); the amino acid sequence of SEQ ID NO: 37 (L-CDR2); the amino acid sequence of SEQ ID NO: 46 (L-CDR3); and a heavy chain variable region comprising the amino acid sequence of SEQ ID NO: 55 (H-CDR1); the amino acid sequence of SEQ ID NO: 65 (H-CDR2); the amino acid sequence of SEQ ID NO: 74 (H-CDR3); or a light chain variable region comprising the amino acid sequence of SEQ ID NO: 29 (L-CDR1); the amino acid sequence of SEQ ID NO: 38 (L-CDR2); the amino acid sequence of SEQ ID NO: 47 (L-CDR3); and a heavy chain variable region comprising the amino acid sequence of SEQ ID NO: 56 (H-CDR1); the amino acid sequence of SEQ ID NO: 66 (H-CDR2); the amino acid sequence of SEQ ID NO: 75 (H-CDR3).

In embodiment thirty six, the present invention provides an anti-IL-36R antibody or antigen-binding fragment thereof, wherein the antibody or antigen-binding fragment thereof comprises a light chain variable region comprising the amino acid sequence of SEQ ID NO: 1; and a heavy chain variable region comprising the amino acid sequence of SEQ ID NO: 11; or a light chain variable region comprising the amino acid sequence of SEQ ID NO: 2; and a heavy chain variable region comprising the amino acid sequence of SEQ ID NO: 12; or a light chain variable region comprising the amino acid sequence of SEQ ID NO: 3; and a heavy chain variable region comprising the amino acid sequence of SEQ ID NO: 13; or a light chain variable region comprising the amino acid sequence of SEQ ID NO: 4; and a heavy chain variable region comprising the amino acid sequence of SEQ ID NO: 14; or a light chain variable region comprising the amino acid sequence of SEQ ID NO: 5; and a heavy chain variable region comprising the amino acid sequence of SEQ ID NO: 15; or a light chain variable region comprising the amino acid sequence of SEQ ID NO: 6; and a heavy chain variable region comprising the amino acid sequence of SEQ ID NO: 16; or a light chain variable region comprising the amino acid sequence of SEQ ID NO: 7; and a heavy chain variable region comprising the amino acid sequence of SEQ ID NO: 17; or a light chain variable region comprising the amino acid sequence of SEQ ID NO: 8; and a heavy chain variable region comprising the amino acid sequence of SEQ ID NO: 18; or a light chain variable region comprising the amino acid sequence of SEQ ID NO: 9; and a heavy chain variable region comprising the amino acid sequence of SEQ ID NO: 19; or a light chain variable region comprising the amino acid sequence of SEQ ID NO: 10; and a heavy chain variable region comprising the amino acid sequence of SEQ ID NO: 20.

In a further embodiment thirty seven, the present invention provides a pharmaceutical composition comprising an antibody or antigen-binding fragment according to any one of the previous embodiments and a pharmaceutically acceptable carrier.

In a further embodiment thirty eight the present invention provides an antibody or antigen-binding fragment or pharmaceutical composition according to any one of the previous embodiments, for use in medicine.

In a further embodiment thirty nine the present invention provides an antibody or antigen-binding fragment or pharmaceutical composition according to any one of the embodiments 1-37, wherein the use is the treatment of an inflammatory disease, of an autoimmune disease, of a respiratory disease, of a metabolic disorder, of an epithelial mediated inflammatory disorder, fibrosis or of cancer.

In a further embodiment forty the present invention provides an antibody or antigen-binding fragment or pharmaceutical composition according to any one of the embodiments 1-37, wherein the use is for the treatment of psoriasis, inflammatory bowel disease, psoriatic arthritis, multiple sclerosis, rheumatoid arthritis, COPD, chronic asthma or ankylosing spondylitis.

In a further embodiment forty one, the present invention provides an antibody or antigen-binding fragment or pharmaceutical composition according to any one of the embodiments 1-37, wherein the use is for the treatment of inflammatory bowel disease.

In a still further embodiment forty two, the present invention provides an antibody or antigen-binding fragment or pharmaceutical composition according to embodiment 41, wherein the disease is Crohns disease.

In another embodiment forty three, the present invention provides a method of treating a disease comprising administering the antibody or antigen-binding fragment or pharmaceutical composition according to any one of the embodiments 1-37, to a patient in need thereof, wherein the disease is selected from an inflammatory disease, an autoimmune disease, a respiratory disease, a metabolic disorder, an epithelial mediated inflammatory disorder, fibrosis and cancer.

In another embodiment forty four, the present invention provides a method according to embodiment 43 wherein the disease is selected from psoriasis, inflammatory bowel disease, psoriatic arthritis, multiple sclerosis, rheumatoid arthritis, COPD, chronic asthma and ankylosing spondylitis.

In a still further embodiment forty five, the present invention provides a method for treating Crohns disease.

Further embodiments of the invention encompass:
An isolated polynucleotide comprising a sequence encoding an anti-IL-36R antibody or antigen-binding fragment according to the invention, preferably a DNA or RNA sequence;
an isolated polynucleotide according to the invention, encoding a sequence as defined by one or more of SEQ ID NOs. 1 to 140;
a vector comprising a polynucleotide according to the invention, preferably an expression vector, more preferred a vector comprising the polynucleotide according to the invention in functional association with an expression control sequence;
a host cell comprising a polynucleotide according to the invention and/or a vector according to the invention;
a method for the production of an anti-IL-36R antibody or antigen-binding fragment according to the invention, preferably a recombinant production method comprising the use of a polynucleotide according to the invention, and/or of a vector according to the invention and/or of a host cell according to the invention;
such a method preferably comprises the steps (a) cultivating the host cell under conditions allowing the expression of the anti-IL-36R antibody or antigen-binding fragment and (b) recovering the anti-IL-36R antibody or antigen-binding fragment;

a diagnostic kit or diagnostic method comprising an anti-IL-36R antibody or antigen-binding fragment according to the invention, or the use thereof;

a Diagnostic kit or diagnostic method according the invention, for the diagnosis of an inflammatory disease, an autoimmune disease, a respiratory disease, a metabolic disorder, an epithelial mediated inflammatory disorder, fibrosis, cancer, psoriasis, inflammatory bowel disease, psoriatic arthritis, multiple sclerosis, rheumatoid arthritis, COPD, chronic asthma, ankylosing spondylitis, or Crohns disease.

DESCRIPTION OF THE INVENTION

This invention relates to anti-IL-36R antibodies. In one aspect, the antibodies of the present invention are for diagnostic and therapeutic use, for example in humans.

The present invention provides antibodies that bind to IL-36R, in particular human IL-36R. The present invention also relates to humanized antibodies that bind IL-36R. In specific embodiments, the sequence of these humanized antibodies has been identified based on the sequences of certain lead mouse antibodies.

Figure 1:
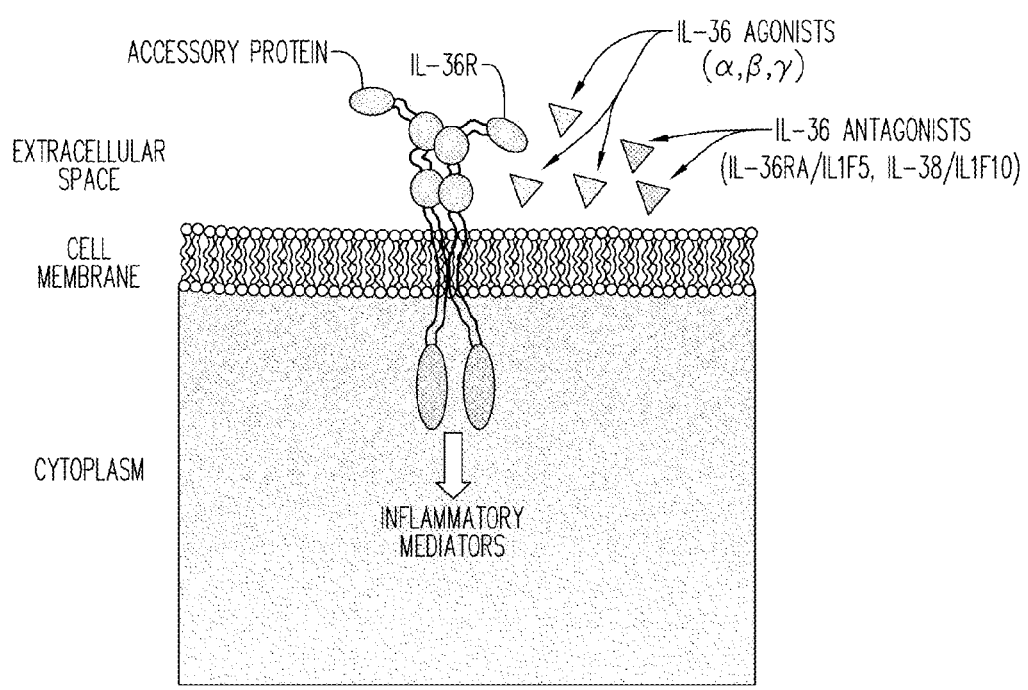
FIG. 1: IL-36 antagonist ligands (IL-36RA/IL1F5, IL-38/ILF10) inhibit the signaling cascade.
Figure 2:
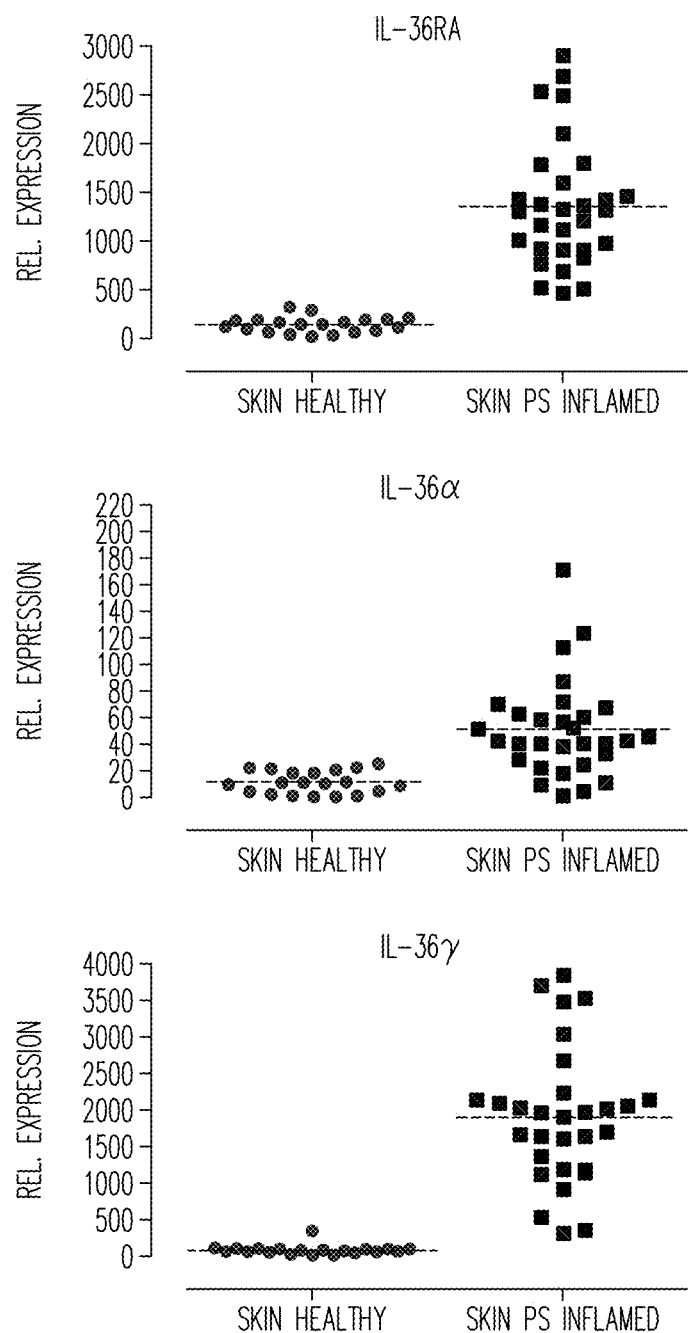
FIG. 2: Gene chip analyses demonstrate IL-36R ligands are upregulated in psoriatic skin (IL-36 RA, IL-36 α and IL-36 γ).
Figure 3:
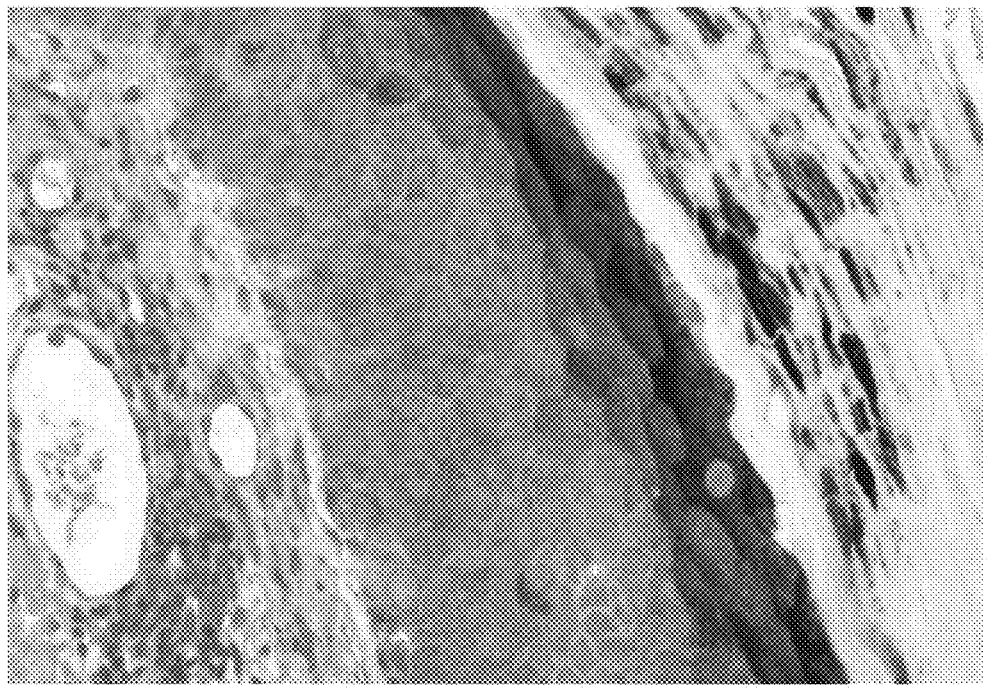
FIG. 3: Expression profile using human skin sections. Formalin-fixed paraffin embedded with antibody titrations using antibody 33D10
Figure 3:
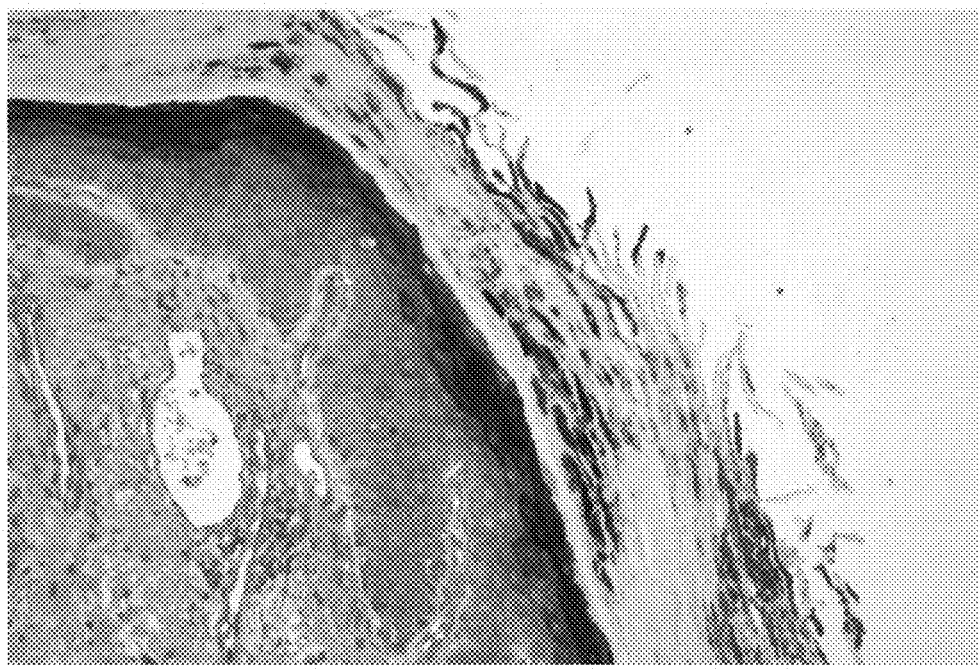

Without wishing to be bound by this theory it is believed that anti-IL-36R antibodies or antigen-binding fragments thereof bind to human IL-36R and thus interfere with the binding of IL-36 agonists, and in doing so block at least partially the signaling cascade from the IL-36R to inflammatory mediators. This is illustrated by FIG. 1.

In one aspect, the antibodies of the present invention are for use in models of human disease. IL-36R is also known as IL-1RL2 and IL-1Rrp2. It has been reported that agonistic IL-36 ligands (α, β, or γ) initiate the signaling cascade by engaging the IL-36 receptor which then forms a heterodimer with the IL-1 receptor accessory protein (IL-1RAcP). IL-36 antagonist ligands (IL-36RA/IL1F5, IL-38/ILF10) inhibit the signaling cascade (see FIG. 1).

In one aspect, the present invention provides an anti-IL-36R antibody having one or more of the properties below.

In one aspect, an anti-IL-36R antibody of the present invention has high molecular/cellular binding potency. In one aspect, an anti-IL-36R antibody of the present invention binds to human IL-36R at a $K_D<0.1$ nM. In a further aspect, an anti-IL-36R antibody of the present invention, in particular a humanized anti-IL-36R antibody, binds to human IL-36R at a $K_D<50$ pM. In one aspect, an anti-IL-36R antibody of the present invention binds to IL-36R expressing cells at an $EC_{90}<5$ nM.

In another aspect, an anti-IL-36R antibody of the present invention has high cell-based functional blocking potency. In one aspect, an anti-IL-36R antibody of the present invention blocks all three IL-36R agonistic ligands (α, β, γ) at an $IC_{90}<5$ nM, in disease-relevant cell lines and primary cells.

In one aspect, an anti-IL-36R antibody of the present invention has the molecular/cellular binding potency and the cell-based functional blocking potency set forth above.

In one aspect, an anti-IL-36R antibody of the present invention is a humanized antibody. In one aspect, an anti-IL-36R antibody of the present invention is a monoclonal antibody. In one aspect, an anti-IL-36R antibody of the present invention is a full length antibody. In one aspect, an anti-IL-36R antibody of the present invention is a humanized monoclonal antibody, for example a full length humanized monoclonal antibody.

An antibody or antigen-binding fragment thereof of the present invention recognizes specific "IL-36R antigen epitope" or "IL-36R epitope". As used herein these terms refer to a molecule (e.g., a peptide) or a fragment of a molecule capable of immunoreactivity with an anti-IL-36R antibody.

The epitopes are most commonly proteins, short oligopeptides, oligopeptide mimics (i.e., organic compounds that mimic antibody binding properties of the IL-36R antigen), or combinations thereof. The minimum size of a peptide or polypeptide epitope for an antibody is thought to be about four to five amino acids. Peptide or polypeptide epitopes contain for example at least seven amino acids or for example at least nine amino acids or for example between about 15 to about 20 amino acids. Since an antibody can recognize an antigenic peptide or polypeptide in its tertiary form, the amino acids comprising an epitope need not be contiguous, and in some cases, may not even be on the same peptide chain. Epitopes may be determined by various techniques known in the art, such as X-ray crystallography, Hydrogen/Deuterium Exchange Mass Spectrometry (HXMS), site-directed mutagenesis, alanine scanning mutagenesis, and peptide screening methods.

The generalized structure of antibodies or immunoglobulin is well known to those of skill in the art. These molecules are heterotetrameric glycoproteins, typically of about 150,000 daltons, composed of two identical light (L) chains and two identical heavy (H) chains and are typically referred to as full length antibodies. Each light chain is covalently linked to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663). Variable domains are also referred herein as variable regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5$^{th}$ Ed. Public Health Service, National Institutes of Health, Bethesda, Md., whereas HVLs (also referred herein as CDRs) are structurally defined according to the three-dimensional structure of the variable domain, as described by Chothia and Lesk, 1987, J. Mol. Biol. 196: 901-917. These two methods result in slightly different identifications of a CDR. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The exact residue numbers that encompass a particular CDR will vary depending on the sequence and size of the CDR. Those skilled in the art can routinely determine which residues comprise a particular CDR given the variable region amino acid sequence of the antibody. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody dependent cellular cytotoxicity (ADCC), complement dependent cytotoxicity (CDC) and antibody dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-IL-36R antibody", "humanized anti-IL-36R antibody", "humanized anti-IL-36R epitope antibody", and "variant humanized anti-IL-36R epitope antibody" specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., IL-36R binding. The term "monoclonal antibody" (mAb) refers to an antibody that is highly specific, being directed against a single antigenic determinant, an "epitope". Therefore, the modifier "monoclonal" is indicative of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256: 495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

The term "monomer" refers to a homogenous form of an antibody. For example, for a full-length antibody, monomer means a monomeric antibody having two identical heavy chains and two identical light chains.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "anti-IL-36R antibody fragment", "anti-IL-36R epitope antibody fragment", "humanized anti-IL-36R antibody fragment", "humanized anti-IL-36R epitope antibody fragment", "variant humanized anti-IL-36R epitope antibody fragment" refer to a portion of a full length anti-IL-36R antibody, in which a variable region or a functional capability is retained, for example, specific IL-36R epitope binding. Examples of antibody fragments include, but are not limited to, a Fab, Fab', F(ab')$_2$, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the C$_{H1}$ domain of the heavy chain. Pepsin treatment yields a F(ab')$_2$ fragment that has two antigen-binding sites and is still capable of crosslinking antigen.

Fab' fragments differ from Fab fragments by the presence of additional residues including one or more cysteines from the antibody hinge region at the C-terminus of the $C_{H1}$ domain. F(ab')$_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

A "diabody" refers to small antibody fragments with two antigen-binding sites, which fragments comprise a heavy chain variable domain (V.sub.H) connected to a light chain variable domain (V.sub.L) in the same polypeptide chain (V.sub.H-V.sub.L or V.sub.L-V.sub.H). Diabodies are described more fully in, e.g., Holliger et al. (1993) Proc. Natl. Acad. Sci. USA 90: 6444-6448.

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A "humanized antibody" or a "humanized antibody fragment" is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. The present invention describes specific humanized anti-IL-36R antibodies which contain CDRs derived from the mouse monoclonal antibodies or humanized CDRs inserted between the FRs of human germline sequence heavy and light chain variable domains. It will be understood that certain mouse FR residues may be important to the function of the humanized antibodies and therefore certain of the human germline sequence heavy and light chain variable domains residues are modified to be the same as those of the corresponding mouse sequence.

In another aspect, a humanized anti-IL-36R antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, all of the CDRs are mouse or humanized sequences as detailed herein below and all, or substantially all, of the FRs are those of a human immunoglobulin consensus or germline sequence. In another aspect, a humanized anti-IL-36R antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-IL-36r antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibit cytotoxic activity, and the isotype is typically $IgG_1$. Where such cytotoxic activity is not desirable, the constant domain may be of another isotype, e.g., $IgG_2$. An alternative humanized anti-IL-36R antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly, are IgG1 antibodies in which there is a knock-out of effector functions.

The FRs and CDRs, or HVLs, of a humanized anti-IL-36R antibody need not correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to IL-36R. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof.

Human germline sequences are found naturally in the human population. A combination of those germline genes generates antibody diversity. Germline antibody sequences for the light chain of the antibody come from conserved human germline kappa or lambda v-genes and j-genes. Similarly the heavy chain sequences come from germline v-, d- and j-genes (LeFranc, M-P, and LeFranc, G, "The Immunoglobulin Facts Book" Academic Press, 2001).

As used herein, "variant", "anti-IL-36R variant", "humanized anti-IL-36R variant", or "variant humanized anti-IL-36R" each refers to a humanized anti-IL-36R antibody having at least a light chain variable murine CDR. Variants include those having one or more amino acid changes in one or both light chain or heavy chain variable domains, provided that the amino acid change does not substantially impair binding of the antibody to IL-36R.

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

The term "antibody performance" refers to factors that contribute to antibody recognition of antigen or the effectiveness of an antibody in vivo. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half life of the antibody.

The term "epitope tagged" when used herein, refers to an anti-IL-36R antibody fused to an "epitope tag". An "epitope tag" is a polypeptide having a sufficient number of amino acids to provide an epitope for antibody production, yet is designed such that it does not interfere with the desired activity of the humanized anti-IL-36R antibody. The epitope tag is usually sufficiently unique such that an antibody raised against the epitope tag does not substantially cross-react with other epitopes. Suitable tag polypeptides generally contain at least 6 amino acid residues and usually contain about 8 to 50 amino acid residues, or about 9 to 30 residues. Examples of epitope tags and the antibody that binds the epitope include the flu HA tag polypeptide and its antibody 12CA5 (Field et al., 1988 Mol. Cell. Biol. 8: 2159-2165; c-myc tag and 8F9, 3C7, 6E10, G4, B7 and 9E10 antibodies thereto (Evan et al., 1985, Mol. Cell. Biol. 5(12):3610-3616; and Herpes simplex virus glycoprotein D (gD) tag and its antibody (Paborsky et al. 1990, Protein Engineering 3(6): 547-553). In certain embodiments, the epitope tag is a "salvage receptor binding epitope". As used herein, the term "salvage receptor binding epitope" refers to an epitope of the Fc region of an IgG molecule (such as $IgG_1$, $IgG_2$, $IgG_3$, or $IgG_4$) that is responsible for increasing the in vivo serum half-life of the IgG molecule.

In some embodiments, the antibodies of the present invention may be conjugated to a cytotoxic agent. This is any substance that inhibits or prevents the function of cells and/or causes destruction of cells. The term is intended to include radioactive isotopes (such as $I^{131}$, $I^{125}$, $Y^{90}$, and $Re^{186}$), chemotherapeutic agents, and toxins such as enzymatically active toxins of bacterial, fungal, plant, or animal origin, and fragments thereof. Such cytotoxic agents can be coupled to the humanized antibodies of the present invention using standard procedures, and used, for example, to treat a patient indicated for therapy with the antibody.

A "chemotherapeutic agent" is a chemical compound useful in the treatment of cancer. There are numerous examples of chemotherapeutic agents that could be conjugated with the therapeutic antibodies of the present invention. Examples of such chemotherapeutic agents include alkylating agents such a thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatin, auristatins, (including analogues monomethyl-auristatin E and monomethyl-auristatin F); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phi1I, see for example, Agnew, Chem. Intl. Ed. Engl., 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™) raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above. Any one or more of these agents may be conjugated to the humanized antibodies of the present invention to provide a useful therapeutic agent for the treatment of various disorders.

The antibodies also may be conjugated to prodrugs. A "prodrug" is a precursor or derivative form of a pharmaceutically active substance that is less cytotoxic to tumor cells compared to the parent drug and is capable of being enzymatically activated or converted into the more active form. See, for example, Wilman, 1986, "Prodrugs in Cancer Chemotherapy", In Biochemical Society Transactions, 14, pp. 375-382, 615th Meeting Belfast and Stella et al., 1985, "Prodrugs: A Chemical Approach to Targeted Drug Delivery, In: "Directed Drug Delivery, Borchardt et al., (ed.), pp. 247-267, Humana Press. Useful prodrugs include, but are not limited to, phosphate-containing prodrugs, thiophosphate-containing prodrugs, sulfate-containing prodrugs peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

For diagnostic as well as therapeutic monitoring purposes, the antibodies of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to a humanized antibody of the present invention. The label may itself be detectable (e.g., radioisotope labels or fluorescent labels) or, in the case of an enzymatic label, may catalyze chemical alteration of a substrate compound or composition that is detectable. Labeled humanized anti-IL-36R antibody can be prepared and used in various applications including in vitro and in vivo diagnostics.

The antibodies of the present invention may be formulated as part of a liposomal preparation in order to affect delivery thereof in vivo. A "liposome" is a small vesicle composed of various types of lipids, phospholipids, and/or surfactant. Liposomes are useful for delivery to a mammal of a compound or formulation, such as a humanized anti-IL-36R antibody disclosed herein, optionally, coupled to or in combination with one or more pharmaceutically active agents and/or labels. The components of the liposome are commonly arranged in a bilayer formation, similar to the lipid arrangement of biological membranes.

Certain aspects of the present invention related to isolated nucleic acids that encode one or more domains of the humanized antibodies of the present invention. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is distinguished from the nucleic acid molecule as it exists in natural cells.

In various aspects of the present invention one or more domains of the humanized antibodies will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of humanized anti-IL-36R antibody in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-IL-36R antibody described herein. This includes chronic and acute disorders or diseases including those pathological conditions that predispose the mammal to the disorder in question. Non-limiting examples or disorders to be treated herein include inflammatory, angiogenic, autoimmune and immunologic disorders, respiratory disorders, cancer, hematological malignancies, benign and malignant tumors, leukemias and lymphoid malignancies.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia.

An IL-36R-associated disorder includes diseases and disorders of the immune system, such as autoimmune disorders and inflammatory disorders. Such conditions include, but are not limited to, rheumatoid arthritis (RA), systemic lupus erythematosus (SLE), scleroderma, Sjogren's syndrome, multiple sclerosis, psoriasis, psoriatic arthritis, inflammatory bowel disease (e.g., ulcerative colitis and Crohn's disease), pulmonary inflammation, asthma, idiopathic thrombocytopenic purara (ITP) epithelial inflammatory disorders, fibrosis and ankylosing spondylitis.

The term "intravenous infusion" refers to introduction of an agent into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an active agent that relieves or ameliorates one or more of the symptoms of the disorder being treated. In another aspect, the therapeutically effective amount refers to a target serum concentration that has been shown to be effective in, for example, slowing disease progression. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the humanized anti-IL-36R antibody composition, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

In one aspect, described and disclosed herein are anti-IL-36R antibodies, in particular humanized anti-IL-36R antibodies, and compositions and articles of manufacture comprising one or more anti-IL-36R antibody, in particular one or more humanized anti-IL-36R antibody of the present invention. Also described are binding agents that include an antigen-binding fragment of an anti-IL-36 antibody, in particular a humanized anti-IL-36R antibody.

Variable regions and CDRs of representative antibodies of the present invention are disclosed below:

Anti-IL-36R Mouse Antibody Sequences

Variable regions and CDRs of representative mouse lead antibodies of the present invention (mouse leads) are shown below:

Light Chain Variable Region (VK) Amino Acid Sequences
>33D10B12vK Protein (antibody 33D10)
(SEQ ID NO: 1)
QIVLTQSPAIMSASLGERVTMTCTASSSVSSSYLHWYQKKPGSSPKLWVYSTSNLASGV

PVRFSGSGSGTSYSLTISSMEAEDAATYYCHQHHRSPVTFGSGTKLEMK

>172C8B12 vK protein (antibody 172C8)
(SEQ ID NO: 2)
DIQMTQSPASQSASLGESVTFTCLASQTIGTWLAWYQQRPGKSPQLLIYAATSLADGVPS

RFSGSGSGTQFSFNIRSLQAEDFASYYCQQVYTTPLTFGGGTKLEIK

>67E7E8 vK protein (antibody 67E7)
(SEQ ID NO: 3)
DIQMTQSPASQSASLGESVTFTCLASQTIGTWLGWYQQKPGKSPQLLIYRSTTLADGVPS

RFSGSGSGTKFSFKISSLQAADFASYYCQQLYSAPYTFGGGTKLEIR

>78C8D1 vK Protein (antibody 78C8)
(SEQ ID NO: 4)
DVLLTQTPLSLPVSLGDQASISCRSSQNIVHSNGNTYLQWYLQKPGQSPKLLIYKVSNRF

SGVPDRFSGSGSGTDFTLKISRVEAEDLGVYYCFQGSHVPFTFGAGTKLELK

>81A1D1 vK Protein (antibody 81A1)
(SEQ ID NO: 5)
DIQMTQTTSSLSASLGDRVTISCRASQDIYKYLNWYQQKPDGTLKLLIYYTSGLHSGVPS

RFSGSGSGTDFSLTISNLEPEDIATYFCQQDSKFPWTFGGDTKLEIK

>81B4E11 vK Protein (antibody 81B4)
(SEQ ID NO: 6)
QIVLTQSPAIMSASLGERVTMTCTASSSVSSSYFHWYQQKPGSSPKLWIYRTSNLASGVP

GRFSGSGSGTSYSLTISSMEAEDAATYYCHQFHRSPLTFGAGTKLELK

>73C5C10 vK protein (antibody 73C5)
(SEQ ID NO: 7)
DIVMTQSQKFLSTSVGVRVSVTCKASQDVGTNVLWYQQKIGQSPKPLIYSASYRHSGVP

DRFTGSGSGTDFTLIISNVQSEDLAEYFCQQYSRYPLTFGPGTKLELK

>73F6F8 vK protein (antibody 73F6)
(SEQ ID NO: 8)
DIVMTQSQKFLSTSVGVRVSVTCKASQDVGTNVLWYQQKIGQSPKALIYSASYRHSGVP

DRFTGSGSGTDFTLIITNVQSEDLAEYFCQQYSRYPLTFGPGTKLELK

>76E10E8 vK protein (antibody 76E10)
(SEQ ID NO: 9)
DIVMTQSQKFMSATVGGRVNITCKASQNVGRAVAWYQQKPGQSPKLLTHSASNRYTG

VPDRFTGSGSGTDFTLTITNMQSEDLADYFCQQYSSYPLTFGAGTKLDLK

>89A12B8 vK protein (antibody 89A12)
(SEQ ID NO: 10)
DIQMTQSPASQSASLGESVTFSCLASQTIGTWLGWYQQKPGKSPQLLIYRATSLADGVPS

RFSGSGSGTNFSFKISSLQAEDLASYYCQQLYSGPYTFGGGTKLEIR

Heavy Chain Variable Region (VH) Amino Acid Sequences
>33D10B12vH Protein (antibody 33D10)
(SEQ ID NO: 11)
QVQLQQSGTELLKPGASVKLSCKASGNTVTSYWMHWVKQRPGQGLEWIGEILPSTGRT

NYNENFKGKAMLTVDKSSSTAYMQLSSLASEDSAVYYCTIVYFGNPWHAYWGQGTLV

TVSA

>172C8B12 vH prolan (antibody 172C8)
(SEQ ID NO: 12)
EVQLQQSGPELVKPGASVKLSCKASGYTFTDNYMNWVRQSHGKSLEWIGRVNPSNGD

TKYNQNFKGKATLTVDKSLSTAYMQLNGLTSEDSAVYYCGRTKNFYSSYSYDDAMDY

WGQGTSVTVSS

>67E7E8 vH protein (antibody 67E7)
(SEQ ID NO: 13)
EVQLQQSGAEFVRPGASVKFSCTASGFNIKDDYIHWVRQRPEQGLEWVGRIDPANGNT -continued

KYAPKFQDKATITADTSSNTAYLQLSSLTSEDTAVYYCAKSFPNNYYSYDDAFAYWGQ

GTLVTVSA

>78C8D1 vH Protein (antibody 78C8)
(SEQ ID NO: 14)
QVQLKESGPVLVAPSQSLSITCTVSGFSLTKFGVHWIRQTPGKGLEWLGVIWAGGPTNY

NSALMSRLTISKDISQSQVFLRIDSLQTDDTAMYYCAKQIYYSTLVDYWGQGTSVTVSS

>81A1D1 vH Protein (antibody 81A1)
(SEQ ID NO: 15)
QVQLKESGPGLVAPSQSLFITCTVSGFSLSSYEINWVRQVPGKGLEWLGVIWTGITTNYN

SALISRLSISKDNSKSLVFLKMNSLQTDDTAIYYCARGTGTGFYYAMDYWGQGTSVTVS

S

>81B4E11 vH Protein (antibody 81B4)
(SEQ ID NO: 16)
QVQLQQPGADFVRPGASMRLSCKASGYSFTSSWIHWVKQRPGQGLEWIGEINPGNVRT

NYNENFRNKATLTVDKSSTTAYMQLRSLTSADSAVYYCTVVFYGEPYFPYWGQGTLVT

VSA

>73C5C10 vH Protein (antibody 73C5)
(SEQ ID NO: 17)
QVQLKESGPGLVAPSQSLSITCTVSGFSLTNYAVHWVRQFPGKGLEWLGVIWSDGSTDF

NAPFKSRLSINKDNSKSQVFFKMNSLQIDDTAIYYCARKGGYSGSWFAYWGQGTLVTV

SA

>73F6F8 vH protein (antibody 73F6)
(SEQ ID NO: 18)
QVQLKESGPGLVAPSQSLSITCTVSGFSLTNYAVHWVRQFPGKGLEWLGVIWSDGSTDY

NAPFKSRLSINKDNSKSQVFFKMNSLQTDDTAIYYCARKGGYSGSWFAYWGQGTLVTV

SA

>76E10E8 vH protein (antibody 76E10)
(SEQ ID NO: 19)
VQLKESGPVLVAPSQSLSITCTVSGFSLTNYGVHWVRQPPGKGLEWLGVIWPVGSTNY

NSALMSRLSIHKDNSKSQVFLRMNSLQTDDTAIYYCAKMDWDDFFDYWGQGTTLTVSS

>89A12B8 vH Protein (antibody 89A12)
(SEQ ID NO: 20)
EVQLQQSGAELVRPGASVRLSCTASGFNIKDDYIHWVRQRPKQGLEWLGRIDPANGNT

KYDPRFQDKATITADTSSNTAYLHLSSLTSEDTAVYYCAKSFPDNYYSYDDAFAYWGQ

GTLVTVSA

Light chain CDR-1 (L-CDR1) Amino Acid Sequences
>33D10G1 L-CDR1
(SEQ ID NO: 21)
TASSSVSSSYLH

>172C8B12 L-CDR1
(SEQ ID NO: 22)
LASQTIGTWLA

>67E7E8 L-CDR1
(SEQ ID NO: 23)
LASQTIGTWLG

>78C8D1 L-CDR1
(SEQ ID NO: 24)
RSSQNIVHSNGNTYLQ

>81A1D1 L-CDR1
(SEQ ID NO: 25)
RASQDIYKYLN

>81B4E11 L-CDR1
(SEQ ID NO: 26)
TASSSVSSSYFH

-continued

```
>73C5C10 L-CDR1
                                                  (SEQ ID NO: 27)
KASQDVGTNVL

>73F6F8 L-CDR1
                                                  (SEQ ID NO: 27)
KASQDVGTNVL

>76E10E8 L-CDR1
                                                  (SEQ ID NO: 28)
KASQNVGRAVA

>89A12B8 L-CDR1
                                                  (SEQ ID NO: 29)
LASQTIGTWLG

Light chain CDR-2 (L-CDR2) Amino Acid Sequences
>33D10B12 L-CDR2
                                                  (SEQ ID NO: 30)
STSNLAS >172C8B12 L-CDR2
                                                  (SEQ ID NO: 31)
AATSLAD >67E7E8 L-CDR2
                                                  (SEQ ID NO: 32)
RSTTLAD >78C8D1 L-CDR2
                                                  (SEQ ID NO: 33)
KVSNRFS >81A1D1 L-CDR2
                                                  (SEQ ID NO: 34)
YTSGLHS >81B4E11 L-CDR2
                                                  (SEQ ID NO: 35)
RTSNLAS >73C5C10 L-CDR2
                                                  (SEQ ID NO: 36)
SASYRHS >73F6F8 L-CDR2
                                                  (SEQ ID NO: 36)
SASYRHS >76E10E8 L-CDR2
                                                  (SEQ ID NO: 37)
SASNRYT >89A12B8 L-CDR2
                                                  (SEQ ID NO: 38)
RATSLAD Light chain CDR-3 (L-CDR3) Amino Acid Sequences
>33D10B12 L-CDR3
                                                  (SEQ ID NO: 39)
HQHHRSPVT >172C8B12 L-CDR3
                                                  (SEQ ID NO: 40)
QQVYTTPLT >67E7E8 L-CDR3
                                                  (SEQ ID NO: 41)
QQLYSAPYT >78C8D1 L-CDR3
                                                  (SEQ ID NO: 42)
FQGSHVPFT >81A1D1 L-CDR3
                                                  (SEQ ID NO: 43)
QQDSKFPWT

>81B4E11 L-CDR3
```

```
                                                    (SEQ ID NO: 44)
HQFHRSPLT

>73C5C10 L-CDR3
                                                    (SEQ ID NO: 45)
QQYSRYPLT

>73F6F8 L-CDR3
                                                    (SEQ ID NO: 45)
QQYSRYPLT

>76E10E8 L-CDR3
                                                    (SEQ ID NO: 46)
QQYSSYPLT

>89A12B8 L-CDR3
                                                    (SEQ ID NO: 47)
QQLYSGPYT

Heavy chain CDR-1 (H-CDR1) Amino Acid Sequences
>33D10B12 H-CDR1
                                                    (SEQ ID NO: 48)
GNTVTSYWMH >172C8B12 H-CDR1
                                                    (SEQ ID NO: 49)
GYTFTDNYMN >67E7E8 H-CDR1
                                                    (SEQ ID NO: 50)
GFNIKDDYIH >78C8D1 H-CDR1
                                                    (SEQ ID NO: 51)
GFSLTKFGVH >81A1D1 H-CDR1
                                                    (SEQ ID NO: 52)
GFSLSSYEIN >81B4E11 H-CDR1
                                                    (SEQ ID NO: 53)
GYSFTSSWIH >73C5C10 H-CDR1
                                                    (SEQ ID NO: 54)
GFSLTNYAVH >73F6F8 H-CDR1
                                                    (SEQ ID NO: 54)
GFSLTNYAVH >76E10E8 H-CDR1
                                                    (SEQ ID NO: 55)
GFSLTNYGVH >89A12B8 H-CDR1
                                                    (SEQ ID NO: 56)
GFNIKDDYIH Heavy chain CDR-2 (H-CDR2) Amino Acid Sequences
>33D10B12 H-CDR2
                                                    (SEQ ID NO: 57)
EILPSTGRTNYNENFKG >172C8B12 H-CDR2
                                                    (SEQ ID NO: 58)
RVNPSNGDTKYNQNFKG >67E7E8 H-CDR2
                                                    (SEQ ID NO: 59)
RIDPANGNTKYAPKFQD >78C8D1 H-CDR2
                                                    (SEQ ID NO: 60)
VIWAGGPTNYNSALMS >81A1D1 H-CDR2
                                                    (SEQ ID NO: 61)
VIWTGITTNYNSALIS
```

-continued

```
>81B4E11 H-CDR2
                                            (SEQ ID NO: 62)
EINPGNVRTNYNENF

>73C5C10 H-CDR2
                                            (SEQ ID NO: 63)
VIWSDGSTDFNAPFKS

>73F6F8 H-CDR2
                                            (SEQ ID NO: 64)
VIWSDGSTDYNAPFKS

>76E10E8 H-CDR2
                                            (SEQ ID NO: 65)
VIWPVGSTNYNSALMS

>89A12B8 H-CDR2
                                            (SEQ ID NO: 66)
RIDPANGNTKYDPRFQD

Heavy chain CDR-3 (H-CDR3) Amino Acid Sequences
>33D10B12 H-CDR3
                                            (SEQ ID NO: 67)
VYFGNPWFAY >172C8B12 H-CDR3
                                            (SEQ ID NO: 68)
TKNFYSSYSYDDAMDY >67E7E8 H-CDR3
                                            (SEQ ID NO: 69)
SFPNNYYSYDDAFAY >78C8D1 H-CDR3
                                            (SEQ ID NO: 70)
QIYYSTLVDY >81A1D1 H-CDR3
                                            (SEQ ID NO: 71)
GTGTGFYYAMDY >81B4E11 H-CDR3
                                            (SEQ ID NO: 72)
VFYGEPYFPY >73C5C10 H-CDR3
                                            (SEQ ID NO: 73)
KGGYSGSWFAY >73F6F8 H-CDR3
                                            (SEQ ID NO: 73)
KGGYSGSWFAY >76E10E8 H-CDR3
                                            (SEQ ID NO: 74)
MDWDDFFDY >89A12B8 H-CDR3
                                            (SEQ ID NO: 75)
SFPDNYYSYDDAFAY
```

Anti-IL-36R Mouse CDR Sequences
A summary of the CDR sequences of the lead mouse antibodies is shown below:

| Antibody | H-CDR Sequences | L-CDR Sequences |
|---|---|---|
| 33D10 | GNTVTSYWMH (H-CDR1) SEQ ID No: 48<br>EILPSTGRTNYNENFKG (H-CDR2) SEQ ID No: 57<br>VYFGNPWFAY (H-CDR3) SEQ ID No: 67 | TASSSVSSSYLH (L-CDR1) SEQ ID No: 21<br>STSNLAS (L-CDR2) SEQ ID No: 30<br>HQHHRSPVT (L-CDR3) SEQ ID No: 39 |
| 172C8 | GYTFTDNYMN (H-CDR1) SEQ ID No: 49<br>RVNPSNGDTKYNQNFKG (H-CDR2) SEQ ID No: 58 | LASQTIGTWLA (L-CDR1) SEQ ID No: 22<br>AATSLAD (L-CDR2) SEQ ID No: 31 |

| Antibody | H-CDR Sequences | L-CDR Sequences |
|---|---|---|
| | TKNFYSSYSYDDAMDY (H-CDR3) SEQ ID No: 68 | QQVYTTPLT (L-CDR3) SEQ ID No: 40 |
| 67E7 | GFNIKDDYIH (H-CDR1) SEQ ID No: 50 RIDPANGNTKYAPKFQD (H-CDR2) SEQ ID No: 59 SFPNNYYSYDDAFAY (H-CDR3) SEQ ID No: 69 | LASQTIGTWLG (L-CDR1) SEQ ID No: 23 RSTTLAD (L-CDR2) SEQ ID No: 32 QQLYSAPYT (L-CDR3) SEQ ID No: 41 |
| 78C8 | GFSLTKFGVH (H-CDR1) SEQ ID No: 51 VIWAGGPTNYNSALMS (H-CDR2) SEQ ID No: 60 QIYYSTLVDY (H-CDR3) SEQ ID No: 70 | RSSQNIVHSNGNTYLQ (L-CDR1) SEQ ID No: 24 KVSNRFS (L-CDR2) SEQ ID No: 33 FQGSHVPFT (L-CDR3) SEQ ID No: 42 |
| 81A1 | GFSLSSYEIN (H-CDR1) SEQ ID No: 52 VIWTGITTNYNSALIS (H-CDR2) SEQ ID No: 61 GTGTGFYYAMDY (H-CDR3) SEQ ID No: 71 | RASQDIYKYLN (L-CDR1) SEQ ID No: 25 YTSGLHS (L-CDR2) SEQ ID No: 34 QQDSKFPWT (L-CDR3) SEQ ID No: 43 |
| 81B4 | GYSFTSSWIH (H-CDR1) SEQ ID No: 53 EINPGNVRTNYNENF (H-CDR2) SEQ ID No: 62 VFYGEPYFPY (H-CDR3) SEQ ID No: 72 | TASSSVSSSYFH (L-CDR1) SEQ ID No: 26 RTSNLAS (L-CDR2) SEQ ID No: 35 HQFHRSPLT (L-CDR3) SEQ ID No: 44 |
| 73C5 | GFSLTNYAVH (H-CDR1) SEQ ID No: 54 VIWSDGSTDFNAPFKS (H-CDR2) SEQ ID No: 63 KGGYSGSWFAY (H-CDR3) SEQ ID No: 73 | KASQDVGTNVL (L-CDR1) SEQ ID No: 27 SASYRHS (L-CDR2) SEQ ID No: 36 QQYSRYPLT (L-CDR3) SEQ ID No: 45 |
| 73F6 | GFSLTNYAVH (H-CDR1) SEQ ID No: 54 VIWSDGSTDYNAPFKS (H-CDR2) SEQ ID No: 64 KGGYSGSWFAY (H-CDR3) SEQ ID No: 73 | KASQDVGTNVL (L-CDR1) SEQ ID No: 27 SASYRHS (L-CDR2) SEQ ID No: 36 QQYSRYPLT (L-CDR3) SEQ ID No: 45 |
| 76E10 | GFSLTNYGVH (H-CDR1) SEQ ID No: 55 VIWPVGSTNYNSALMS (H-CDR2) SEQ ID No: 65 MDWDDFFDY (H-CDR3) SEQ ID No: 74 | KASQNVGRAVA (L-CDR1) SEQ ID No: 28 SASNRYT (L-CDR2) SEQ ID No: 37 QQYSSYPLT (L-CDR3) SEQ ID No: 46 |
| 89A12 | GFNIKDDYIH (H-CDR1) SEQ ID No: 56 RIDPANGNTKYDPRFQD (H-CDR2) SEQ ID No: 66 SFPDNYYSYDDAFAY (H-CDR3) SEQ ID No: 75 | LASQTIGTWLG (L-CDR1) SEQ ID No: 29 RATSLAD (L-CDR2) SEQ ID No: 38 QQLYSGPYT (L-CDR3) SEQ ID No: 47 |

Anti-IL-36R Humanized Antibody Sequences

Human framework sequences were selected for the mouse leads based on the framework homology, CDR structure, conserved canonical residues, conserved interface packing residues and other parameters to produce humanized variable regions (see Example 5).

Representative humanized variable regions derived from antibodies 81B4 and 73C5 are shown below.

```
Light Chain Variable Region (VK) Amino Acid Sequences
>81B4vK32_3 vK protein
                                                       (SEQ ID NO: 76)
EIVLTQSPGTLSLSPGERATMSCTASSSVSSSYFHWYQQKPGQAPRLLIYRTSTLASGIPD

RFSGSGSGTDFTLTISRLEPEDAATYYCHQFHRSPLTFGQGTKLEIK

>81B4vK32_105 vK protein
                                                       (SEQ ID NO: 77)
EIVLTQSPGTLSLSPGERATMSCTASSSVSSSYFHWYQQKPGQAPRLLIYRTSILASGVPD
```

RFSGSGSGTDFTLTISRLEPEDFATYYCHQFHRSPLTFGQGTKLEIK

>81B4vK32_116 vK protein (SEQ ID NO: 78)
EIVLTQSPGTLSLSPGERATMSCTASSSVSSSYFHWYQQKPGQAPRLWIYRTSRLASGVP

DRFSGSGSGTDFTLTISRLEPEDAATYYCHQFHRSPLTFGQGTKLEIK

>81B4vK32_127 vK protein (SEQ ID NO: 79)
EIVLTQSPGTLSLSPGERATMTCTASSSVSSSYFHWYQQKPGQAPRLLIYRTSRLASGVP

DRFSGSGSGTDFTLTISRLEPEDFAVYYCHQFHRSPLTFGQGTKLEIK

>81B4vK32_138 vK protein (SEQ ID NO: 80)
QIVLTQSPGTLSLSPGERATMTCTASSSVSSSYFHWYQQKPGQAPRLWIYRTSRLASGVP

DRFSGSGSGTDFTLTISRLEPEDAATYYCHQFHRSPLTFGAGTKLEIK

>81B4vK32_140 vK protein (SEQ ID NO: 81)
QIVLTQSPGTLSLSPGERVTMSCTASSSVSSSYFHWYQQKPGQAPRLLIYRTSQLASGIPD

RFSGSGSGTDFTLTISRLEPEDAATYYCHQFHRSPLTFGQGTKLEIK

>81B4vK32_141 vK protein (SEQ ID NO: 82)
QIVLTQSPGTLSLSPGERATMTCTASSSVSSSYFHWYQQKPGQAPRLLIYRTSKLASGVP

DRFSGSGSGTDFTLTISRLEPEDFATYYCHQFHRSPLTFGQGTKLEIK

>81B4vK32_147 vK protein (SEQ ID NO: 83)
EIVLTQSPGTLSLSPGERATMSCTASSSVSSSYFHWYQQKPGQAPRLLIYRTSHLASGIPG

RFSGSGSGTDFTLTISRLEPEDAAVYYCHQFHRSPLTFGQGTKLEIK

>73C5vK39_2 vK protein (SEQ ID NO: 84)
EIVMTQSPATLSVSPGVRATLSCKASQDVGTNVLWYQQKPGQAPRPLIYSASYRHSGIP

DRFSGSGSGTEFTLTISSLQSEDFAEYFCQQYSRYPLTFGQGTKLEIK

>73C5vK39_7 vK protein (SEQ ID NO: 85)
EIVMTQSPATLSVSPGVRATLSCKASQDVGTNVLWYQQKPGQAPRPLIYSASYRHSGIP

DRFSGSGSGTEFTLTISSLQSEDFAVYYCQQYSRYPLTFGQGTKLEIK

>73C5vK39_15 vK protein (SEQ ID NO: 86)
EIVMTQSPATLSVSPGVRATLSCKASQDVGTNVLWYQQKPGQAPRPLIYSASYRHSGIP

ARFSGSGSGTEFTLTISSLQSEDFAEYYCQQYSRYPLTFGQGTKLEIK

Heavy Chain Variable Region (VH) Amino Acid Sequences
>81B4vH33_49 vH Protein (SEQ ID NO: 87)
QVQLVQSGAEVKKPGASVKVSCKASGYSFTSSWIHWVRQAPGQGLEWIGEINPGNVRT

NYNENFRNKATMTVDTSISTAYMELSRLRSDDTAVYYCAVVFYGEPYFPYWGQGTLVT

VSS

>81B4vH33_85T vH Protein (SEQ ID NO: 88)
QVQLVQSGAEVKKPGASVKVSCKASGYSFTSSWIHWVRQRPGQGLEWIGEINPGNVRT

NYNENFRNRVTMTVDTSISTAYMELSRLRSDDTAVYYCTVVFYGEPYFPYWGQGTLVT

VSS

>81B4vH33_90 vH Protein (SEQ ID NO: 89)
QVQLVQSGAEVKKPGASVKVSCKASGYSFTSSWIHWVKQAPGQGLEWMGEINPGNVR

TNYNENFRNKVTMTVDTSISTAYMELSRLRSDDTAVYYCTVVFYGEPYFPYWGQGTLV

TVSS

-continued

>81B4vH33_93 vH Protein (SEQ ID NO: 90)

QVQLVQSGAEVKKPGASVKVSCKASGYSFTSSWIHWVRQRPGQGLEWMGEINPGNVR

TNYNENFRNRATLTRDTSISTAYMELSRLRSDDTAVYYCAVVFYGEPYFPYWGQGTLV

TVSS

>81B4vH50_22 vH Protein (SEQ ID NO: 91)

QVQLVQSGAEVKKPGASVKVSCKASGYSFTSSWIHWVRQRPGQGLEWMGEILPGVVR

TNYNENFRNKVTMTVDTSISTAYMELSRLRSDDTAVYYCTVVFYGEPYFPYWGQGTLV

TVSS

>81B4vH50_30 vH Protein (SEQ ID NO: 92)

QVQLVQSGAEVKKPGASVKVSCKASGYSFTSSWIHWVRQRPGQGLEWIGEINPGAVRT

NYNENFRNRVTMTVDTSISTAYMELSRLRSDDTAVYYCTVVFYGEPYFPYWGQGTLVT

VSS

>81B4vH51_13 vH Protein (SEQ ID NO: 93)

QVQLVQSGAEVKKPGASVKVSCKASGYSFTSSWIHWVRQAPGQGLEWIGEINPGLVRT

NYNENFRNKVTMTVDTSISTAYMELSRLRSDDTAVYYCAVVFYGEPYFPYWGQGTLVT

VSS

>81B4vH51_15 vH Protein (SEQ ID NO: 94)

QVQLVQSGAEVKKPGASVKVSCKASGYSFTSSWIHWVRQAPGQGLEWIGEINPGAVRT

NYNENFRNKVTMTVDTSISTAYMELSRLRSDDTAVYYCAVVFYGEPYFPYWGQGTLVT

VSS

>81B4vH52_83 vH Protein (SEQ ID NO: 95)

QVQLVQSGAEVKKPGASVKVSCKASGYSFTSSWIHWVRQAPGQGLEWIGEINPGSVRT

NYNENFRNKATMTVDTSISTAYMELSRLRSDDTAVYYCAVVFYGEPYFPYWGQGTLVT

VSS

>73C5vH46_4 vH Protein (SEQ ID NO: 96)

QVQLQESGPGLVKPSETLSITCTVSGFSLTDYAVHWIRQPPGKGLEWIGVIWSDGSTDYN

APFKSRVTINKDTSKSQVSFKMSSVQAADTAVYYCARKGGYSGSWFAYWGQGTLVTV

SS

>73C5vH46_19 vH Protein (SEQ ID NO: 97)

QVQLQESGPGLVKPSETLSITCTVSGFSLTDYAVHWIRQPPGKGLEWIGVIWSDGSTDYN

APFKSRVTISKDTSKNQVSLKMNSLTTDDTAVYYCARKGGYSGSWFAYWGQGTLVTV

SS

>73C5vH46_40 vH Protein (SEQ ID NO: 98)

QVQLQESGPGLVKPSETLSITCTVSGFSLTDYAVHWIRQPPGKGLEWIGVIWSDGSTDYN

APFKSRVTISKDNSKSQVSLKMNSVTVADTAVYYCARKGGYSGSWFAYWGQGTLVTV

SS

>73C5vH47_65 vH Protein (SEQ ID NO: 99)

QVQLQESGPGLVKPSETLSITCTVSGFSLTDYAVHWVRQPPGKGLEWIGVIWSDGSTDY

NAPFKSRVTISKDTSKNQVSFKLSSVTVDDTAVYYCARKGGYSGSWFAYWGQGTLVTV

SS

```
>73C5vH47_77 vH Protein
                                          (SEQ ID NO: 100)
QVQLQESGPGLVAPSETLSLTCTVSGFSLTDYAVHWIRQFPGKGLEWIGVIWSDGSTDF

NAPFKSRVTISKDTSKNQVSFKLSSVTTDDTAVYYCARKGGYSGSWFAYWGQGTLVTV

SS

>73C5vH58_91 vH Protein
                                          (SEQ ID NO: 101)
QVQLQESGPGLVKPSETLSITCTVSGFSLTDYAVHWIRQPPGKGLEWIGVIWSDGSTDYN

APFKSRVTISKDNSKSQVSFKMSSVTADDTAVYYCARKGGYSGSWFAYWGQGTLVTVS

S
```

The CDR sequences from the humanized variable regions derived from antibodies 81B4 and 73C5 shown above are depicted below.

L-CDR1 Amino Acid Sequences

```
>81B4vK32_3 L-CDR1
TASSSVSSSYFH              (SEQ ID NO: 26)

>81B4vK32_105 L-CDR1
TASSSVSSSYFH              (SEQ ID NO: 26)

>81B4vK32_116 L-CDR1
TASSSVSSSYFH              (SEQ ID NO: 26)

>81B4vK32_127 L-CDR1
TASSSVSSSYFH              (SEQ ID NO: 26)

>81B4vK32_138 L-CDR1
TASSSVSSSYFH              (SEQ ID NO: 26)

>81B4vK32_140 L-CDR1
TASSSVSSSYFH              (SEQ ID NO: 26)

>81B4vK32_141 L-CDR1
TASSSVSSSYFH              (SEQ ID NO: 26)

>81B4vK32_147 L-CDR1
TASSSVSSSYFH              (SEQ ID NO: 26)

>73C5vK39_2 L-CDR1
KASQDVGTNVL               (SEQ ID NO: 27)

>73C5vK39_7 L-CDR1
KASQDVGTNVL               (SEQ ID NO: 27)

>73C5vK39_15 L-CDR1
KASQDVGTNVL               (SEQ ID NO: 27)
```

L-CDR2 Amino Acid Sequences

```
>81B4vK32_3 L-CDR2         (SEQ ID 102)
RTSTLAS

>81B4vK32_105 L-CDR2       (SEQ ID 103)
RTSILAS

>81B4vK32_116 L-CDR2       (SEQ ID 104)
RTSRLAS

>81B4vK32_127 L-CDR2       (SEQ ID 104)
RTSRLAS

>81B4vK32_138 L-CDR2       (SEQ ID 104)
RTSRLAS

>81B4vK32_140 L-CDR2       (SEQ ID 105)
RTSQLAS

>81B4vK32_141 L-CDR2       (SEQ ID 106)
RTSKLAS

>81B4vK32_147 L-CDR2       (SEQ ID 140)
RTSHLAS

>73C5vK39_2 L-CDR2
SASYRHS                   (SEQ ID NO: 36)

>73C5vK39_7 L-CDR2
SASYRHS                   (SEQ ID NO: 36)

>73C5vK39_15 L-CDR2
SASYRHS                   (SEQ ID NO: 36)
```

L-CDR3 Amino Acid Sequences

```
>81B4vK32_3 L-CDR3
HQFHRSPLT                 (SEQ ID NO: 44)

>81B4vK32_105 L-CDR3
HQFHRSPLT                 (SEQ ID NO: 44)

>81B4vK32_116 L-CDR3
HQFHRSPLT                 (SEQ ID NO: 44)

>81B4vK32_127 L-CDR3
HQFHRSPLT                 (SEQ ID NO: 44)

>81B4vK32_138 L-CDR3
HQFHRSPLT                 (SEQ ID NO: 44)

>81B4vK32_140 L-CDR3
HQFHRSPLT                 (SEQ ID NO: 44)

>81B4vK32_141 L-CDR3
HQFHRSPLT                 (SEQ ID NO: 44)

>81B4vK32_147 L-CDR3
HQFHRSPLT                 (SEQ ID NO: 44)

>73C5vK39_2 L-CDR3
QQYSRYPLT                 (SEQ ID NO: 45)

>73C5vK39_7 L-CDR3
QQYSRYPLT                 (SEQ ID NO: 45)

>73C5vK39_15 L-CDR3
QQYSRYPLT                 (SEQ ID NO: 45)
```

H-CDR1 Amino Acid Sequences

```
>81B4vH33_49 H-CDR1
GYSFTSSWIH                (SEQ ID NO: 53)

>81B4vH33_85T H-CDR1
GYSFTSSWIH                (SEQ ID NO: 53)

>81B4vH33_90 H-CDR1
GYSFTSSWIH                (SEQ ID NO: 53)
```

-continued

```
>81B4vH33_93 H-CDR1
GYSFTSSWIH              (SEQ ID NO: 53)

>81B4vH50_22 H-CDR1
GYSFTSSWIH              (SEQ ID NO: 53)

>81B4vH50_30 H-CDR1
GYSFTSSWIH              (SEQ ID NO: 53)

>81B4vH51_13 H-CDR1
GYSFTSSWIH              (SEQ ID NO: 53)

>81B4vH51_15 H-CDR1
GYSFTSSWIH              (SEQ ID NO: 53)

>81B4vH52_83 H-CDR1
GYSFTSSWIH              (SEQ ID NO: 53)

>73C5vH46_4 H-CDR1
GFSLTDYAVH              (SEQ ID NO: 107)

>73C5vH46_19 H-CDR1
GFSLTDYAVH              (SEQ ID NO: 107)

>73C5vH46_40 H-CDR1
GFSLTDYAVH              (SEQ ID NO: 107)

>73C5vH47_65 H-CDR1
GFSLTDYAVH              (SEQ ID NO: 107)

>73C5vH47_77 H-CDR1
GFSLTDYAVH              (SEQ ID NO: 107)

>73C5vH58_91 H-CDR1
GFSLTDYAVH              (SEQ ID NO: 107)
```

H-CDR2 Amino Acid Sequences

```
>81B4vH33_49 H-CDR2
EINPGNVRTNYNENF         (SEQ ID NO: 62)

>81B4vH33_85T H-CDR2
EINPGNVRTNYNENF         (SEQ ID NO: 62)

>81B4vH33_90 H-CDR2
EINPGNVRTNYNENF         (SEQ ID NO: 62)

>81B4vH33_93 H-CDR2
EINPGNVRTNYNENF         (SEQ ID NO: 62)

>81B4vH50_22 H-CDR2
EILPGVVRTNYNENF         (SEQ ID NO: 108)

>81B4vH50_30 H-CDR2
EINPGAVRTNYNENF         (SEQ ID NO: 109)

>81B4vH51_13 H-CDR2
EINPGLVRTNYNENF         (SEQ ID NO: 110)

>81B4vH51_15 H-CDR2
EINPGAVRTNYNENF         (SEQ ID NO: 109)

>81B4vH52_83 H-CDR2
EINPGSVRTNYNENF         (SEQ ID NO: 111)

>73C5vH46_4 H-CDR2
VIWSDGSTDYNAPFKS        (SEQ ID NO: 64)

>73C5vH46_19 H-CDR2
VIWSDGSTDYNAPFKS        (SEQ ID NO: 64)

>73C5vH46_40 H-CDR2
VIWSDGSTDYNAPFKS        (SEQ ID NO: 64)

>73C5vH47_65 H-CDR2
VIWSDGSTDYNAPFKS        (SEQ ID NO: 64)

>73C5vH47_77 H-CDR2
VIWSDGSTDFNAPFKS        (SEQ ID NO: 63)

>73C5vH58_91 H-CDR2
VIWSDGSTDYNAPFKS        (SEQ ID NO: 64)
```

H-CDR3 Amino Acid Sequences

```
>81B4vH33_49 H-CDR3
VFYGEPYFPY              (SEQ ID NO: 72)

>81B4vH33_85T H-CDR3
VFYGEPYFPY              (SEQ ID NO: 72)

>81B4vH33_90 H-CDR3
VFYGEPYFPY              (SEQ ID NO: 72)

>81B4vH33_93 H-CDR3
VFYGEPYFPY              (SEQ ID NO: 72)

>81B4vH50_22 H-CDR3
VFYGEPYFPY              (SEQ ID NO: 72)

>81B4vH50_30 H-CDR3
VFYGEPYFPY              (SEQ ID NO: 72)

>81B4vH51_13 H-CDR3
VFYGEPYFPY              (SEQ ID NO: 72)

>81B4vH51_15 H-CDR3
VFYGEPYFPY              (SEQ ID NO: 72)

>81B4vH52_83 H-CDR3
VFYGEPYFPY              (SEQ ID NO: 72)

>73C5vH46_4 H-CDR3
KGGYSGSWFAY             (SEQ ID NO: 73)

>73C5vH46_19 H-CDR3
KGGYSGSWFAY             (SEQ ID NO: 73)

>73C5vH46_40 H-CDR3
KGGYSGSWFAY             (SEQ ID NO: 73)

>73C5vH47_65 H-CDR3
KGGYSGSWFAY             (SEQ ID NO: 73)

>73C5vH47_77 H-CDR3
KGGYSGSWFAY             (SEQ ID NO: 73)

>73C5vH58_91 H-CDR3
KGGYSGSWFAY             (SEQ ID NO: 73)
```

In one aspect, a variable region of the present invention is linked to a constant region. For example, a variable region of the present invention is linked to a constant region shown below to form a heavy chain or a light chain of an antibody.

```
Heavy Chain Constant region linked
downstream of a humanized variable
heavy region:
                              (SEQ ID NO: 112)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Light Chain Constant region linked
downstream of a humanized variable
light region:
(SEQ ID NO: 113)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Representative light chain and heavy chain sequences of the present invention are shown below (humanized variable regions derived from antibodies 81B4 and 73C5 linked to constant regions).

```
Light Chain Amino Acid Sequences
>81B4vK32_3 Light Chain
                                        (SEQ ID NO: 114)
EIVLTQSPGTLSLSPGERATMSCTASSSVSSSYFHWYQQKPGQAPRLLIYRTSTLASGIPD

RFSGSGSGTDFTLTISRLEPEDAATYYCHQFHRSPLTFGQGTKLEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

>81B4vK32_105 Light Chain
                                        (SEQ ID NO: 115)
EIVLTQSPGTLSLSPGERATMSCTASSSVSSSYFHWYQQKPGQAPRLLIYRTSILASGVPD

RFSGSGSGTDFTLTISRLEPEDFATYYCHQFHRSPLTFGQGTKLEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

>81B4vK32_116 Light Chain
                                        (SEQ ID NO: 116)
EIVLTQSPGTLSLSPGERATMSCTASSSVSSSYFHWYQQKPGQAPRLWIYRTSRLASGVP

DRFSGSGSGTDFTLTISRLEPEDAATYYCHQFHRSPLTFGQGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

>81B4vK32_127 Light Chain
                                        (SEQ ID NO: 117)
EIVLTQSPGTLSLSPGERATMTCTASSSVSSSYFHWYQQKPGQAPRLLIYRTSRLASGVP

DRFSGSGSGTDFTLTISRLEPEDFAVYYCHQFHRSPLTFGQGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

>81B4vK32_138 Light Chain
                                        (SEQ ID NO: 118)
QIVLTQSPGTLSLSPGERATMTCTASSSVSSSYFHWYQQKPGQAPRLWIYRTSRLASGVP

DRFSGSGSGTDFTLTISRLEPEDAATYYCHQFHRSPLTFGAGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

>81B4vK32_140 Light Chain
                                        (SEQ ID NO: 119)
QIVLTQSPGTLSLSPGERVTMSCTASSSVSSSYFHWYQQKPGQAPRLLIYRTSQLASGIPD

RFSGSGSGTDFTLTISRLEPEDAATYYCHQFHRSPLTFGQGTKLEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC
```

>81B4vK32_141 Light Chain
(SEQ ID NO: 120)
QIVLTQSPGTLSLSPGERATMTCTASSSVSSSYFHWYQQKPGQAPRLLIYRTSKLASGVP

DRFSGSGSGTDFTLTISRLEPEDFATYYCHQFHRSPLTFGQGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

>81B4vK32_147 Light Chain
(SEQ ID NO: 121)
EIVLTQSPGTLSLSPGERATMSCTASSSVSSSYFHWYQQKPGQAPRLLIYRTSHLASGIPG

RFSGSGSGTDFTLTISRLEPEDAAVYYCHQFHRSPLTFGQGTKLEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

>73C5vK39_2 Light Chain
(SEQ ID NO: 122)
EIVMTQSPATLSVSPGVRATLSCKASQDVGTNVLWYQQKPGQAPRPLIYSASYRHSGIP

DRFSGSGSGTEFTLTISSLQSEDFAEYFCQQYSRYPLTFGQGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

>73C5vK39_7 Light Chain
(SEQ ID NO: 123)
EIVMTQSPATLSVSPGVRATLSCKASQDVGTNVLWYQQKPGQAPRPLIYSASYRHSGIP

DRFSGSGSGTEFTLTISSLQSEDFAVYYCQQYSRYPLTFGQGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

>73C5vK39_15 Light Chain
(SEQ ID NO: 124)
EIVMTQSPATLSVSPGVRATLSCKASQDVGTNVLWYQQKPGQAPRPLIYSASYRHSGIP

ARFSGSGSGTEFTLTISSLQSEDFAEYYCQQYSRYPLTFGQGTKLEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

Heavy Chain Amino Acid Sequences
>81B4vH33_49 Heavy Chain
(SEQ ID NO: 125)
QVQLVQSGAEVKKPGASVKVSCKASGYSFTSSWIHWVRQAPGQGLEWIGEINPGNVRT

NYNENFRNKATMTVDTSISTAYMELSRLRSDDTAVYYCAVVFYGEPYFPYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCPPCPAPEA

AGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

>81B4vH33_85T Heavy Chain
(SEQ ID NO: 126)
QVQLVQSGAEVKKPGASVKVSCKASGYSFTSSWIHWVRQRPGQGLEWIGEINPGNVRT

NYNENFRNRVTMTVDTSISTAYMELSRLRSDDTAVYYCTVVFYGEPYFPYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCPPCPAPEA

AGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

>81B4vH33_90 Heavy Chain
(SEQ ID NO: 127)
QVQLVQSGAEVKKPGASVKVSCKASGYSFTSSWIHWVKQAPGQGLEWMGEINPGNVR

TNYNENFRNKVTMTVDTSISTAYMELSRLRSDDTAVYYCTVVFYGEPYFPYWGQGTLV

TVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCDKTHTCPPCPAPE

AAGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSK

LTVDKSRWQQGNVFSCSVMHEALHNHYTQKSLSLSPGK

>81B4vH33_93 Heavy Chain
(SEQ ID NO: 128)
QVQLVQSGAEVKKPGASVKVSCKASGYSFTSSWIHWVRQRPGQGLEWMGEINPGNVR

TNYNENFRNRATLTRDTSISTAYMELSRLRSDDTAVYYCAVVFYGEPYFPYWGQGTLV

TVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCDKTHTCPPCPAPE

AAGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSK

LTVDKSRWQQGNVFSCSVMHEALHNHYTQKSLSLSPGK

>81B4vH50_22 Heavy Chain
(SEQ ID NO: 129)
QVQLVQSGAEVKKPGASVKVSCKASGYSFTSSWIHWVRQRPGQGLEWMGEILPGVVR

TNYNENFRNKVTMTVDTSISTAYMELSRLRSDDTAVYYCTVVFYGEPYFPYWGQGTLV

TVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCDKTHTCPPCPAPE

AAGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSK

LTVDKSRWQQGNVFSCSVMHEALHNHYTQKSLSLSPGK

>81B4vH50_30 Heavy Chain
(SEQ ID NO: 130)
QVQLVQSGAEVKKPGASVKVSCKASGYSFTSSWIHWVRQRPGQGLEWIGEINPGAVRT

NYNENFRNRVTMTVDTSISTAYMELSRLRSDDTAVYYCTVVFYGEPYFPYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCPPCPAPEA

AGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

-continued

>81B4vH51_13 Heavy Chain
(SEQ ID NO: 131)
QVQLVQSGAEVKKPGASVKVSCKASGYSFTSSWIHWVRQAPGQGLEWIGEINPGLVRT

NYNENFRNKVTMTVDTSISTAYMELSRLRSDDTAVYYCAVVFYGEPYFPYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCPPCPAPEA

AGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

>81B4vH51_15 Heavy Chain
(SEQ ID NO: 132)
QVQLVQSGAEVKKPGASVKVSCKASGYSFTSSWIHWVRQAPGQGLEWIGEINPGAVRT

NYNENFRNKVTMTVDTSISTAYMELSRLRSDDTAVYYCAVVFYGEPYFPYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCPPCPAPEA

AGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

>81B4vH52_83 Heavy Chain
(SEQ ID NO: 133)
QVQLVQSGAEVKKPGASVKVSCKASGYSFTSSWIHWVRQAPGQGLEWIGEINPGSVRT

NYNENFRNKATMTVDTSISTAYMELSRLRSDDTAVYYCAVVFYGEPYFPYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCPPCPAPEA

AGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

>73C5vH46_4 Heavy Chain
(SEQ ID NO: 134)
QVQLQESGPGLVKPSETLSITCTVSGFSLTDYAVHWIRQPPGKGLEWIGVIWSDGSTDYN

APFKSRVTINKDTSKSQVSFKMSSVQAADTAVYYCARKGGYSGSWFAYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKRVEPKSCDKTHTCPPCPAPEAA

GGPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTV

DKSRWQQGNVFSCSVMHEALHNHYTQKSLSLSPGK

>73C5vH46_19 Heavy Chain
(SEQ ID NO: 135)
QVQLQESGPGLVKPSETLSITCTVSGFSLTDYAVHWIRQPPGKGLEWIGVIWSDGSTDYN

APFKSRVTISKDTSKNQVSLKMNSLTTDDTAVYYCARKGGYSGSWFAYWGQGTLVTV

SSASTKGPSVFPLAPSSKSTSGGTAALGCLVKDYFPEPVTVSWNSGALTSGVHTFPAVLQ

```
SSGLYSLSSVVTVPSSSLGTQTYICNVNHKPSNTKVDKRVEPKSCDKTHTCPPCPAPEAA
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK

>73C5vH46_40 Heavy Chain
                                                   (SEQ ID NO: 136)
QVQLQESGPGLVKPSETLSITCTVSGFSLTDYAVHWIRQPPGKGLEWIGVIWSDGSTDYN
APFKSRVTISKDNSKSQVSLKMNSVTVADTAVYYCARKGGYSGSWFAYWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAA
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK >73C5vH47_65 Heavy Chain
                                                   (SEQ ID NO: 137)
QVQLQESGPGLVKPSETLSITCTVSGFSLTDYAVHWVRQPPGKGLEWIGVIWSDGSTDY
NAPFKSRVTISKDTSKNQVSFKLSSVTVDDTAVYYCARKGGYSGSWFAYWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAA
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK >73C5vH47_77 Heavy Chain
                                                   (SEQ ID NO: 138)
QVQLQESGPGLVAPSETLSLTCTVSGFSLTDYAVHWIRQFPGKGLEWIGVIWSDGSTDF
NAPFKSRVTISKDTSKNQVSFKLSSVTTDDTAVYYCARKGGYSGSWFAYWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAA
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK >73C5vH58_91 Heavy Chain
                                                   (SEQ ID NO: 139)
QVQLQESGPGLVKPSETLSITCTVSGFSLTDYAVHWIRQPPGKGLEWIGVIWSDGSTDYN
APFKSRVTISKDNSKSQVSFKMSSVTADDTAVYYCARKGGYSGSWFAYWGQGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAPEAAG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPS
```

```
REEMTKNQVSLTCLVKGFYPSDIAVEWESNGQPENNYKTTPPVLDSDGSFFLYSKLTVD

KSRWQQGNVFSCSVMHEALHNHYTQKSLSLSPGK
The CDRs listed above are defined using the Chothia
numbering system (Al-Lazikani et al., (1997)
JMB 273, 927-948).
```

In one aspect, an antibody of the present invention comprises 3 light chain CDRs and 3 heavy chain CDRs, for example as set forth above.

In one aspect, an antibody of the present invention comprises a light chain and a heavy chain variable region as set forth above. In one aspect, a light chain variable region of the invention is fused to a light chain constant region, for example a kappa or lambda constant region. In one aspect, a heavy chain variable region of the invention is fused to a heavy chain constant region, for example IgA, IgD, IgE, IgG or IgM, in particular, $IgG_1$, $IgG_2$, $IgG_3$ or $IgG_4$.

The present invention provides an anti-IL-36R antibody comprising a light chain comprising the amino acid sequence of SEQ ID NO: 115; and a heavy chain comprising the amino acid sequence of SEQ ID NO: 125 (Antibody B1).

The present invention provides an anti-IL-36R antibody comprising a light chain comprising the amino acid sequence of SEQ ID NO: 115; and a heavy chain comprising the amino acid sequence of SEQ ID NO: 126 (Antibody B2).

The present invention provides an anti-IL-36R antibody comprising a light chain comprising the amino acid sequence of SEQ ID NO: 115; and a heavy chain comprising the amino acid sequence of SEQ ID NO: 127 (Antibody B3).

The present invention provides an anti-IL-36R antibody comprising a light chain comprising the amino acid sequence of SEQ ID NO: 118; and a heavy chain comprising the amino acid sequence of SEQ ID NO: 125 (Antibody B4).

The present invention provides an anti-IL-36R antibody comprising a light chain comprising the amino acid sequence of SEQ ID NO: 118; and a heavy chain comprising the amino acid sequence of SEQ ID NO: 126 (Antibody B5).

The present invention provides an anti-IL-36R antibody comprising a light chain comprising the amino acid sequence of SEQ ID NO: 118; and a heavy chain comprising the amino acid sequence of SEQ ID NO: 127 Antibody B6).

The present invention provides an anti-IL-36R antibody comprising a light chain comprising the amino acid sequence of SEQ ID NO: 123; and a heavy chain comprising the amino acid sequence of SEQ ID NO: 138 (Antibody C3).

The present invention provides an anti-IL-36R antibody comprising a light chain comprising the amino acid sequence of SEQ ID NO: 123; and a heavy chain comprising the amino acid sequence of SEQ ID NO: 139 (Antibody C2).

The present invention provides an anti-IL-36R antibody comprising a light chain comprising the amino acid sequence of SEQ ID NO: 124; and a heavy chain comprising the amino acid sequence of SEQ ID NO: 138 (Antibody C1)

Representative antibodies of the present invention are shown below.

TABLE A

| Antibody | Light Chain Sequences | Heavy Chain Sequences |
|---|---|---|
| B1 | EIVLTQSPGTLSLSPGERATMSCTA SSSVSSSYFHWYQQKPGQAPRLLI YRTSILASGVPDRFSGSGSGTDFTL TISRLEPEDFATYYCHQFHRSPLTF GQGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 115) | QVQLVQSGAEVKKPGASVKVSCKASGYS FTSSWIHWVRQAPGQGLEWIGEINPGNV RTNYNENFRNKATMTVDTSISTAYMELS RLRSDDTAVYYCAVVFYGEPYFPYWGQ GTLVTVSSASTKGPSVFPLAPSSKSTSGGT AALGCLVKDYFPEPVTVSWNSGALTSGV HTFPAVLQSSGLYSLSSVVTVPSSSLGTQT YICNVNHKPSNTKVDKRVEPKSCDKTHT CPPCPAPEAAGGPSVFLFPPKPKDTLMISR TPEVTCVVVDVSHEDPEVKFNWYVDGV EVHNAKTKPREEQYNSTYRVVSVLTVLH QDWLNGKEYKCKVSNKALPAPIEKTISK AKGQPREPQVYTLPPSREEMTKNQVSLT CLVKGFYPSDIAVEWESNGQPENNYKTT PPVLDSDGSFFLYSKLTVDKSRWQQGNV FSCSVMHEALHNHYTQKSLSLSPGK (SEQ ID NO: 125) |
| B2 | EIVLTQSPGTLSLSPGERATMSCTA SSSVSSSYFHWYQQKPGQAPRLLI YRTSILASGVPDRFSGSGSGTDFTL TISRLEPEDFATYYCHQFHRSPLTF GQGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 115) | QVQLVQSGAEVKKPGASVKVSCKASGYS FTSSWIHWVRQRPGQGLEWIGEINPGNVR TNYNENFRNRVTMTVDTSISTAYMELSR LRSDDTAVYYCTVVFYGEPYFPYWGQGT LVTVSSASTKGPSVFPLAPSSKSTSGGTAA LGCLVKDYFPEPVTVSWNSGALTSGVHT FPAVLQSSGLYSLSSVVTVPSSSLGTQTYI CNVNHKPSNTKVDKRVEPKSCDKTHTCP PCPAPEAAGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK (SEQ ID NO: 126) |

TABLE A-continued

| Antibody | Light Chain Sequences | Heavy Chain Sequences |
|---|---|---|
| B3 | EIVLTQSPGTLSLSPGERATMSCTA SSSVSSSYFHWYQQKPGQAPRLLI YRTSILASGVPDRFSGSGSGTDFTL TISRLEPEDFATYYCHQFHRSPLTF GQGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 115) | QVQLVQSGAEVKKPGASVKVSCKASGYS FTSSWIHWVKQAPGQGLEWMGEINPGNV RTNYNENFRNKVTMTVDTSISTAYMELS RLRSDDTAVYYCTVVFYGEPYFPYWGQG TLVTVSSASTKGPSVFPLAPSSKSTSGGTA ALGCLVKDYFPEPVTVSWNSGALTSGVH TFPAVLQSSGLYSLSSVVTVPSSSLGTQTY ICNVNHKPSNTKVDKRVEPKSCDKTHTC PPCPAPEAAGGPSVFLFPPKPKDTLMISRT PEVTCVVVDVSHEDPEVKFNWYVDGVE VHNAKTKPREEQYNSTYRVVSVLTVLHQ DWLNGKEYKCKVSNKALPAPIEKTISKA KGQPREPQVYTLPPSREEMTKNQVSLTCL VKGFYPSDIAVEWESNGQPENNYKTTPP VLDSDGSFFLYSKLTVDKSRWQQGNVFS CSVMHEALHNHYTQKSLSLSPGK (SEQ ID NO: 127) |
| B4 | QIVLTQSPGTLSLSPGERATMTCTA SSSVSSSYFHWYQQKPGQAPRLWI YRTSRLASGVPDRFSGSGSGTDFT LTISRLEPEDAATYYCHQFHRSPLT FGAGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 118) | QVQLVQSGAEVKKPGASVKVSCKASGYS FTSSWIHWVRQAPGQGLEWIGEINPGNV RTNYNENFRNKATMTVDTSISTAYMELS RLRSDDTAVYYCAVVFYGEPYFPYWGQ GTLVTVSSASTKGPSVFPLAPSSKSTSGGT AALGCLVKDYFPEPVTVSWNSGALTSGV HTFPAVLQSSGLYSLSSVVTVPSSSLGTQT YICNVNHKPSNTKVDKRVEPKSCDKTHT CPPCPAPEAAGGPSVFLFPPKPKDTLMISR TPEVTCVVVDVSHEDPEVKFNWYVDGV EVHNAKTKPREEQYNSTYRVVSVLTVLH QDWLNGKEYKCKVSNKALPAPIEKTISK AKGQPREPQVYTLPPSREEMTKNQVSLT CLVKGFYPSDIAVEWESNGQPENNYKTT PPVLDSDGSFFLYSKLTVDKSRWQQGNV FSCSVMHEALHNHYTQKSLSLSPGK (SEQ ID NO: 125) |
| B5 | QIVLTQSPGTLSLSPGERATMTCTA SSSVSSSYFHWYQQKPGQAPRLWI YRTSRLASGVPDRFSGSGSGTDFT LTISRLEPEDAATYYCHQFHRSPLT FGAGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 118) | QVQLVQSGAEVKKPGASVKVSCKASGYS FTSSWIHWVRQRPGQGLEWIGEINPGNVR TNYNENFRNRVTMTVDTSISTAYMELSR LRSDDTAVYYCTVVFYGEPYFPYWGQT LVTVSSASTKGPSVFPLAPSSKSTSGGTAA LGCLVKDYFPEPVTVSWNSGALTSGVHT FPAVLQSSGLYSLSSVVTVPSSSLGTQTYI CNVNHKPSNTKVDKRVEPKSCDKTHTCP PCPAPEAAGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK (SEQ ID NO: 126) |
| B6 | QIVLTQSPGTLSLSPGERATMTCTA SSSVSSSYFHWYQQKPGQAPRLWI YRTSRLASGVPDRFSGSGSGTDFT LTISRLEPEDAATYYCHQFHRSPLT FGAGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 118) | QVQLVQSGAEVKKPGASVKVSCKASGYS FTSSWIHWVKQAPGQGLEWMGEINPGNV RTNYNENFRNKVTMTVDTSISTAYMELS RLRSDDTAVYYCTVVFYGEPYFPYWGQG TLVTVSSASTKGPSVFPLAPSSKSTSGGTA ALGCLVKDYFPEPVTVSWNSGALTSGVH TFPAVLQSSGLYSLSSVVTVPSSSLGTQTY ICNVNHKPSNTKVDKRVEPKSCDKTHTC PPCPAPEAAGGPSVFLFPPKPKDTLMISRT PEVTCVVVDVSHEDPEVKFNWYVDGVE VHNAKTKPREEQYNSTYRVVSVLTVLHQ DWLNGKEYKCKVSNKALPAPIEKTISKA KGQPREPQVYTLPPSREEMTKNQVSLTCL VKGFYPSDIAVEWESNGQPENNYKTTPP VLDSDGSFFLYSKLTVDKSRWQQGNVFS CSVMHEALHNHYTQKSLSLSPGK (SEQ ID NO: 127) |

TABLE B

| Antibody | Light Chain Sequences | Heavy Chain Sequences |
|---|---|---|
| C1 | EIVMTQSPATLSVSPGVRATLSCK ASQDVGTNVLWYQQKPGQAPRPL IYSASYRHSGIPARFSGSGSGTEFTL TISSLQSEDFAEYYCQQYSRYPLTF GQGTKLEIKRTVAAPSVFIFPPSDE QLKSGTASVVCLLNNFYPREAKV QWKVDNALQSGNSQESVTEQDSK DSTYSLSSTLTLSKADYEKHKVYA CEVTHQGLSSPVTKSFNRGEC (SEQ ID NO: 124) | QVQLQESGPGLVAPSETLSLTCTVSGFSL TDYAVHWIRQFPGKGLEWIGVIWSDGST DFNAPFKSRVTISKDTSKNQVSFKLSSVTT DDTAVYYCARKGGYSGSWFAYWGQGTL VTVSSASTKGPSVFPLAPSSKSTSGGTAAL GCLVKDYFPEPVTVSWNSGALTSGVHTF PAVLQSSGLYSLSSVVTVPSSSLGTQTYIC NVNHKPSNTKVDKRVEPKSCDKTHTCPP CPAPEAAGGPSVFLFPPKPKDTLMISRTPE VTCVVVDVSHEDPEVKFNWYVDGVEVH NAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK (SEQ ID NO: 138) |
| C2 | EIVMTQSPATLSVSPGVRATLSCK ASQDVGTNVLWYQQKPGQAPRPL IYSASYRHSGIPDRFSGSGSGTEFTL TISSLQSEDFAVYYCQQYSRYPLTF GQGTKLEIKRTVAAPSVFIFPPSDE QLKSGTASVVCLLNNFYPREAKV QWKVDNALQSGNSQESVTEQDSK DSTYSLSSTLTLSKADYEKHKVYA CEVTHQGLSSPVTKSFNRGEC (SEQ ID NO: 123) | QVQLQESGPGLVKPSETLSITCTVSGFSLT DYAVHWIRQPPGKGLEWIGVIWSDGSTD YNAPFKSRVTISKDNSKSQVSFKMSSVTA DDTAVYYCARKGGYSGSWFAYWGQGTL VTVSSASTKGPSVFPLAPSSKSTSGGTAAL GCLVKDYFPEPVTVSWNSGALTSGVHTF PAVLQSSGLYSLSSVVTVPSSSLGTQTYIC NVNHKPSNTKVDKRVEPKSCDKTHTCPP CPAPEAAGGPSVFLFPPKPKDTLMISRTPE VTCVVVDVSHEDPEVKFNWYVDGVEVH NAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK (SEQ ID NO: 139) |
| C3 | EIVMTQSPATLSVSPGVRATLSCK ASQDVGTNVLWYQQKPGQAPRPL IYSASYRHSGIPDRFSGSGSGTEFTL TISSLQSEDFAVYYCQQYSRYPLTF GQGTKLEIKRTVAAPSVFIFPPSDE QLKSGTASVVCLLNNFYPREAKV QWKVDNALQSGNSQESVTEQDSK DSTYSLSSTLTLSKADYEKHKVYA CEVTHQGLSSPVTKSFNRGEC (SEQ ID NO: 123) | QVQLQESGPGLVAPSETLSLTCTVSGFSL TDYAVHWIRQFPGKGLEWIGVIWSDGST DFNAPFKSRVTISKDTSKNQVSFKLSSVTT DDTAVYYCARKGGYSGSWFAYWGQGTL VTVSSASTKGPSVFPLAPSSKSTSGGTAAL GCLVKDYFPEPVTVSWNSGALTSGVHTF PAVLQSSGLYSLSSVVTVPSSSLGTQTYIC NVNHKPSNTKVDKRVEPKSCDKTHTCPP CPAPEAAGGPSVFLFPPKPKDTLMISRTPE VTCVVVDVSHEDPEVKFNWYVDGVEVH NAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK (SEQ ID NO: 138) |

The antibodies of the present invention are useful in methods for the treatment of various diseases or disorders, for example immunological, inflammatory, autoimmune diseases and respiratory diseases in humans. For example, the antibodies of the present invention are useful in methods for the treatment of psoriasis, rheumatoid arthritis, inflammatory bowel disease or psoriatic arthritis. For example, the antibodies of the present invention are useful in methods for the treatment of chronic obstructive pulmonary disorder (COPD) or asthma. For example, the antibodies of the present invention are useful in methods for the treatment of scleroderma, palmoplantar pustulosis, generalized pustular psoriasis, diabetic nephropathy, lupus nephritis, scleroderma, ankylosing spondylitis, deficiency in the IL-36 receptor antagonist autoimmune disease (DITRA), deficiency in the IL-1 receptor antagonist autoimmune disease (DIRA) or cryopyrin associated periodic syndromes (CAPS).

In some aspects, the humanized antibody displays blocking activity, whereby it decreases the binding of IL-36 ligand to IL-36 receptor by at least 45%, by at least 50%, by at least 55%, by at least 60%, by at least 65%, by at least 70%, by at least 75%, by at least 80%, by at least 85%, by at least 90%, or by at least 95%. The ability of an antibody to block binding of IL-36 ligand to the IL-36 receptor can be measured using competitive binding assays known in the art. Alternatively, the blocking activity of an antibody can be measured by assessing the biological effects of IL-36, such as the production of IL-8, IL-6, and GM-CSF to determine if signaling mediated by the IL-36 receptor is inhibited.

In a further aspect, the present invention provides a humanized anti-IL-36R antibody having favorable biophysical properties. In one aspect, a humanized anti-IL-36R antibody of the present invention is present in at least 90% monomer form, or in at least 92% monomer form, or in at least 95% monomer form in a buffer. In a further aspect, a humanized anti-IL-36R antibody of the present invention remains in at least 90% monomer form, or in at least 92% monomer form, or in at least 95% monomer form in a buffer for one month or for four months.

In one aspect, a humanized antibody of the present invention is Antibody B1, Antibody B2, Antibody B3, Antibody B4, Antibody B5, Antibody B6, Antibody C1, Antibody C2, or Antibody C3. Accordingly, in one embodiment, a humanized antibody of the present invention comprises the light chain sequence of SEQ ID NO:115 and the heavy chain sequence of SEQ ID NO:125 (Antibody B1). In another embodiment, a humanized antibody of the present invention comprises the light chain sequence of SEQ ID NO:115 and the heavy chain sequence of SEQ ID NO:126 (Antibody B2). In another embodiment, a humanized antibody of the present invention comprises the light chain sequence of SEQ ID NO:115 and the heavy chain sequence of SEQ ID NO:127 (Antibody B3). In another embodiment, a humanized antibody of the present invention comprises the light chain sequence of SEQ ID NO:118 and the heavy chain sequence of SEQ ID NO:125 (Antibody B4). In another embodiment, a humanized antibody of the present invention comprises the light chain sequence of SEQ ID NO:118 and the heavy chain sequence of SEQ ID NO:126 (Antibody B5). In another embodiment, a humanized antibody of the present invention comprises the light chain sequence of SEQ ID NO:118 and the heavy chain sequence of SEQ ID NO:127 (Antibody B6). In another embodiment, a humanized antibody of the present invention comprises the light chain sequence of SEQ ID NO:124 and the heavy chain sequence of SEQ ID NO:138 (Antibody C1). In another embodiment, a humanized antibody of the present invention comprises the light chain sequence of SEQ ID NO:123 and the heavy chain sequence of SEQ ID NO:139 (Antibody C2). In another embodiment, a humanized antibody of the present invention comprises the light chain sequence of SEQ ID NO:123 and the heavy chain sequence of SEQ ID NO:138 (Antibody C3).

In a further embodiment, a humanized antibody of the present invention consists of the light chain sequence of SEQ ID NO:115 and the heavy chain sequence of SEQ ID NO:125 (Antibody B1). In another embodiment, a humanized antibody of the present invention consists of the light chain sequence of SEQ ID NO:115 and the heavy chain sequence of SEQ ID NO:126 (Antibody B2). In another embodiment, a humanized antibody of the present invention consists of the light chain sequence of SEQ ID NO:115 and the heavy chain sequence of SEQ ID NO:127 (Antibody B3). In another embodiment, a humanized antibody of the present invention consists of the light chain sequence of SEQ ID NO:118 and the heavy chain sequence of SEQ ID NO:125 (Antibody B4). In another embodiment, a humanized antibody of the present invention consists of the light chain sequence of SEQ ID NO:118 and the heavy chain sequence of SEQ ID NO:126 (Antibody B5). In another embodiment, a humanized antibody of the present invention consists of the light chain sequence of SEQ ID NO:118 and the heavy chain sequence of SEQ ID NO:127 (Antibody B6). In another embodiment, a humanized antibody of the present invention consists of the light chain sequence of SEQ ID NO:124 and the heavy chain sequence of SEQ ID NO:138 (Antibody C1). In another embodiment, a humanized antibody of the present invention consists of the light chain sequence of SEQ ID NO:123 and the heavy chain sequence of SEQ ID NO:139 (Antibody C2). In another embodiment, a humanized antibody of the present invention consists of the light chain sequence of SEQ ID NO:123 and the heavy chain sequence of SEQ ID NO:138 (Antibody C3).

In some embodiments, the humanized anti-IL-36R antibodies, including antigen-binding fragments thereof, such as heavy and light chain variable regions, comprise an amino acid sequence of the residues derived from Antibody B1, Antibody B2, Antibody B3, Antibody B4, Antibody B5, Antibody B6, Antibody C1, Antibody C2, or Antibody C3.

In a further embodiment, the present invention provides an anti-IL-36R antibody or antigen-binding fragment thereof that competitively binds to human IL-36R with an antibody of the present invention, for example Antibody B1, Antibody B2, Antibody B3, Antibody B4, Antibody B5, Antibody B6, Antibody C1, Antibody C2 or Antibody C3 described herein. The ability of an antibody or antigen-binding fragment to competitively bind to IL-36R can be measured using competitive binding assays known in the art.

The humanized anti-IL-36R antibodies optionally include specific amino acid substitutions in the consensus or germline framework regions. The specific substitution of amino acid residues in these framework positions can improve various aspects of antibody performance including binding affinity and/or stability, over that demonstrated in humanized antibodies formed by "direct swap" of CDRs or HVLs into the human germline framework regions.

In some embodiments, the present invention describes other monoclonal antibodies with a light chain variable region having the amino acid sequence set forth in any one of SEQ ID NO:1-10. In some embodiments, the present invention describes other monoclonal antibodies with a heavy chain variable region having the amino acid sequence set forth in any one of SEQ ID NO:11-20. Placing such CDRs into FRs of the human consensus heavy and light chain variable domains will yield useful humanized antibodies of the present invention.

In particular, the present invention provides monoclonal antibodies with the combinations of light chain variable and heavy chain variable regions of SEQ ID NO:1/11, 2/12, 3/13, 4/14, 5/15, 6/16, 7/17, 8/18, 9/19, 10/20. Such variable regions can be combined with human constant regions.

In some embodiments, the present invention describes other humanized antibodies with light chain variable region sequences having the amino acid sequence set forth in any one of SEQ ID NO:76-86. In some embodiments, the present invention describes other humanized antibodies with heavy chain variable region sequences having the amino acid sequence set forth in any one of SEQ ID NO:87-101. In particular, the present invention provides monoclonal antibodies with the combinations of light chain variable and heavy chain variable regions of SEQ ID NO: 77/89, 80/88, 80/89, 77/87, 77/88, 80/87, 86/100, 85/101, 85/100. Such variable regions can be combined with human constant regions.

In a further embodiment, the present invention relates to an anti-IL-36R antibody or antigen-binding fragment thereof comprising a humanized light chain variable domain comprising the CDRs of SEQ ID NO:77 and framework regions having an amino acid sequence at least 90% identical, at least 93% identical or at least 95% identical to the amino acid sequence of the framework regions of the variable domain light chain amino acid sequence of SEQ ID NO:77 and a humanized heavy chain variable domain comprising the CDRs of SEQ ID NO:89 and framework regions having an amino acid sequence at least 90% identical, at least 93% identical or at least 95% identical to the amino acid sequence of the framework regions of the variable domain heavy chain amino acid sequence of SEQ ID NO:89. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:80 and framework regions having an amino acid sequence at least 90% identical, at least 93% identical or at least 95% identical to the amino acid sequence of the framework regions of the variable domain light chain amino acid sequence of SEQ ID NO:80 and a humanized heavy chain variable domain comprising the CDRs of SEQ ID NO:88 and framework regions having an amino acid sequence at least 90% identical, at least 93% identical or at least 95% identical to the amino acid sequence of the framework regions of the variable domain heavy chain amino acid sequence of SEQ ID NO:88. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:80 and framework regions having an amino acid sequence at least 90% identical, at least 93% identical or at least 95% identical to the amino acid sequence of the framework regions of the variable domain light chain amino acid sequence of SEQ ID NO:80 and a humanized heavy chain variable domain comprising the CDRs of SEQ ID NO:89 and framework regions having an amino acid sequence at least 90% identical, at least 93% identical or at least 95% identical to the amino acid sequence of the framework regions of the variable domain heavy chain amino acid sequence of SEQ ID NO:89. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:77 and framework regions having an amino acid sequence at least 90% identical, at least 93% identical or at least 95% identical to the amino acid sequence of the framework regions of the variable domain light chain amino acid sequence of SEQ ID NO:77 and a humanized heavy chain variable domain comprising the CDRs of SEQ ID NO:87 and framework regions having an amino acid sequence at least 90% identical, at least 93% identical or at least 95% identical to the amino acid sequence of the framework regions of the variable domain heavy chain amino acid sequence of SEQ ID NO:87. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:77 and framework regions having an amino acid sequence at least 90% identical, at least 93% identical or at least 95% identical to the amino acid sequence of the framework regions of the variable domain light chain amino acid sequence of SEQ ID NO:77 and a humanized heavy chain variable domain comprising the CDRs of SEQ ID NO:88 and framework regions having an amino acid sequence at least 90% identical, at least 93% identical or at least 95% identical to the amino acid sequence of the framework regions of the variable domain heavy chain amino acid sequence of SEQ ID NO:88. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:80 and framework regions having an amino acid sequence at least 90% identical, at least 93% identical or at least 95% identical to the amino acid sequence of the framework regions of the variable domain light chain amino acid sequence of SEQ ID NO:80 and a humanized heavy chain variable domain comprising the CDRs of SEQ ID NO:87 and framework regions having an amino acid sequence at least 90% identical, at least 93% identical or at least 95% identical to the amino acid sequence of the framework regions of the variable domain heavy chain amino acid sequence of SEQ ID NO:87. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:86 and framework regions having an amino acid sequence at least 90% identical, at least 93% identical or at least 95% identical to the amino acid sequence of the framework regions of the variable domain light chain amino acid sequence of SEQ ID NO:86 and a humanized heavy chain variable domain comprising the CDRs of SEQ ID NO:100 and framework regions having an amino acid sequence at least 90% identical, at least 93% identical or at least 95% identical to the amino acid sequence of the framework regions of the variable domain heavy chain amino acid sequence of SEQ ID NO:100. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:85 and framework regions having an amino acid sequence at least 90% identical, at least 93% identical or at least 95% identical to the amino acid sequence of the framework regions of the variable domain light chain amino acid sequence of SEQ ID NO:85 and a humanized heavy chain variable domain comprising the CDRs of SEQ ID NO:101 and framework regions having an amino acid sequence at least 90% identical, at least 93% identical or at least 95% identical to the amino acid sequence of the framework regions of the variable domain heavy chain amino acid sequence of SEQ ID NO:101. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:85 and framework regions having an amino acid sequence at least 90% identical, at least 93% identical or at least 95% identical to the amino acid sequence of the framework regions of the variable domain light chain amino acid sequence of SEQ ID NO:85 and a humanized heavy chain variable domain comprising the CDRs of SEQ ID NO:100 and framework regions having an amino acid sequence at least 90% identical, at least 93% identical or at least 95% identical to the amino acid sequence of the framework regions of the variable domain heavy chain amino acid sequence of SEQ ID NO:100. In one embodiment, the anti-IL-36R antibody is a humanized monoclonal antibody.

In some specific embodiments, the humanized anti-IL-36R antibodies disclosed herein comprise at least a heavy or a light chain variable domain comprising the CDRs or HVLs of the murine monoclonal antibodies or humanized antibodies as disclosed herein and the FRs of the human germline heavy and light chain variable domains.

In one further aspect, the present invention provides an anti-IL-36R antibody or antigen-binding fragment thereof comprising a light chain CDR1 (L-CDR1) sequence of any one of SEQ ID NO:21-29; a light chain CDR2 (L-CDR2) sequence of any one of SEQ ID NO:30-38; a light chain CDR3 (L-CDR3) sequence of any one of SEQ ID NO:39-47; a heavy chain CDR1 (H-CDR1) sequence of any one of SEQ ID NO:48-56; a heavy chain CDR2 (H-CDR2) sequence of any one of SEQ ID NO:57-66; and a heavy chain CDR3 (H-CDR3) sequence of any one of SEQ ID NO:67-75. In one aspect, the anti-IL-36R antibody or antigen-binding fragment thereof comprises a light chain variable region comprising a L-CDR1 listed above, a L-CDR2 listed above and a L-CDR3 listed above, and a heavy chain variable region comprising a H-CDR1 listed above, a H-CDR2 listed above and a H-CDR3 listed above.

In a further aspect, the present invention provides an anti-IL-36R antibody or antigen-binding fragment thereof comprising:
  a) a L-CDR1, a L-CDR2, a L-CDR3, a H-CDR1, a H-CDR2 and a H-CDR3 sequence of SEQ ID NO:21, 30, 39, 48, 57 and 67, respectively; or
  b) a L-CDR1, a L-CDR2, a L-CDR3, a H-CDR1, a H-CDR2 and a H-CDR3 sequence of SEQ ID NO:22, 31, 40, 49, 58 and 68, respectively; or
  c) a L-CDR1, a L-CDR2, a L-CDR3, a H-CDR1, a H-CDR2 and a H-CDR3 sequence of SEQ ID NO:23, 32, 41, 50, 59 and 69, respectively; or
  d) a L-CDR1, a L-CDR2, a L-CDR3, a H-CDR1, a H-CDR2 and a H-CDR3 sequence of SEQ ID NO:24, 33, 42, 51, 60 and 70, respectively; or
  e) a L-CDR1, a L-CDR2, a L-CDR3, a H-CDR1, a H-CDR2 and a H-CDR3 sequence of SEQ ID NO:25, 34, 43, 52, 61 and 71, respectively; or
  f) a L-CDR1, a L-CDR2, a L-CDR3, a H-CDR1, a H-CDR2 and a H-CDR3 sequence of SEQ ID NO:26, 35, 44, 53, 62 and 72, respectively; or
  g) a L-CDR1, a L-CDR2, a L-CDR3, a H-CDR1, a H-CDR2 and a H-CDR3 sequence of SEQ ID NO:27, 36, 45, 54, 63 and 73, respectively; or
  h) a L-CDR1, a L-CDR2, a L-CDR3, a H-CDR1, a H-CDR2 and a H-CDR3 sequence of SEQ ID NO:27, 36, 45, 54, 64 and 74, respectively; or
  i) a L-CDR1, a L-CDR2, a L-CDR3, a H-CDR1, a H-CDR2 and a H-CDR3 sequence of SEQ ID NO:27, 36, 45, 54, 64 and 73, respectively; or
  j) a L-CDR1, a L-CDR2, a L-CDR3, a H-CDR1, a H-CDR2 and a H-CDR3 sequence of SEQ ID NO:28, 37, 46, 55, 65 and 74, respectively; or
  k) a L-CDR1, a L-CDR2, a L-CDR3, a H-CDR1, a H-CDR2 and a H-CDR3 sequence of SEQ ID NO:29, 38, 47, 56, 66 and 75, respectively.

In a further aspect, the present invention provides an anti-IL-36R antibody or antigen-binding fragment thereof comprising:
  a) a L-CDR1, a L-CDR2, a L-CDR3, a H-CDR1, a H-CDR2 and a H-CDR3 sequence of SEQ ID NO:26, 103, 44, 53, 62 and 72, respectively; or
  b) a L-CDR1, a L-CDR2, a L-CDR3, a H-CDR1, a H-CDR2 and a H-CDR3 sequence of SEQ ID NO:26, 104, 44, 53, 62 and 72, respectively; or
  c) a L-CDR1, a L-CDR2, a L-CDR3, a H-CDR1, a H-CDR2 and a H-CDR3 sequence of SEQ ID NO:27, 36, 45, 107, 63 and 73, respectively; or
  d) a L-CDR1, a L-CDR2, a L-CDR3, a H-CDR1, a H-CDR2 and a H-CDR3 sequence of SEQ ID NO:27, 36, 45, 107, 64 or 73, respectively.

In one aspect, the anti-IL-36R antibody or antigen-binding fragment thereof comprises a light chain variable region comprising a L-CDR1, L-CDR2 and L-CDR3 combination listed above, and a heavy chain variable region comprising a H-CDR1, H-CDR2 and H-CDR3 combination listed above.

In specific embodiments, it is contemplated that chimeric antibodies with switched CDR regions (i.e., for example switching one or two CDRs of one of the mouse antibodies or humanized antibody derived therefrom with the analogous CDR from another mouse antibody or humanized antibody derived therefrom) between these exemplary immunoglobulins may yield useful antibodies.

In certain embodiments, the humanized anti-IL-36R antibody is an antibody fragment. Various antibody fragments have been generally discussed above and there are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from *E. coli* and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner.

Accordingly, in one aspect, the present invention provides antibody fragments comprising the CDRs described herein, in particular one of the combinations of L-CDR1, L-CDR2, L-CDR3, H-CDR1, H-CDR2 and H-CDR3 described herein. In a further aspect, the present invention provides antibody fragments comprising the variable regions described herein, for example one of the combinations of light chain variable regions and heavy chain variable regions described herein.

Certain embodiments include an F(ab')$_2$ fragment of a humanized anti-IL-36R antibody comprise a light chain sequence of any of SEQ ID NO: 115 or 118 in combination with a heavy chain sequence of SEQ ID NO: 125, 126 or 127. Such embodiments can include an intact antibody comprising such an F(ab')$_2$.

Certain embodiments include an F(ab')$_2$ fragment of a humanized anti-IL-36R antibody comprise a light chain sequence of any of SEQ ID NO: 123 or 124 in combination with a heavy chain sequence of SEQ ID NO: 138 or 139. Such embodiments can include an intact antibody comprising such an F(ab')$_2$.

In some embodiments, the antibody or antibody fragment includes a constant region that mediates effector function. The constant region can provide antibody-dependent cellular cytotoxicity (ADCC), antibody-dependent cellular phagocytosis (ADCP) and/or complement-dependent cytotoxicity (CDC) responses against an IL-36R expressing target cell. The effector domain(s) can be, for example, an Fc region of an Ig molecule.

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of IgM≈IgG$_1$≈IgG$_3$>IgG$_2$>IgG$_4$ and $IgG_1 \approx IgG_3 > IgG_2/IgM/Iga_4$, respectively. Murine immunoglobulins mediate CDC and ADCC/ADCP generally in the order of murine $IgM \approx IgG_3 >> IgG_{2b} > IgG_{2a} >> IgG_1$ and $IgG_{2b} > IgG_{2a} > IgG_1 >> IgG_3$, respectively. In another example, murine $IgG_{2a}$ mediates ADCC while both murine $IgG_{2a}$ and IgM mediate CDC.

Antibody Modifications

The humanized anti-IL-36R antibodies and agents can include modifications of the humanized anti-IL-36R antibody or antigen-binding fragment thereof. For example, it may be desirable to modify the antibody with respect to effector function, so as to enhance the effectiveness of the antibody in treating cancer. One such modification is the introduction of cysteine residue(s) into the Fc region, thereby allowing interchain disulfide bond formation in this region. The homodimeric antibody thus generated can have improved internalization capability and/or increased complement-mediated cell killing and/or antibody-dependent cellular cytotoxicity (ADCC). See, for example, Caron et al., 1992, J. Exp Med. 176:1191-1195; and Shopes, 1992, J. Immunol. 148:2918-2922. Homodimeric antibodies having enhanced anti-tumor activity can also be prepared using heterobifunctional cross-linkers as described in Wolff et al., 1993, Cancer Research 53: 2560-2565. Alternatively, an antibody can be engineered to contain dual Fc regions, enhancing complement lysis and ADCC capabilities of the antibody. See Stevenson et al., 1989, Anti-Cancer Drug Design 3: 219-230.

Antibodies with improved ability to support ADCC have been generated by modifying the glycosylation pattern of their Fc region. This is possible since antibody glycosylation at the asparagine residue, N297, in the $C_{H2}$ domain is involved in the interaction between IgG and Fcγ receptors prerequisite to ADCC. Host cell lines have been engineered to express antibodies with altered glycosylation, such as increased bisecting N-acetylglucosamine or reduced fucose. Fucose reduction provides greater enhancement to ADCC activity than does increasing the presence of bisecting N-acetylglucosamine. Moreover, enhancement of ADCC by low fucose antibodies is independent of the FcγRIIIa V/F polymorphism.

Modifying the amino acid sequence of the Fc region of antibodies is an alternative to glycosylation engineering to enhance ADCC. The binding site on human $IgG_1$ for Fcγ receptors has been determined by extensive mutational analysis. This led to the generation of humanized $IgG_1$ antibodies with Fc mutations that increase the binding affinity for FcγRIIIa and enhance ADCC in vitro. Additionally, Fc variants have been obtained with many different permutations of binding properties, e.g., improved binding to specific FcγR receptors with unchanged or diminished binding to other FcγR receptors.

Another aspect includes immunoconjugates comprising the humanized antibody or fragments thereof conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used to form useful immunoconjugates include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, the tricothecenes, and the like. A variety of radionuclides are available for the production of radioconjugated humanized anti-IL-36R antibodies. Examples include $^{212}Bi$, $^{131}I$, $^{131}In$, $^{90}Y$, and $^{186}Re$.

Conjugates of the humanized anti-IL-36R antibody and cytotoxic or chemotherapeutic agent can be made by known methods, using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., 1987, Science 238:1098. Carbon-14-labeled 1-isothiocyanatobenzyl-3-methyldiethylene triaminepentaacetic acid (MX-DTPA) is an exemplary chelating agent for conjugation of radionucleotide to the antibody. Conjugates also can be formed with a cleavable linker.

The humanized anti-IL-36R antibodies disclosed herein can also be formulated as immunoliposomes. Liposomes containing the antibody are prepared by methods known in the art, such as described in Epstein et al., 1985, Proc. Natl. Acad. Sci. USA 82:3688; Hwang et al., 1980, Proc. Natl. Acad. Sci. USA 77:4030; and U.S. Pat. Nos. 4,485,045 and 4,544,545. Liposomes having enhanced circulation time are disclosed, for example, in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody disclosed herein can be conjugated to the liposomes as described in Martin et al., 1982, J. Biol. Chem. 257:286-288 via a disulfide interchange reaction. A chemotherapeutic agent (such as doxorubicin) is optionally contained within the liposome. See, e.g., Gabizon et al., 1989, J. National Cancer Inst. 81(19):1484.

The antibodies described and disclosed herein can also be used in ADEPT (Antibody-Directed Enzyme Prodrug Therapy) procedures by conjugating the antibody to a prodrug-activating enzyme that converts a prodrug (e.g., a peptidyl chemotherapeutic agent), to an active anti-cancer drug. See, for example, WO 81/01145, WO 88/07378, and U.S. Pat. No. 4,975,278. The enzyme component of the immunoconjugate useful for ADEPT is an enzyme capable of acting on a prodrug in such a way so as to covert it into its more active, cytotoxic form. Specific enzymes that are useful in ADEPT include, but are not limited to, alkaline phosphatase for converting phosphate-containing prodrugs into free drugs; arylsulfatase for converting sulfate-containing prodrugs into free drugs; cytosine deaminase for converting non-toxic 5-fluorocytosine into the anti-cancer drug, 5-fluorouracil; proteases, such as *serratia* protease, thermolysin, subtilisin, carboxypeptidases, and cathepsins (such as cathepsins B and L), for converting peptide-containing prodrugs into free drugs; D-alanylcarboxypeptidases, for converting prodrugs containing D-amino acid substituents; carbohydrate-cleaving enzymes such as β-galactosidase and neuraminidase for converting glycosylated prodrugs into free drugs; β-lactamase for converting drugs derivatized with β-lactams into free drugs; and penicillin amidases, such as penicillin V amidase or penicillin G amidase, for converting drugs derivatized at their amine nitrogens with phenoxyacetyl or phenylacetyl groups, respectively, into free drugs. Alternatively, antibodies having enzymatic activity ("abzymes") can be used to convert the prodrugs into free active drugs (see, for example, Massey, 1987, Nature 328: 457-458). Antibody-abzyme conjugates can be prepared by known methods for delivery of the abzyme to a tumor cell population, for example, by covalently binding the enzyme to the humanized anti-IL-36R antibody/heterobifunctional crosslinking reagents discussed above. Alternatively, fusion proteins comprising at least the antigen binding region of an antibody disclosed herein linked to at least a functionally active portion of an enzyme as described above can be constructed using recombinant DNA techniques (see, e.g., Neuberger et al., 1984, Nature 312:604-608).

In certain embodiments, it may be desirable to use a humanized anti-IL-36R antibody fragment, rather than an intact antibody, to increase tissue penetration, for example. It may be desirable to modify the antibody fragment in order to increase its serum half life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, covalent modifications of the humanized anti-IL-36R antibody are also included. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. No. 4,640,835, U.S. Pat. No. 4,496,689, U.S. Pat. No. 4,301,144, U.S. Pat. No. 4,670,417, U.S. Pat. No. 4,791,192 and U.S. Pat. No. 4,179,337.

Humanization and Amino Acid Sequence Variants

Amino acid sequence variants of the anti-IL-36R antibody can be prepared by introducing appropriate nucleotide changes into the anti-IL-36R antibody DNA, or by peptide synthesis. Such variants include, for example, deletions from, and/or insertions into and/or substitutions of, residues within the amino acid sequences of the anti-IL-36R antibodies of the examples herein. Any combination of deletions, insertions, and substitutions is made to arrive at the final construct, provided that the final construct possesses the desired characteristics. The amino acid changes also may alter post-translational processes of the humanized or variant anti-IL-36R antibody, such as changing the number or position of glycosylation sites.

A useful method for identification of certain residues or regions of the anti-IL-36R antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with IL-36R antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-IL-36R antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-IL-36R antibody fused to an epitope tag. Other insertional variants of the anti-IL-36R antibody molecule include a fusion to the N- or C-terminus of the anti-IL-36R antibody of an enzyme or a polypeptide which increases the serum half-life of the antibody.

Another type of variant is an amino acid substitution variant. These variants have at least one amino acid residue in the anti-IL-36R antibody molecule removed and a different residue inserted in its place. The sites of greatest interest for substitutional mutagenesis include the hypervariable regions, but FR alterations are also contemplated. Conservative substitutions are shown in Table 5 under the heading of "preferred substitutions". If such substitutions result in a change in biological activity, then more substantial changes, denominated "exemplary substitutions", or as further described below in reference to amino acid classes, may be introduced and the products screened.

TABLE C

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |

TABLE C-continued

| Original Residue | Exemplary Substitutions | Preferred Substitutions |
|---|---|---|
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-IL-36R antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human IL-36R. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

In some embodiments, it may be desirable to modify the antibodies of the invention to add glycosylations sites. Glycosylation of antibodies is typically either N-linked or 0-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IL-36R antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-IL-36R antibody.

Polynucleotides, Vectors, Host Cells, and Recombinant Methods

Other embodiments encompass isolated polynucleotides that comprise a sequence encoding a humanized anti-IL-36R antibody, vectors, and host cells comprising the polynucleotides, and recombinant techniques for production of the humanized antibody. The isolated polynucleotides can encode any desired form of the anti-IL-36R antibody including, for example, full length monoclonal antibodies, Fab, Fab', F(ab')$_2$, and Fv fragments, diabodies, linear antibodies, single-chain antibody molecules, and multispecific antibodies formed from antibody fragments.

Some embodiments include isolated polynucleotides comprising sequences that encode the light chain variable region of an antibody or antibody fragment having the amino acid sequence of any of SEQ ID NO: SEQ ID NO:1-10. Some embodiments include isolated polynucleotides comprising sequences that encode the heavy chain variable region of an antibody or antibody fragment having the amino acid sequence of SEQ ID NO:11-20.

Some embodiments include isolated polynucleotides comprising sequences that encode the light chain variable region of an antibody or antibody fragment having the amino acid sequence of any of SEQ ID NO:76-86. Some embodiments include isolated polynucleotides comprising sequences that encode the heavy chain variable region of an antibody or antibody fragment having the amino acid sequence of SEQ ID NO: 87-101.

Some embodiments include isolated polynucleotides comprising sequences that encode the light chain of an antibody having the amino acid sequence of any of SEQ ID NO:114-124. Some embodiments include isolated polynucleotides comprising sequences that encode the heavy chain of an antibody having the amino acid sequence of SEQ ID NO:125-139.

In one aspect, the isolated polynucleotide sequence(s) encodes an antibody or antibody fragment having a light chain and a heavy chain variable region comprising the amino acid sequences of SEQ ID NO:115 and SEQ ID NO:127, respectively; SEQ ID NO:118 and SEQ ID NO:126, respectively; SEQ ID NO:118 and SEQ ID NO:127, respectively; SEQ ID NO:115 and SEQ ID NO:125, respectively; SEQ ID NO:115 and SEQ ID NO:126, respectively; SEQ ID NO:118 and SEQ ID NO:125, respectively; SEQ ID NO:124 and SEQ ID NO:138, respectively; SEQ ID NO:123 and SEQ ID NO:139, respectively; SEQ ID NO:123 and SEQ ID NO:138, respectively.

The polynucleotide(s) that comprise a sequence encoding a humanized anti-IL-36R antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The humanized anti-IL-36R antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the humanized anti-IL-36R antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-IL-36R antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-v. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-IL-36R antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-IL-36R antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-IL-36R antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-IL-36R antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Humanized anti-IL-36R antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the Rous sarcoma virus long terminal repeat can be used as the promoter.

Another useful element that can be used in a recombinant expression vector is an enhancer sequence, which is used to increase the transcription of a DNA encoding a humanized anti-IL-36R antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the humanized anti-IL-36R antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-IL-36R antibody. One useful transcription termination component is the bovine growth hormone polyadenylation region. See WO94/11026 and the expression vector disclosed therein. In some embodiments, humanized anti-IL-36R antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for humanized anti-IL-36Rantibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia* pastors (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated humanized anti-IL-36R antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

In another aspect, expression of humanized anti-IL-36R is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for humanized anti-IL-36R antibody production and cultured in conventional nutrient media modified as appropriate for inducing promoters, selecting transformants, or amplifying the genes encoding the desired sequences.

The host cells used to produce a humanized anti-IL-36R antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. No. 4,767,704, U.S. Pat. No. 4,657,866, U.S. Pat. No. 4,927,762, U.S. Pat. No. 4,560,655, U.S. Pat. No. 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present invention. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-IL-36R polypeptide (e.g., a heavy chain or light chain variable region), or its complement. Hybridizing nucleic acids of the type described herein can be used, for example, as a cloning probe, a primer, e.g., a PCR primer, or a diagnostic probe.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the IL-36R protein (or fragment thereof) to be purified, and thereafter the support is washed with a suitable solvent that will remove substantially all the material in the sample except the IL-36R protein, which is bound to the immobilized antibody. Finally, the support is washed with another suitable solvent that will release the IL-36R protein from the antibody.

Anti-IL-36R antibodies, for example humanized anti-IL-36R antibodies, are also useful in diagnostic assays to detect and/or quantify IL-36R protein, for example, detecting IL-36R expression in specific cells, tissues, or serum. The anti-IL-36R antibodies can be used diagnostically to, for example, monitor the development or progression of a disease as part of a clinical testing procedure to, e.g., determine the efficacy of a given treatment and/or prevention regimen. Detection can be facilitated by coupling the anti-IL-36R antibody. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention.

The anti-IL-36R antibodies can be used in methods for diagnosing an IL-36R-associated disorder (e.g., a disorder characterized by abnormal expression of IL-36R) or to determine if a subject has an increased risk of developing an IL-36R-associated disorder. Such methods include contacting a biological sample from a subject with an IL-36R antibody and detecting binding of the antibody to IL-36R. By "biological sample" is intended any biological sample obtained from an individual, cell line, tissue culture, or other source of cells potentially expressing IL-36R. Methods for obtaining tissue biopsies and body fluids from mammals are well known in the art.

In some embodiments, the method can further comprise comparing the level of IL-36R in a patient sample to a control sample (e.g., a subject that does not have an IL-36R-associated disorder) to determine if the patient has an IL-36R-associated disorder or is at risk of developing an IL-36R-associated disorder.

It will be advantageous in some embodiments, for example, for diagnostic purposes to label the antibody with a detectable moiety. Numerous detectable labels are available, including radioisotopes, fluorescent labels, enzyme substrate labels and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}S$, $^{14}C$, $^{125}I$, $^{3}H$, and $^{131}I$. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, for example. Fluorescence can be quantified using a fluorimeter.

There are various well-characterized enzyme-substrate labels known in the art (see, e.g., U.S. Pat. No. 4,275,149 for a review). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methylumbelliferyl-β-D-galactosidase.

Numerous other enzyme-substrate combinations are available to those skilled in the art. For a general review of these, see U.S. Pat. No. 4,275,149 and U.S. Pat. No. 4,318,980.

In another embodiment, the humanized anti-IL-36R antibody is used unlabeled and detected with a labeled antibody that binds the humanized anti-IL-36R antibody.

The antibodies described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

The anti-IL-36R antibody or antigen binding fragment thereof can be used to inhibit the binding of ligand to the IL-36 receptor. Such methods comprise administering an anti-IL-36R antibody or antigen binding fragment thereof to a cell (e.g., a mammalian cell) or cellular environment, whereby signaling mediated by the IL-36 receptor is inhibited. These methods can be performed in vitro or in vivo. By "cellular environment" is intended the tissue, medium, or extracellular matrix surrounding a cell. The anti-IL-36R antibody or antigen binding fragment thereof is administered to the cellular environment of a cell in such a manner that the antibody or fragment is capable of binding to IL-36R molecules outside of and surrounding the cell, therefore, preventing the binding of IL-36 ligand to its receptor.

Diagnostic Kits

An anti-IL-36R antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Therapeutic Uses

In another embodiment, a humanized anti-IL-36R antibody disclosed herein is useful in the treatment of various disorders associated with the expression of IL-36R as described herein. Methods for treating an IL-36R associated disorder comprise administering a therapeutically effective amount of a humanized anti-IL-36R antibody to a subject in need thereof.

The humanized anti-IL-36R antibody or agent is administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). The humanized anti-IL-36R antibody or agent can be administered, for example, as an infusion or as a bolus. Parenteral infusions include intramuscular, intravenous, intraarterial, intraperitoneal, or subcutaneous administration. In addition, the humanized anti-IL-36R antibody is suitably administered by pulse infusion, particularly with declining doses of the antibody. In one aspect, the dosing is given by injections, most preferably intravenous or subcutaneous injections, depending in part on whether the administration is brief or chronic.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 20 mg/kg (e.g., 0.1-15 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is that disclosed in WO 94/04188.

The term "suppression" is used herein in the same context as "amelioration" and "alleviation" to mean a lessening of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with IL-36R expression.

The antibody need not be, but is optionally, formulated with one or more agents currently used to prevent or treat the disorder in question. The effective amount of such other agents depends on the amount of humanized anti-IL-36R23p19 antibody present in the formulation, the type of disorder or treatment, and other factors discussed above. These are generally used in the same dosages and with administration routes as used hereinbefore or about from 1 to 99% of the heretofore employed dosages.

Pharmaceutical Compositions and Administration Thereof

A composition comprising an IL-36R binding agent (e.g., an anti-IL-36R antibody) can be administered to a subject having or at risk of having an immunological disorder, respiratory disorder or a cancer. The invention further provides for the use of a IL-36R binding agent (e.g., an anti-IL-36R antibody) in the manufacture of a medicament for prevention or treatment of a cancer, respiratory disorder or immunological disorder. The term "subject" as used herein means any mammalian patient to which an IL-36Rbinding agent can be administered, including, e.g., humans and non-human mammals, such as primates, rodents, and dogs. Subjects specifically intended for treatment using the methods described herein include humans. The antibodies or agents can be administered either alone or in combination with other compositions in the prevention or treatment of the immunological disorder, respiratory disorder or cancer. Such compositions which can be administered in combination with the antibodies or agents include methotrexate (MTX) and immunomodulators, e.g. antibodies or small molecules.

Examples of antibodies for use in such pharmaceutical compositions are those that comprise a antibody or antibody fragment having the light chain variable region amino acid sequence of any of SEQ ID NO: 1-10. Examples of antibodies for use in such pharmaceutical compositions are also those that comprise a humanized antibody or antibody fragment having the heavy chain variable region amino acid sequence of any of SEQ ID NO: 11-20.

Further examples of antibodies for use in such pharmaceutical compositions are also those that comprise a humanized antibody or antibody fragment having the light chain variable region amino acid sequence of any of SEQ ID NO:76-86. Preferred antibodies for use in such pharmaceutical compositions are also those that comprise a humanized antibody or antibody fragment having the heavy chain variable region amino acid sequence of any of SEQ ID NO:87-101.

Further examples of antibodies for use in such pharmaceutical compositions are also those that comprise a humanized antibody or antibody fragment having the light chain variable region and heavy chain variable region of any of SEQ ID NO: 77 and 89, SEQ ID NO: 80 and 88, SEQ ID NO: 80 and 89, SEQ ID NO: 77 and 87, SEQ ID NO: 77 and 88, SEQ ID NO: 80 and 87, SEQ ID NO: 86 and 100, SEQ ID NO: 85 and 101, or SEQ ID NO: 85 and 10.

Further examples of antibodies for use in such pharmaceutical compositions are also those that comprise a humanized antibody having the light chain region amino acid sequence of any of SEQ ID NO:115, 118, 123 or 124. Preferred antibodies for use in such pharmaceutical compositions are also those that comprise humanized antibody having the heavy chain variable region amino acid sequence of any of SEQ ID NO:125, 126, 127, 138 or 139.

Further examples of antibodies for use in such pharmaceutical compositions are also those that comprise Antibody B1, Antibody B2, Antibody B3, Antibody B4, Antibody B5, Antibody B6, Antibody C1, Antibody C2 or Antibody C3.

Various delivery systems are known and can be used to administer the IL-36R binding agent. Methods of introduction include but are not limited to intradermal, intramuscular, intraperitoneal, intravenous, subcutaneous, intranasal, epidural, and oral routes. The IL-36R binding agent can be administered, for example by infusion, bolus or injection, and can be administered together with other biologically active agents such as chemotherapeutic agents. Administration can be systemic or local. In preferred embodiments, the administration is by subcutaneous injection. Formulations for such injections may be prepared in for example prefilled syringes that may be administered once every other week.

In specific embodiments, the IL-36R binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-IL-36R antibody or agent does not absorb are used.

In other embodiments, the anti-IL-36R antibody or agent is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

An IL-36R binding agent (e.g., an anti-IL-36R antibody) can be administered as pharmaceutical compositions comprising a therapeutically effective amount of the binding agent and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a IL-36R binding agent (e.g., an anti-IL-36R antibody) in lyophilized form and (b) a second container containing a pharmaceutically acceptable diluent (e.g., sterile water) for injection. The pharmaceutically acceptable diluent can be used for reconstitution or dilution of the lyophilized anti-IL-36R antibody or agent. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the IL-36R binding agent (e.g., anti-IL-36R antibody) that is effective in the treatment or prevention of an immunological disorder or cancer can be determined by standard clinical techniques. In addition, in vitro assays may optionally be employed to help identify optimal dosage ranges. The precise dose to be employed in the formulation will also depend on the route of administration, and the stage of immunological disorder or cancer, and should be decided according to the judgment of the practitioner and each patient's circumstances. Effective doses may be extrapolated from dose-response curves derived from in vitro or animal model test systems.

Generally, the dosage of an anti-IL-36R antibody or IL-36R binding agent administered to a patient with an immunological disorder or IL-36R-expressing cancer is typically about 0.1 mg/kg to about 100 mg/kg of the subject's body weight. The dosage administered to a subject is about 0.1 mg/kg to about 50 mg/kg, about 1 mg/kg to about 30 mg/kg, about 1 mg/kg to about 20 mg/kg, about 1 mg/kg to about 15 mg/kg, or about 1 mg/kg to about 10 mg/kg of the subject's body weight.

Exemplary doses include, but are not limited to, from 1 ng/kg to 100 mg/kg. In some embodiments, a dose is about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 16 mg/kg. The dose can be administered, for example, daily, once per week (weekly), twice per week, thrice per week, four times per week, five times per week, six times per week, biweekly or monthly, every two months, or every three months. In specific embodiments, the dose is about 0.5 mg/kg/week, about 1 mg/kg/week, about 2 mg/kg/week, about 3 mg/kg/week, about 4 mg/kg/week, about 5 mg/kg/week, about 6 mg/kg/week, about 7 mg/kg/week, about 8 mg/kg/week, about 9 mg/kg/week, about 10 mg/kg/week, about 11 mg/kg/week, about 12 mg/kg/week, about 13 mg/kg/week, about 14 mg/kg/week, about 15 mg/kg/week or about 16 mg/kg/week. In some embodiments, the dose ranges from about 1 mg/kg/week to about 15 mg/kg/week.

In some embodiments, the pharmaceutical compositions comprising the IL-36R binding agent can further comprise a therapeutic agent, either conjugated or unconjugated to the binding agent. The anti-IL-36R antibody or IL-36R binding agent can be co-administered in combination with one or more therapeutic agents for the treatment or prevention of immunological disorders or cancers.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-IL-36R antibody or IL-36R binding agent is administered concurrently with a therapeutic agent. In another specific embodiment, the therapeutic agent is administered prior or subsequent to administration of the anti-IL-36R antibody or IL-36R binding agent, by at least an hour and up to several months, for example at least an hour, five hours, 12 hours, a day, a week, a month, or three months, prior or subsequent to administration of the anti-IL-36R antibody or IL-36R binding agent.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the humanized anti-IL-36R antibody. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

The antibodies of the present invention are further described in the Examples below.

EXAMPLES

Example 1: Identification of Anti-Human IL-36R Antibodies

Multiple mouse strains were immunized with recombinantly produced human IL-36R (ECD—extracellular domain: amino acids 20-332 of Genbank Accession #NP_003845) protein and those which generated a strong titer response taken into traditional hybridoma generation. Fusion products eliciting a strong binding to human IL-36R (ECD) yet no binding to human IL-1R1 (the most related IL-1R family member) were subcloned and re-screened. Multiple hybridomas were identified to yield monoclonal antibodies which bound and neutralized signaling from IL-36R (see examples 2, 3, and 4). Variable domains were cloned from the hybridomas using standard PCR primer sets. The variable domains and specific CDRs of representative monoclonal antibodies are described above. All of the mouse antibodies were converted to chimeric antibodies consisting of the mouse variable domains on human constant domains (hu IgG1KO/kappa). The hu IgG1KO (knock out) has two replacement mutations (Leu234Ala and Leu235Ala) that eliminate ADCC and CDC activity by reducing effector functions such as FcγR and complement binding. The variable domains of the mouse and chimeric antibodies are identical. Chimeric antibodies are generated to confirm the function of the antibody and to ensure the correct variable domain sequence has been obtained.

Example 2: Molecular Binding Affinities of Identified Mouse Anti-Human IL-36R Antibodies A) Kinetics and binding affinities of anti-IL-36R antibodies binding to recombinant human IL-36R were measured using the PROTEON, surface plasmon resonance, (Bio-Rad, Hercules, Calif.) using material generated from hybridoma following single column purification. The binding affinities of all the mouse leads to human IL-36R run at a single IL-36R surface coat concentration was estimated to be <100 pM. The binding affinities of the mouse antibodies to human IL-36R run at 7 different surface densities (globally fit) is shown in Table 1. Binding of the chimeric anti-IL36R IgGs is equivalent to the respective mouse leads.

TABLE 1

Binding affinity of mouse anti-human IL-36R antibodies.

| Lead | Binding $K_D$ (pM) |
| --- | --- |
| Mouse 73C5 | 57 |
| Mouse 73F6 | 25 |
| Mouse 78C8 | 63 |
| Mouse 81A1 | 16 |
| Mouse 81B4 | 24 |
| Mouse 33D10 | 9 |

B) Molecular Selectivity Over Mouse IL-36R and Human IL-1R1

The mouse and chimeric anti-IL-36R antibodies were also injected over either a mouse IL-36R or a human IL-1R1 surface at a concentration of 100 nM. The binding signal to mouse IL-36R and to human IL-1R1 for these antibodies measured using the Fortebio OCTET, bio-layer interferometry, (Fortebio, Menlo Park, Calif.) is zero, which indicates these antibodies selectively bind to human IL-36R. The binding of the anti-IL-36R antibodies to human IL-36R was also analyzed in the presence of 50% human serum and no significant effect of serum on binding on-rate was observed demonstrating high specificity.

Example 3: Potency of Mouse and Chimeric Anti-Human IL-36R Antibodies in Functional Human and Cynomolgus Assays Protocols: Human NCI/ADR-RES Cells pNFκB/Cytokine Release Assays
Reagents:
R&D Systems: truncated rh IL36β
R&D Systems: truncated rh IL36γ

R&D Systems: truncated rh IL36α:
MA6000 Phospho-NFκB (Ser536) Whole Cell Lysate Kit
Meso Scale Diagnostics, LLC
MSD ELISA custom human 96-well 4-spot assay
Meso Scale Diagnostics, LLC NCI/ADR-RES cells were plated at 45000 cells/well, in RPMI media with 0.25% serum in a 96 well plate. One plate was utilized for the analysis of pNFκB and another for cytokine release. The plates were then incubated overnight at 37° C., 5% $CO_2$. Ligands (IL36α, β, or γ) and antibodies were diluted at 4× desired concentration in serum starved (SS) media. Antagonists (antibodies) were added to cells prior to ligand. For pNFκB: NCI cells+/−ligand and antagonist were incubated for 1 hour, 37° C., 5% $CO_2$. Media was then aspirated and cells were lysed in 100 μl/well Complete lysis Buffer on ice 30 min. Lysate was then centrifuged at 2500 RPM, 20 min, 4° C., and transferred to an MSD ELISA plate and assayed for pNFκB as per the manufacturer's protocol. For Cytokine release: 18-24 hours after stimulation, supernatants were transferred to an MSD ELISA plate and assayed for cytokine as per manufacturer's protocol.

Protocol: pNFκB (S536) MSD ELISA for BaF/3 Cynomolgus IL-36R Cells

BaF/3 cynomolgus IL-36R cells were plated at 90,000 cells/well in SS media in a 96 well plate. 100 ul media was added to control wells. Antagonists (antibodies) were diluted at 4× desired concentration and 50 μl was added to each well. Ligands (IL36α, β, or γ) were diluted at 4× desired concentration in SS media and 50 μl were added to each well (for final volume of 200 μl). Plates were incubated for 15 min, 37° C., 5% $CO_2$. Plates were centrifuged briefly, media was aspirated and cells were lysed in 100 μl/well Complete Lysis Buffer (see MSD pNFκB protocol) and incubated on ice 30 min. Lysates were then centrifuged at 2500 RPM, 20 min, 4° C. and transferred to an MSD ELISA plate. Lysates were then evaluated for pNFκB activity using the MSD kit as described above.

Results: $IC_{90}$ results for mouse anti-human IL-36R antibodies in human functional assays (pNFκB and cytokine release) and a cynomolgus functional assay (pNFκB) with human IL-36 ligands are shown in Table 2. $IC_{90}$ results for chimeric anti-human IL-36R antibodies in human functional assays (pNFκB and cytokine release) and a cynomolgus functional assay (pNFκB) with human IL-36 ligands are shown in Table 3.

TABLE 2

Potency of mouse antibodies in functional cell assays
(isotype controls demonstrated no inhibition of activity
at highest concentration tested for samples)

| NCI/ADR-RES | | 33D10 | 73C5 | 73F6F8 | 76E10E8 | 78C8D1 | 81A1D1 | 81B4E11 | 89A12B8 | 172C8B12 | 67E7E8 |
|---|---|---|---|---|---|---|---|---|---|---|---|
| pNFκB | trun-IL-36a IC90 (nM) | 1.7 | 3.4 | 2.8 | ND | 5.8 | 2.7 | 1.7 | ND | ND | ND |
| | trun-IL-36b IC90 (nM) | 1.3 | 3.4 | 3 | ND | 6.8 | 4.2 | 1.4 | ND | ND | ND |
| | trun-IL-36g IC90 (nM) | 1.1 | 2.5 | 1.5 | 1.9 | 4.6 | 2.2 | 1.2 | 145 | 3.8 | >67 |
| GM-CSF | trun-IL-36a IC90 (nM) | 0.8 | 4.8 | 5.9 | ND | 7.1 | 1.2 | 0.8 | ND | ND | ND |
| | trun-IL-36b IC90 (nM) | 0.6 | 1.4 | 1.7 | ND | 2 | 1.2 | 0.3 | ND | ND | ND |
| | trun-IL-36g IC90 (nM) | 0.5 | 2 | 1.4 | ND | 1.7 | 0.7 | 0.4 | ND | ND | ND |
| IL-6 | trun-IL-36a IC90 (nM) | 0.8 | 19 | 19 | ND | 14 | 17 | 0.8 | ND | ND | ND |
| | trun-IL-36b IC90 (nM) | 0.5 | 3.8 | 5.1 | ND | 5.8 | 5.3 | 0.3 | ND | ND | ND |
| | trun-IL-36g IC90 (nM) | 0.3 | 1.9 | 2.2 | ND | 1.3 | 0.8 | 0.2 | ND | ND | ND |
| IL-8 | trun-IL-36a IC90 (nM) | 0.6 | 3.3 | 3.2 | ND | 4.7 | 1.9 | 0.7 | ND | ND | ND |
| | trun-IL-36b IC90 (nM) | 0.6 | 0.6 | 0.8 | ND | 1.1 | 0.5 | 0.2 | ND | ND | ND |
| | trun-IL-36g IC90 (nM) | 0.5 | 1.4 | 0.9 | ND | 1.4 | 0.5 | 0.3 | ND | ND | ND |
| BaF cyno pNFκB | trun-IL-36a IC90 (nM) | >4000 | 0.2 | 0.5 | >4000 | 1 | 0.6 | 2.4 | >4000 | >4000 | >4000 |
| | trun-IL-36b IC90 (nM) | >333 | 1.6 | 0.7 | >333 | 2.1 | 0.9 | 3.5 | >333 | >333 | >333 |
| | trun-IL-36g IC90 (nM) | >333 | 1.5 | 0.8 | >333 | 1.5 | 1 | 5.1 | >333 | >333 | >333 |

TABLE 3

Potency of chimeric antibodies in functional cell assays
(isotype controls demonstrated no inhibition of activity at highest
concentration tested for samples)

| NCI/ADR-RES | | C33D10 | C73C5 | C81B4 |
|---|---|---|---|---|
| pNFκB | trun-IL-36a IC90 (nM) | 1.9 | 2.1 | 1.3 |
| | trun-IL-36b IC90 (nM) | 2 | 0.9 | 0.9 |
| | trun-IL-36g IC90 (nM) | 1.3 | 1.8 | 0.4 |
| GM-CSF | trun-IL-36a IC90 (nM) | 0.3 | 0.9 | ND |
| | trun-IL-36b IC90 (nM) | 0.3 | 1.1 | ND |
| | trun-IL-36g IC90 (nM) | 0.3 | 0.7 | ND |
| IL-6 | trun-IL-36a IC90 (nM) | 0.4 | 2.1 | ND |

TABLE 3-continued

Potency of chimeric antibodies in functional cell assays
(isotype controls demonstrated no inhibition of activity at highest
concentration tested for samples)

| NCI/ADR-RES | | C33D10 | C73C5 | C81B4 |
|---|---|---|---|---|
| | trun-IL-36b IC90 (nM) | 0.6 | 6.7 | ND |
| | trun-IL-36g IC90 (nM) | 0.7 | 6 | ND |
| IL-8 | trun-IL-36a IC90 (nM) | 0.4 | 0.7 | 0.4 |
| | trun-IL-36b IC90 (nM) | 0.3 | 0.4 | 0.1 |
| | trun-IL-36g IC90 (nM) | 0.2 | 0.4 | 0.1 |
| TNFα | trun-IL-36a IC90 (nM) | 2.4 | 2.5 | ND |
| | trun-IL-36b IC90 (nM) | 0.9 | 7.9 | ND |
| | trun-IL-36g IC90 (nM) | 0.6 | 1.3 | ND |
| BaF cyno pNFκB | trun-IL-36a IC90 (nM) | ND | 1.2 | 42 |
| | trun-IL-36b IC90 (nM) | ND | 4.1 | 48 |
| | trun-IL-36g IC90 (nM) | ND | 4.3 | 28 |

Example 4: Binding of Mouse Anti-Human IL-36R Antibodies to Human IL-36R Expressing Cells Protocol for Binding of Antibodies by Flow Cytometry HEK293 cells transfected with full-length human IL-36R or NCI/ADR-RES cells were passaged for 24 hours prior to staining. Cells were removed from flasks by rinsing with 10 ml of 5 mM EDTA in PBS, and then incubated at 37° C. for 10 min with an additional 10 ml of 5 mM EDTA and 2.5 ml of Accumax to declump/disperse cells. Antibodies were then diluted to specified concentrations in PBS+2% BSA, and cells incubated for 20 min at room temperature. Excess antibody was then washed by adding 200 μl of PBS and then centrifuged. Secondary reagent was then added at 50 μl per well and cells are incubated for 15 min at room temperature and then washed as above. Cells were resuspended in 200 μl PBS and analyzed by flow cytometry. The binding $EC_{50}$'s for the mouse anti-human IL-36R antibodies binding to human IL-36R HEK transfectants are shown in Table 4.

TABLE 4

| Clone | $EC_{50}$(M) binding to HEK-IL-36R cells |
|---|---|
| 33D10 | 4.748e−010 |
| 67E7 | 5.321e−010 |
| 73F6 | 7.456e−010 |
| 76E10 | 4.257e−010 |
| 78C8 | 5.289e−010 |
| 81A1 | 2.795e−010 |
| 81B4 | 3.016e−010 |
| 89A12 | 6.089e−010 |

Example 5: Production of Humanized IL-36R Antibodies

In order to reduce potential immunogenicity following administration in man the mouse anti-human IL-36R monoclonal antibodies 81B4 and 73C5 were 'humanized' through a design and screening process. Human framework sequences were selected for the mouse leads based on the framework homology, CDR structure, conserved canonical residues, conserved interface packing residues and other parameters. The specific substitution of amino acid residues in these framework positions can improve various aspects of antibody performance including binding affinity and/or stability, over that demonstrated in humanized antibodies formed by "direct swap" of CDRs or HVLs into the human germline framework regions. Fabs that showed better or equal binding and improved expression as compared to the chimeric parent Fab were selected for further characterization. Representative humanized variable regions for antibody 81B4 and 73C5 are shown in are shown the specification section. In this manner, Antibody B1 to Antibody B6 were humanized antibodies derived from mouse antibody 81B4 (cloned into a human IgG1KO (KO=knock-out)/kappa backbone. Antibodies B1 to B6 are shown in Table A. Antibody C1 to Antibody C3 were humanized antibodies derived from mouse antibody 73C5 (cloned into a human IgG1-KO (KO=knock-out)/kappa backbone. Antibodies C1 to C3 are shown in Table C.

Example 6: Binding of Humanized IL-36R Antibodies

Kinetics and binding affinities of humanized anti-IL-36R antibodies binding to recombinant human IL-36R were measured using the PROTEON, surface plasmon resonance, (Bio-Rad, Hercules, Calif.). Human IL-36R was immobilized at 5 different surface densities and results analyzed using global fit (see Table 5 showing results of three experiments). Binding of the humanized antibodies to NCI/ADR-RES cells via flow cytometry was measured using protocol described in Example 4 (See Table 5 for $EC_{90}$ values).

TABLE 5

Molecular and Cellular Binding affinities of humanized anti-human IL-36R antibodies.

| Antibody (LC + HC) | $K_D$ ± Standard Deviation (pM) | $EC_{90}$ (nM) |
|---|---|---|
| B1 – 32_138 + 33_49 | 27 ± 2.5 | 2.0 |
| B2 – 32_138 + 33_85 | 32 ± 5.4 | 2.3 |
| B3 – 32_138 + 33_90 | 20 ± 2.2 | 1.4 |
| B4 – 32_105 + 33_85 | 35 ± 3.7 | 1.5 |
| B5 – 32_105 + 33_90 | 24 ± 7.6 | 1.7 |
| B6 – 32_105 + 33_49 | 41 ± 4.9 | 1.7 |

Example 7: Potency of Humanized Anti-Human IL-36R Antibodies in Functional Human Assays Functional blockade of signaling with the humanized IL-36R variants from human NCI/ADR-RES cells were tested as described in Example 3. $IC_{90}$ results for the humanized anti-human IL-36R antibodies in human functional assays (pNFκB and cytokine release) with human IL-36 ligands are shown in Table 6.

TABLE 6

Potency [IC$_{90}$ (nM)] of humanized antibodies in human functional NCI/ADR-RES cell assays (Results equal averages of at least 2 experiments. Isotype controls demonstrated no inhibition of activity at highest concentration tested for samples)

| | Ligand | B1 | B2 | B3 | B4 | B5 | B6 | C1 | C2 | C3 |
|---|---|---|---|---|---|---|---|---|---|---|
| pNFκB | trun-IL-36a | 3.9 | 5.3 | 2.3 | 1.7 | 2.6 | 1.8 | 4.6 | 9.7 | 9.8 |
| | trun-IL-36b | 3.4 | 3.4 | 2.9 | 2.2 | 2.8 | 2.4 | 5.5 | 8.6 | 5.6 |
| | trun-IL-36g | 2.5 | 2.3 | 2.1 | 1.5 | 1.5 | 1.5 | 3.4 | 6.1 | 5.1 |
| IL-8 | trun-IL-36a | 4.0 | 2.8 | 2.3 | 2.6 | 2.6 | 2.2 | NA | NA | NA |
| | trun-IL-36b | 3.2 | 2.9 | 2.7 | 2.9 | 2.5 | 2.3 | NA | NA | NA |
| | trun-IL-36g | 4.2 | 3.5 | 3.4 | 3.2 | 2.8 | 2.4 | NA | NA | NA |

Example 8: Potency of Anti-IL-36R Antibodies in Functional Human Primary Keratinocyte Assays Protocols: Human Primary Epidermal Keratinocyte pNFkB/Cytokine Release Assays Cells were plated at 30,000 cells/well in culture media in 96 well plates and incubated overnight at 37° C., 5% CO$_2$. Assays were then performed as described in Example 3.
Results: IC$_{90}$ results for mouse, chimeric, and humanized anti-IL-36R antibodies in human primary keratinocyte assays (pNFkB and IL-8 release) stimulated with human IL-36 ligands are shown in Table 7, Table 8, and Table 9, respectively.

TABLE 7

(isotype controls demonstrated no inhibition of activity at highest concentration tested for samples)

| NHK | | 33D10 | 73C5 | 73F6 | 78C8 | 81A1 | 81B4 |
|---|---|---|---|---|---|---|---|
| pNFκB | trun-IL-36a IC90 (nM) | 1.8 | 10.7 | 8.2 | 11.6 | ND | 1.3 |
| | trun-IL-36b IC90 (nM) | 2.3 | 14.4 | 5.2 | 14.2 | ND | 1.1 |
| | trun-IL-36g IC90 (nM) | 0.8 | 1.7 | 1.3 | 10.6 | ND | 0.5 |
| IL-8 | trun-IL-36a IC90 (nM) | 1.5 | 20.8 | 17.8 | 19.3 | ND | 0.7 |
| | trun-IL-36b IC90 (nM) | 3.0 | 46 | 26 | 34 | ND | 1.2 |
| | trun-IL-36g IC90 (nM) | 0.8 | 2.4 | 2.1 | 3.6 | ND | 0.5 |

TABLE 8

Potency of chimeric anti-IL-36R antibodies in primary human keratinocyte assays (isotype controls demonstrated no inhibition of activity at highest concentration tested for samples)

| NHK | | C73C5 | C81A1 | C81B4 |
|---|---|---|---|---|
| pNFκB | trun-IL-36a IC90 (nM) | 20.5 | ND | 1.4 |
| | trun-IL-36b IC90 (nM) | 8.3 | 7.1 | 1.8 |
| | trun-IL-36g IC90 (nM) | 1.4 | ND | 0.5 |
| IL-8 | trun-IL-36a IC90 (nM) | 29.7 | 23.4 | 1.2 |
| | trun-IL-36b IC90 (nM) | 49.3 | 87 | 11.1 |
| | trun-IL-36g IC90 (nM) | 3.6 | 1.2 | 0.3 |

TABLE 9

Potency of humanized anti-IL-36R antibodies in primary human keratinocyte assays (isotype controls demonstrated no inhibition of activity at highest concentration tested for samples)

| NHK | | BI 1 | BI 2 | BI 3 |
|---|---|---|---|---|
| pNFκB | trun-IL-36a IC90 (nM) | 2.9 | 2.1 | 2.2 |
| | trun-IL-36b IC90 (nM) | 3.6 | 2.9 | 1.9 |
| | trun-IL-36g IC90 (nM) | 1.0 | 1.3 | 0.7 |
| IL-8 | trun-IL-36a IC90 (nM) | 2.3 | 2.8 | 1.8 |
| | trun-IL-36b IC90 (nM) | 3.9 | 4.1 | 3.5 |
| | trun-IL-36g IC90 (nM) | 0.8 | 0.8 | 0.8 |

Example 9: Potency of Anti-IL-36R Antibodies in Functional Human Primary Intestinal Epithelial Cell Assays Protocols: Human Primary Intestinal Epithelial Cell pNFkB/Cytokine Release Assays Cells were plated at 30,000 cells/well in culture media in 96 well plate and incubated overnight at 37° C., 5% CO$_2$. Assays were then performed as described in Example 3.
Results: IC$_{90}$ results for mouse anti-IL-36R antibodies in human primary intestinal epithelial cell assays (pNFkB and IL-8 release) stimulated with human IL-36 ligands are shown in Table 10.

TABLE 10

Potency of mouse anti-IL-36R antibodies in primary human intestinal epithelial cell assays (isotype controls demonstrated no inhibition of activity at highest concentration tested for samples)

| HIE | | 73C5 | 81B4 |
|---|---|---|---|
| pNFκB | trun-IL-36a IC90 (nM) | 21 | 1.3 |
| | trun-IL-36b IC90 (nM) | 20 | 7.4 |
| | trun-IL-36g IC90 (nM) | 32 | 9.5 |
| IL-8 | trun-IL-36a IC90 (nM) | 123 | 5.8 |
| | trun-IL-36b IC90 (nM) | 154 | 9.8 |
| | trun-IL-36g IC90 (nM) | ND | 16 |

Example 10: Potency of Anti-IL-36R Antibodies in Functional Human Primary Intestinal Myofibroblast Assays Protocols: Human Primary Intestinal Myofibroblast pNFκB/Cytokine Release Assays Cells were plated at 30,000 cells/well in culture media in 96 well plate and incubated at 37° C., 5% CO$_2$. Assays were then performed as described in Example 3.
Results: IC$_{90}$ results for anti-IL-36R antibodies in human primary intestinal myofibroblast assays (pNFkB and IL-8 release) stimulated with human IL-36 ligands are shown in Table 11 and Table 12.

TABLE 11

Potency of mouse and chimeric anti-IL-36R antibodies in primary human intestinal myofibroblast assays
(isotype controls demonstrated no inhibition of activity at highest concentration tested for samples)

| HIM | | 81B4 | C81B4 |
|---|---|---|---|
| pNFκB | trun-IL-36a IC90 (nM) | 7 | 6.2 |
| | trun-IL-36b IC90 (nM) | 4 | 2.3 |
| | trun-IL-36g IC90 (nM) | 3.6 | 0.9 |
| IL-8 | trun-IL-36a IC90 (nM) | 2 | 2.3 |
| | trun-IL-36b IC90 (nM) | 2.3 | 1.4 |
| | trun-IL-36g IC90 (nM) | 2.9 | 2 |

TABLE 12

Potency of humanized anti-IL-36R antibodies in primary human intestinal myofibroblast assays
(isotype controls demonstrated no inhibition of activity at highest concentration tested for samples)

| HIM | | B3 | B5 | B6 |
|---|---|---|---|---|
| pNFkB | trun-IL-36a IC90 (nM) | 9.8 | 5.4 | 3.2 |
| | trun-IL-36b IC90 (nM) | 3.7 | 1.7 | 2.8 |
| | trun-IL-36g IC90 (nM) | 2.6 | 1.7 | 3.7 |
| IL-8 | trun-IL-36a IC90 (nM) | 4.4 | 3.8 | 2.1 |
| | trun-IL-36b IC90 (nM) | 2.8 | 2.6 | 2.0 |
| | trun-IL-36g IC90 (nM) | 5.8 | 6.7 | 5.2 |

Example 11: Potency of Anti-IL-36R Antibodies in Functional Human Primary Dermal Fibroblast Assays Protocols: Human Primary Dermal Fibroblast pNFκB/Cytokine Release Assays Cells were plated at 30,000 cells/well in culture media in 96 well plate and incubated overnight at 37° C., 5% $CO_2$. Assays were then performed as described in Example 3.

Results: $IC_{90}$ results for anti-IL-36R antibodies in human primary dermal fibroblast assays (pNFkB and IL-8 release) stimulated with human IL-36 ligands are shown in Table 13 and Table 14.

TABLE 13

Potency of mouse and chimeric anti-IL-36R antibodies in primary human dermal fibroblast assays
(isotype controls demonstrated no inhibition of activity at highest concentration tested for samples)

| HDF | | 81B4 | C81B4 |
|---|---|---|---|
| pNFκB | trun-IL-36a IC90 (nM) | 1.9 | 1.8 |
| | trun-IL-36b IC90 (nM) | 4.9 | 3.4 |
| | trun-IL-36g IC90 (nM) | 3.9 | 7.4 |
| IL-8 | trun-IL-36a IC90 (nM) | 0.9 | 0.6 |
| | trun-IL-36b IC90 (nM) | 0.4 | 0.5 |
| | trun-IL-36g IC90 (nM) | 0.4 | 0.3 |

TABLE 14

Potency of humanized anti-IL-36R antibodies in primary human dermal fibroblast assays
(isotype controls demonstrated no inhibition of activity at highest concentration tested for samples)

| HDF | | B3 | B5 | B6 |
|---|---|---|---|---|
| pNFκB | trun-IL-36a IC90 (nM) | 6.4 | 10.2 | 3.8 |
| | trun-IL-36b IC90 (nM) | 13.5 | 9.9 | 9 |
| | trun-IL-36g IC90 (nM) | 10 | 8.6 | 16.8 |
| IL-8 | trun-IL-36a IC90 (nM) | 2.1 | 1.5 | 1.4 |
| | trun-IL-36b IC90 (nM) | 1.3 | 1.2 | 1 |
| | trun-IL-36g IC90 (nM) | 1.1 | 1.1 | 0.7 |

Example 12: Potency of Mouse Anti-IL-36R Antibodies in Functional Human Primary Proximal Tubular Cell Assays Protocol: Human Primary Proximal Tubular Cells pNFκB/Cytokine Release Assays.

Cells were plated at 5,000 cells/well in culture media in 96 well plate and incubated overnight at 37° C., 5% $CO_2$. Assays were performed as described in Example 3.

Results: $IC_{90}$ results for mouse, chimeric, and humanized anti-IL-36R antibodies in human primary proximal tubular cell assays (IL-8 release) stimulated with human IL-36 ligands are shown in Table 15.

TABLE 15

Potency of mouse and human anti-IL-36R antibodies in primary human proximal tubular cell assays
(isotype controls demonstrated no inhibition of activity at highest concentration tested for samples)

| HPT | | 81B4 | B3 | B5 | B6 |
|---|---|---|---|---|---|
| IL-8 | trun-IL-36a IC90 (nM) | .04 | ND | 5 | ND |
| | trun-IL-36b IC90 (nM) | .01 | ND | 5 | ND |
| | trun-IL-36g IC90 (nM) | .04 | ND | 3 | ND |

Example 13: Inhibition of IL-8 Production from IL-36γ Stimulated Reconstructed Human Epidermis Protocol Reconstructed Epidermis Anti-IL-36R antibodies (1.5 µg/ml) were pre-incubated with reconstructed human epidermis and stimulated with human recombinant IL-36γ (20 ng/ml). Recombinant human IL-1β (20 ng/ml; R & D Systems) was used as a positive control. After 24 hours in culture, cell supernatants were collected and assayed for IL-8 (assays for IL-8 are described in Example 3). Samples were tested in triplicate and the average pg/ml±standard error is shown in the table below (Table 16).

TABLE 16

| Antibody | Cytokine Stimulation | Average IL-8 (pg/ml) +/− Standard Error |
|---|---|---|
| No antibody | None | 57.3 ± 15.3 |
| 33D10 | None | 15.8 ± 0.7 |
| No antibody | 20 ng/mL IL-1β | 158.9 ± 13.3 |
| 33D10 | 20 ng/mL IL-1β | 168.5 ± 22.6 |
| No antibody | 20 ng/mL IL-36γ | 142.1 ± 22.2 |
| 33D10 | 20 ng/mL IL-36γ | 38.63 ± 6.7 |

Example 14: Inhibition of IL-36 Ligand Induced S100A7 and S100A12 Gene Expression in Reconstructed Human Epidermis Stimulation of reconstructed human epidermis with agonsitic IL-36 ligands induces S100A7 and S100A12 gene expression. S100A7 and S100A12 are genes located within the epidermal differentiation complex.

Protocol:

Reconstructed human epidermis were incubated with anti-IL-36R antibodies (1.5 µg/ml) and stimulated with human recombinant IL-36γ (20 ng/ml). Recombinant human IL-1β (20 ng/mL; R & D Systems) was used as a positive control. After 24 hours in culture at 5% $CO_2$ and 37° C., RNA was isolated from the reconstructed human epidermis and assayed for gene expression by real-time reverse trancriptase-polymerase chain reaction. Relative expression was calculated using the $2^{-\Delta\Delta Ct}$ method. Samples were tested in triplicate and the average expression±standard error is shown in the table below (Table 17).

TABLE 17

| Antibody | Cytokine Stimulation | Mean S100A7 Expression +/− Standard Error | Mean S100A12 Expression +/− Standard Error |
|---|---|---|---|
| No antibody | None | 1.00 ± 0.79 | 1.00 ± 0.47 |
| 33D10 | None | 3.92 ± 0.36 | 1.93 ± 0.02 |
| No antibody | 20 ng/mL IL-1β | 76.03 ± 24.66 | 47.84 ± 9.24 |
| 33D10 | 20 ng/mL IL-1β | 95.83 ± 11.83 | 76.41 ± 6.92 |
| No antibody | 20 ng/mL IL-36γ | 19.57 ± 3.26 | 20.53 ± 5.21 |
| 33D10 | 20 ng/mL IL-36γ | 3.47 ± 1.37 | 2.01 ± 0.35 |

Example 15: Efficacy of Anti-IL-36R Antibody in Xenotransplant Model of Psoriasis Protocol:

Blood and non-lesional skin biopsies were obtained from 24 psoriasis patients that were clinically diagnosed by a dermatologist. Skin biopsies were transplanted onto immune-deficient NIH-Ill mice and allowed to engraft for a period of four to five weeks.

Peripheral blood mononuclear cells (PBMC) were isolated from blood collected from each donor at the time of biopsy for intradermal injection into the engrafted skin. Prior to injection, PBMC were stimulated with with 1 µg/ml Staphylococcal Enterotoxin B (Toxin Technologies, Florida, USA) and 80 U/ml human recombinant IL-2 (Peprotech Inc., Oosterhout, The Netherlands). Autologous PBMC were intradermally injected with 7.5×105 cells in PBS to synchronize the induction of skin inflammation and the psoriasis phenotype. Three weeks after the injection of cells, the biopsies were retrieved from the mice and analyzed by histology.

Figure 4:
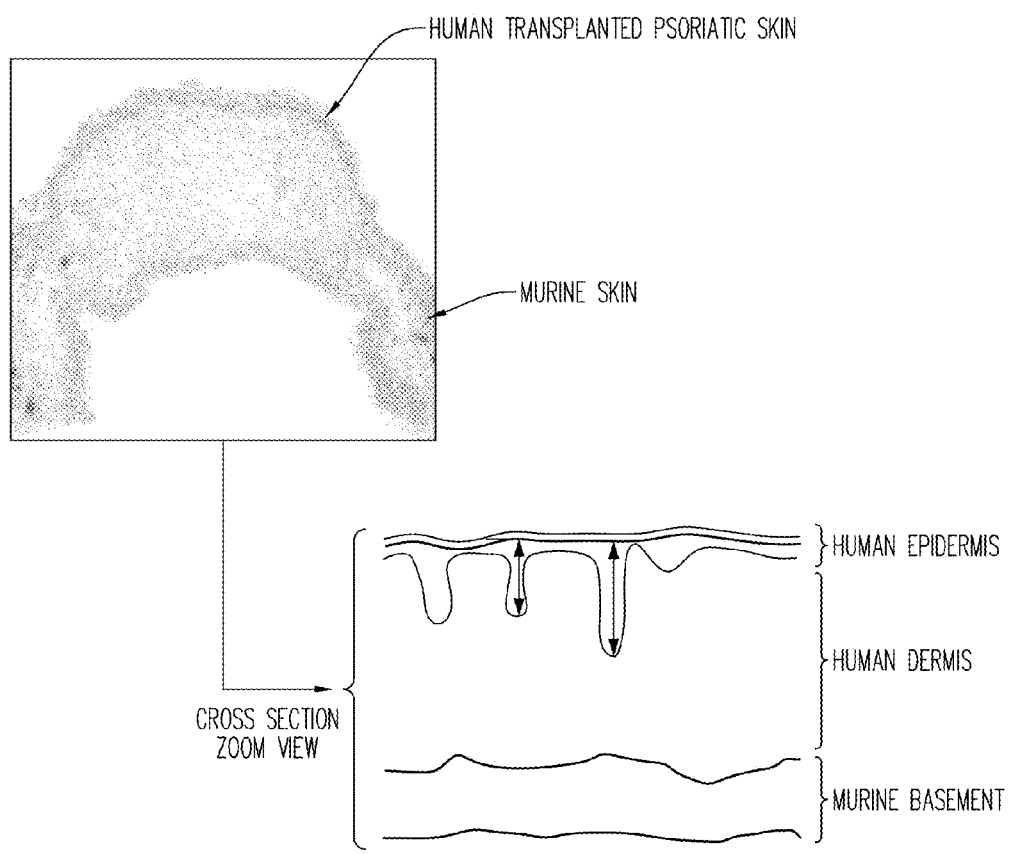
FIG. 4: Method to Evaluate Epidermal thickness of human skin sections

Histological staining was performed on cryo-preserved skin tissue of all groups. Diagonal cross sections (8 µm), covering all skin-layers, were prepared as described in FIG. 4. For assessment of epidermal thickness, two non-serial sections were randomly chosen from the center of the biopsy and stained with haematoxylin-eosin. Subsequently, sections were evaluated at a 100-fold magnification. Over the entire length of the biopsy, ridge lengths were measured in both sections using an Olympus DP71 camera and CellD imaging software (V2.7, Munster, Germany). Ridge length is defined as: the distance between the upper edge of the stratum granulosum to the bottom of the ridge. Biopsies were scored at random and in a blinded fashion.

Results for the average epidermal thickness and maximum epidermal thickness for each treatment group are shown in Table 18. Results for the net change in epidermal thickness in each treatment group are shown in Table 19.

TABLE 18

| | Average Epidermal Thickness (µM) | | | | Maximum Epidermal Thickness (µM) | | | |
|---|---|---|---|---|---|---|---|---|
| Treatment | mean | SD | N | SEM | mean | SD | N | SEM |
| Untreated | 101.4 | 34.4 | 16 | 8.6 | 147.1 | 35.0 | 16 | 8.7 |
| Vehicle | 106.0 | 31.9 | 9 | 10.6 | 151.6 | 48.9 | 9 | 16.3 |
| 33D10 | 93.4 | 24.1 | 10 | 7.6 | 130.9 | 30.8 | 10 | 9.7 |

TABLE 19

| | Average Epidermal Thickness (µM) | | | | Maximum Epidermal Thickness (µM) | | | |
|---|---|---|---|---|---|---|---|---|
| Treatment | mean | SD | N | SEM | mean | SD | N | SEM |
| Untreated | 36.2 | 31.9 | 32 | 5.6 | 52.6 | 40.0 | 32 | 7.1 |
| Vehicle | 43.5 | 30.9 | 18 | 7.3 | 63.4 | 52.0 | 18 | 12.2 |
| 33D10 | 27.8 | 26.6 | 20 | 5.9 | 35.1 | 34.1 | 20 | 7.6 |

Example 16: The Sub-Chronic Pulmonary Inflammation after 3 Weeks of Cigarette Smoke Exposure in Wild Type and Interleukin-1Receptor-Like 2 Homozygous Knockout Mice Protocol:

Wild type or interleukin-1 receptor-like 2 mice were exposed to cigarette smoke for 3 weeks to induce pulmonary distress. Weeks 1 and 2 consisted of 5 consecutive exposure days, while mice were exposed for 4 consecutive days during week 3. Mice were exposed to 5 cigarettes each day with 24 minute intervals of cigarette exposure (16 minutes) and fresh air (8 minutes). Eighteen hours following the final exposure, mice were lavaged with 2×0.8 ml of Hank's Salt Solution (0.6 mM EDTA). The supernatant and cell pellet were collected from the bronchial alveolar lavage following centrifugation for 10 minutes. Total macrophage and neutrophil cell counts in the bronchial alveolar lavage for each exposure group are shown in Table 20.

TABLE 20

| Total Cells | Cell Counts × 10^5 | | | |
|---|---|---|---|---|
| Mouse | mean | SD | N | SEM |
| WT | 2.21 | 1.47 | 9 | 0.49 |
| IL1RL2 KO | 2.45 | 0.87 | 6 | 0.36 |
| WT + CS | 9.07 | 2.83 | 10 | 0.90 |
| IL-1RL2 KO + CS | 5.32 | 1.03 | 10 | 0.32 |

TABLE 20-continued

| Macrophages | Cell Counts × 10^5 | | | |
|---|---|---|---|---|
| Mouse | mean | SD | N | SEM |
| WT | 2.08 | 1.62 | 9 | 0.54 |
| IL1RL2 KO | 2.40 | 0.86 | 6 | 0.35 |
| WT + CS | 3.36 | 1.46 | 10 | 0.46 |
| IL-1RL2 KO + CS | 3.22 | 0.86 | 10 | 0.27 |

| Neutrophils | Cell Counts × 10^5 | | | |
|---|---|---|---|---|
| Mouse | mean | SD | N | SEM |
| WT | 0.002 | 0.004 | 9 | 0.001 |
| IL1RL2 KO | 0.013 | 0.016 | 6 | 0.007 |
| WT + CS | 5.698 | 2.751 | 10 | 0.870 |
| IL-1RL2 KO + CS | 2.083 | 0.749 | 10 | 0.237 |

The invention claimed is:

1. An isolated polynucleotide comprising a sequence encoding a light chain variable region comprising the amino acid sequence of any one of SEQ ID NO: 76, 77, 78, 79, 80, 81, 82 or 83; or a sequence encoding a heavy chain variable region comprising the amino acid sequence of any one of SEQ ID NO: 87, 88, 89, 90, 91, 92, 93, 94 or 95.

2. The isolated polynucleotide according to claim 1, wherein the sequence encodes a light chain variable region comprising the amino acid sequence of SEQ ID NO: 77 or 80; or a heavy chain variable region comprising the amino acid sequence of any one of SEQ ID NO: 87, 88 or 89.

3. A vector comprising a polynucleotide according to claim 1.

4. An isolated host cell comprising a polynucleotide according to claim 1.

5. A vector comprising a polynucleotide according to claim 2.

6. An isolated host cell comprising a polynucleotide according to claim 2.

7. An isolated polynucleotide comprising a sequence encoding a light chain comprising the amino acid sequence of any one of SEQ ID NO: 114, 115, 116, 117, 118, 119, 120 or 121; or a sequence encoding a heavy chain comprising the amino acid sequence of any one of SEQ ID NO: 125, 126, 127, 128, 129, 130, 131, 132 or 133.

8. An isolated polynucleotide according to claim 7, wherein the sequence encodes a light chain comprising the amino acid sequence of SEQ ID NO: 115 or 118; or a heavy chain comprising the amino acid sequence of any one of SEQ ID NO: 125, 126 or 127.

9. A vector comprising a polynucleotide according to claim 8.

10. An isolated host cell comprising a polynucleotide according to claim 8.

11. An isolated host cell comprising:
   a) a polynucleotide comprising a sequence encoding a light chain variable region comprising the amino acid sequence of SEQ ID NO: 77 and a polynucleotide comprising a sequence encoding a heavy chain variable region comprising the amino acid sequence of SEQ ID NO: 87; or
   b) a polynucleotide comprising a sequence encoding a light chain variable region comprising the amino acid sequence of SEQ ID NO: 77 and a polynucleotide comprising a sequence encoding a heavy chain variable region comprising the amino acid sequence of SEQ ID NO: 88; or c) a polynucleotide comprising a sequence encoding a light chain variable region comprising the amino acid sequence of SEQ ID NO: 77 and a polynucleotide comprising a sequence encoding a heavy chain variable region comprising the amino acid sequence of SEQ ID NO: 89; or d) a polynucleotide comprising a sequence encoding a light chain variable region comprising the amino acid sequence of SEQ ID NO: 80 and a polynucleotide comprising a sequence encoding a heavy chain variable region comprising the amino acid sequence of SEQ ID NO: 87; or e) a polynucleotide comprising a sequence encoding a light chain variable region comprising the amino acid sequence of SEQ ID NO: 80 and a polynucleotide comprising a sequence encoding a heavy chain variable region comprising the amino acid sequence of SEQ ID NO: 88; or f) a polynucleotide comprising a sequence encoding a light chain variable region comprising the amino acid sequence of SEQ ID NO: 80 and a polynucleotide comprising a sequence encoding a heavy chain variable region comprising the amino acid sequence of SEQ ID NO: 89.

12. A method for the production of an anti-interleukin-36R (anti-IL-36R) antibody or antigen-binding fragment thereof comprising cultivating the host cell of claim 11 under conditions allowing the expression of the anti-IL-36R antibody or antigen-binding fragment thereof.

13. The method according to claim 12, said method further comprising recovering the anti-IL-36R antibody or antigen-binding fragment thereof.

14. An isolated host cell comprising:

a) a polynucleotide comprising a sequence encoding a light chain comprising the amino acid sequence of SEQ ID NO: 115 and a polynucleotide comprising a sequence encoding a heavy chain comprising the amino acid sequence of SEQ ID NO: 125; or b) a polynucleotide comprising a sequence encoding a light chain comprising the amino acid sequence of SEQ ID NO: 115 and a polynucleotide comprising a sequence encoding a heavy chain comprising the amino acid sequence of SEQ ID NO: 126; or c) a polynucleotide comprising a sequence encoding a light chain comprising the amino acid sequence of SEQ ID NO: 115 and a polynucleotide comprising a sequence encoding a heavy chain comprising the amino acid sequence of SEQ ID NO: 127; or d) a polynucleotide comprising a sequence encoding a light chain comprising the amino acid sequence of SEQ ID NO: 118 and a polynucleotide comprising a sequence encoding a heavy chain comprising the amino acid sequence of SEQ ID NO: 125; or e) a polynucleotide comprising a sequence encoding a light chain comprising the amino acid sequence of SEQ ID NO: 118 and a polynucleotide comprising a sequence encoding a heavy chain comprising the amino acid sequence of SEQ ID NO: 126; or f) a polynucleotide comprising a sequence encoding a light chain comprising the amino acid sequence of SEQ ID NO: 118 and a polynucleotide comprising a sequence encoding a heavy chain comprising the amino acid sequence of SEQ ID NO: 127.

15. A method for the production of an anti-IL-36R antibody or antigen-binding fragment thereof comprising cultivating the host cell of claim 14 under conditions allowing the expression of the anti-IL-36R antibody or antigen-binding fragment thereof.

16. The method according to claim 15, said method further comprising recovering the anti-IL36R antibody or antigen-binding fragment thereof.

17. An isolated polynucleotide comprising a sequence encoding a light chain comprising the amino acid sequence of SEQ ID NO: 115; or a sequence encoding a heavy chain comprising the amino acid sequence of SEQ ID NO: 125.

18. An isolated polynucleotide comprising a sequence encoding a light chain comprising the amino acid sequence of SEQ ID NO: 115; or a sequence encoding a heavy chain comprising the amino acid sequence of SEQ ID NO: 126.

19. An isolated polynucleotide comprising a sequence encoding a light chain comprising the amino acid sequence of SEQ ID NO: 118; or a sequence encoding a heavy chain comprising the amino acid sequence of SEQ ID NO: 125.

20. An isolated polynucleotide comprising a sequence encoding a light chain comprising the amino acid sequence of SEQ ID NO: 118; or a sequence encoding a heavy chain comprising the amino acid sequence of SEQ ID NO: 126.

21. An isolated polynucleotide comprising a sequence encoding a light chain comprising the amino acid sequence of SEQ ID NO: 118; or a sequence encoding a heavy chain comprising the amino acid sequence of SEQ ID NO: 127.

* * * * *